United States Patent
Ishizuka et al.

(10) Patent No.: US 6,218,427 B1
(45) Date of Patent: Apr. 17, 2001

(54) CHROMENE-3-CARBOXYLATE DERIVATIVES

(75) Inventors: Natsuki Ishizuka; Ken-ichi Matsumura; Katsunori Sakai; Toshiro Konoike, all of Osaka; Tadahiko Yorifuji, Hyogo; Seijiro Hara, Kyoto; Yoshiyuki Matsuo, Osaka, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/242,898

(22) PCT Filed: Aug. 22, 1997

(86) PCT No.: PCT/JP97/02916
§ 371 Date: Apr. 26, 1999
§ 102(e) Date: Apr. 26, 1999

(87) PCT Pub. No.: WO98/08836
PCT Pub. Date: Mar. 5, 1998

(30) Foreign Application Priority Data

Aug. 27, 1996 (JP) .................................. 8-225409
Oct. 11, 1996 (JP) .................................. 8-270052

(51) Int. Cl.⁷ .......................... A61K 31/35; A61K 31/38; C07D 311/04; C07D 335/04
(52) U.S. Cl. .......................... 514/456; 514/432; 549/405; 549/402; 549/23
(58) Field of Search .................. 549/23, 402, 405; 514/432, 456

(56) References Cited

U.S. PATENT DOCUMENTS

| | | | |
|---|---|---|---|
| 4,665,202 | * 5/1987 | Rimbault et al. | 549/402 |
| 5,646,308 | * 7/1997 | Koga et al. | 549/404 |
| 6,034,256 | * 3/2000 | Carter et al. | 549/456 |
| 6,043,269 | * 3/2000 | Jacobsen et al. | 514/422 |

FOREIGN PATENT DOCUMENTS

| | | |
|---|---|---|
| 0139615 | 5/1985 | (EP) . |
| 0140830 | 5/1985 | (EP) . |
| 585913 | 3/1994 | (EP) . |
| 9308799 | 5/1993 | (WO) . |
| 9425013 | 11/1994 | (WO) . |
| 9620296 | 7/1996 | (WO) . |
| 9847890 | 10/1998 | (WO) . |

OTHER PUBLICATIONS

Indian J. Chem., 8 [5] (1970) p. 472–473.
Tetrahedron, 46 [8] (1990) p. 3029–3036.
American Journal of Pathology vol. 146 No. 4 819–826 (1995).

* cited by examiner

Primary Examiner—Deborah C. Lambkin
(74) Attorney, Agent, or Firm—Birch, Stewart, Kolasch & Birch, LLP

(57) ABSTRACT

The present invention provides a compound of the formula (I):

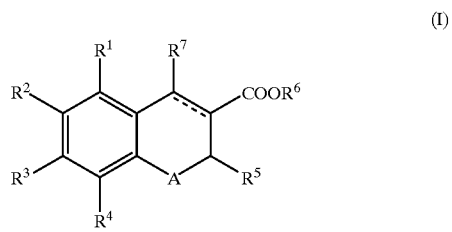

wherein $R^1$, $R^2$, $R^3$ and $R^4$ are each independently hydrogen, optionally substituted alkyl, hydroxy, optionally substituted alkoxy or the like, $R^5$ is optionally substituted alkyl, optionally substituted aryl, optionally substituted heterocyclic or the like, $R^6$ is hydrogen, optionally substituted alkyl or the like, $R^7$ is hydrogen, optionally substituted alkyl, optionally substituted alkoxy, optionally substituted aryl, optionally substituted heterocyclic or the like, A is S or O and a broken line represents presence or absence of a bond, pharmaceutically acceptable salt or hydrate thereof and a pharmaceutical composition or a pharmaceutical composition for use as an endothelin receptor antagonist, a peripheral circulation insufficiency-improving agent or a macrophage foam cell formation inhibitor comprising the compound.

11 Claims, No Drawings

CHROMENE-3-CARBOXYLATE DERIVATIVES

This application is the national phase under 35 U.S.C. §371 of prior PCT International Application No. PCT/JP97/02916 which has an International filing date of Aug. 22, 1997 which designated the United States of America.

TECHNICAL FIELD

The present invention relates to compounds useful as medicines and use of the compound. Specifically, the present invention relates to pharmaceutical compositions containing a chromen-3-carboxylic acid derivative, pharmaceutical compositions for use as an endothelin receptor antagonist containing the same, pharmaceutical compositions for use as a peripheral circulation insufficiency-improving agent containing the same and an novel chromen-3-carboxylic acid derivative. Further, the present invention relates to a pharmaceutical composition for use as a macrophage foam cell formation inhibitor containing an endothelin antagonist.

BACKGROUND ART

Endothelins are vasoactive peptides comprising 21 amino acid residues, are isolated from endothelial cells, and associates with homeostasis of a circulatory system. Endothelins act as aggravation factors of cardiovascular diseases such as hypertension, pulmonary hypertension, stroke, cerebrovascular spasm, acute renal insufficiency, acute proliferative nephropathy, acute myocardial infarction, chronic heart failure, vascular intimal thickness and the like by the medium of endothelin receptors.

Two kinds of receptor subtypes, an endothelin A and an endothelin B receptors, are known and three types of receptor antagonists, A-selective, B-selective and A & B non-selective antagonists, have been presumed to exist. Although there remain many unknown matters about what kind of diseases are associated with any type of receptors, they have been gradually made clear. For example, an endothelin A receptor is considered to be associated with acute and chronic diseases such as hypertension, pulmonary hypertension, cerebral stroke, cerebrovascular spasm, cerebral edema, acute renal insufficiency, myocardial infarction, chronic heat insufficiency, asthma and the like and therefore, the antagonists have been expected to be useful for treatment of these diseases. There is a possibility that an endothelin B receptor is associated with the appearance and progression of cardiovascular disease and further, it is considered to associate with metabolism of endothelin in blood, the vascular intimal thickness and development and differentiation of a certain kind of cells.

Peptide-type antagonists have been developed as endothelin receptor antagonists but there are many problems for application as a medicament of chronic diseases. For example, they tend to be readily metabolized in the living body, the duration of action is short, and they are not effective in oral administration and the like. Endothelin is associated with diverse diseases, the effect is potent and the mechanism of action is complicated. Accordingly, development of a non-peptide type endothelin antagonist having a long duration of action and a superior oral availability has been desired.

Indan and inden derivatives are disclosed in JP-A 7-501322 and WO 94/25013 as an endothelin receptor antagonist but the data of pharmacological activities indicating effectiveness of these derivatives as medicaments have not been disclosed.

Arteriosclerosis is caused by a combination of many risk factors and injury factors and one of the examples of risk factors is cholesterol. Law density cholesterol (hereinafter referred to as LDL) is oxidized after accumulation on artery walls, taken in macrophages and the macrophages turn foam cells. It is considered that accumulation of foam cell forming-macrophages accelerates the proliferation of smooth muscle cells and cell intimal fibrous thickness and finally leads up to an atherosclerotic lesion. According to these knowledge, a macrophage foam cell formation inhibitor is expected to be effective for treating and/or preventing the atherosclerosis.

The endothelin antagonists are generally supposed to have an anti-arteriosclerosis activity and the mechanism has been considered to be related to a thrombus formation caused by vasoconstriction or to a proliferation promoting effect on a vascular smooth muscle cell. With regard to an inhibition of macrophage foam cell formation, only BMS-182874 has been disclosed to reduce the number and size of foam cells (American Journal of Pathology vol. 146, No.4, 819–826 (1995)).

Compounds having similar structure have been disclosed in JP-A 60-149580 and JP-A 60-149581 but their endothelin antagonistic activity is not suggested at all.

DISCLOSURE OF INVENTION

These inventors discovered that compounds of the following formula (Iα) have a potent and orally available endothelin receptor antagonistic activity and accomplished the present invention. The present invention provides pharmaceutical compositions for use as an endothelin receptor antagonist comprising a compound of the formula (Iα):

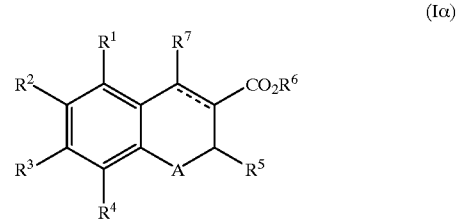

(Iα)

wherein $R^1$, $R^2$, $R^3$ and $R^4$ are each independently hydrogen, optionally substituted alkyl, optionally substituted alkenyl, optionally substituted alkynyl, optionally substituted cycloalkyl, hydroxy, halogen, optionally substituted alkoxy, optionally substituted alkenyloxy, optionally substituted alkynyloxy, optionally substituted cycloalkoxy, optionally substituted acyloxy or optionally substituted amino, $R^5$ is optionally substituted alkyl, optionally substituted alkenyl, optionally substituted alkynyl optionally substituted aryl, optionally substituted heterocyclic or optionally substituted cycloalkyl, $R^6$ is hydrogen, optionally substituted alkyl or optionally substituted aryl, $R^7$ is hydrogen, optionally substituted alkyl, optionally substituted alkenyl, optionally substituted alkynyl, optionally substituted cycloalkyl halogen, optionally substituted alkoxy, optionally substituted alkenyloxy, optionally substituted alkynyloxy, optionally substituted aryl, optionally substituted aryloxy, optionally substituted heterocyclic, optionally substituted heterocyclooxy, optionally substituted acyloxy, optionally substituted alkylthio, optionally substituted alkenylthio, optionally substituted alkynylthio or optionally substituted amino, A is S or O and a broken line represents the presence or absence of a bond, or pharmaceutically acceptable salt, hydrate or prodrug thereof (hereinafter referred to as a compound (Iα)) as an active ingredient. The present invention provides compounds of the formula (I):

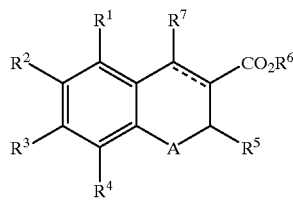

(I)

wherein $R^1$–$R^6$, A and a broken line are the same as defined above, $R^7$ is optionally substituted alkyl, optionally substituted alkenyl, optionally substituted alkynyl, optionally substituted cycloalkyl, optionally substituted alkenyloxy, optionally substituted alkynyloxy, optionally substituted aryl, optionally substituted aryloxy, optionally substituted heterocyclic, optionally substituted heterocyclooxy, optionally substituted acyloxy, optionally substituted alkylthio, optionally substituted alkenylthio, optionally substituted alkynylthio or optionally substituted amino, excluding a compound wherein $R^2$ is methyl, $R^5$ is optionally substituted alkyl, $R^7$ is phenyl and A is O, or pharmaceutically acceptable salt or hydrate thereof (hereinafter referred to as compound (I)), or a compound of the formula (I'):

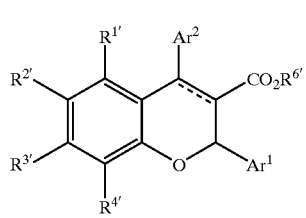

(I')

wherein $R^{1'}$, $R^{2'}$, $R^{3'}$ and $R^{4'}$ are each independently hydrogen, optionally substituted alkyl optionally substituted alkenyl, optionally substituted cycloalkyl, hydroxy, halogen, optionally substituted alkoxy, optionally substituted acyloxy or optionally substituted amino, $R^6$ is hydrogen or alkyl, $Ar^1$ and $Ar^2$ are each independently optionally substituted aryl or optionally substituted heteroaryl and a broken line represents presence or absence of a bond, or pharmaceutically acceptable salt or hydrate thereof (hereinafter referred to as compound (I')). The present invention provides pharmaceutical compositions comprising one of compounds (1) and/or (I') and pharmaceutical compositions for use as an endothelin receptor antagonist comprising the same.

As another embodiment, the present invention provides a method for treating or preventing diseases associated with endothelin, which comprises administering an effective amount of the compounds (Iα), (I) and/or (I') (hereinafter referred to as the compound group (I)). The present invention provides use of the compound group (I) for the manufacture of a medicament for treating or preventing diseases associated with endothelins.

The present invention provides a pharmaceutical compositions for use as a therapeutic agent for peripheral circulation insufficiency-improvement comprising one of the compound group (I). The present invention provides pharmaceutical compositions for use as a macrophage foam cell formation inhibitor comprising an endothelin antagonist, preferably one of the compound group (I).

BEST MODE FOR CARRYING OUT THE INVENTION

The preferable embodiments of the present invention are, in the formula (I), (1) a compound wherein $R^1$ is hydrogen, optionally substituted alkyl, hydroxy or optionally substituted alkoxy (hereinafter referred to as "$R^1$ is $R^1$-1"), preferably $R^1$ is hydrogen or optionally substituted alkoxy (hereinafter referred to as "$R^1$ is $R^1$-2"), more preferably $R^1$ is hydrogen (hereinafter referred to as "$R^1$ is $R^1$-3"), (2) a compound wherein $R^2$ is hydrogen, optionally substituted alkyl, hydroxy or optionally substituted alkoxy (hereinafter referred to as "$R^2$ is $R^2$-1"), preferably $R^2$ is hydrogen, alkyl or optionally substituted alkoxy (hereinafter referred to as "$R^2$ is $R^2$-2"), more preferably $R^2$ is optionally substituted alkoxy wherein the substituent is hydroxy, alkoxy, formyl or heterocyclic (hereinafter referred to as "$R^2$ is $R^2$-3"), (3) a compound wherein $R^3$ is hydrogen, optionally substituted alkyl, hydroxy or optionally substituted alkoxy (hereinafter referred to as "$R^3$ is $R^3$-1), preferably $R^3$ is hydrogen or optionally substituted alkoxy (hereinafter referred to as "$R^3$ is $R^3$-2"), more preferably $R^3$ is hydrogen (hereinafter referred to as "$R^3$ is $R^3$-3"), (4) a compound wherein $R^4$ is hydrogen, optionally substituted alkyl, hydroxy or optionally substituted alkoxy (hereinafter referred to as "$R^4$ is $R^4$-1"), preferably $R^4$ is hydrogen, alkyl or optionally substituted alkoxy (hereinafter referred to as "$R^4$ is $R^4$-2"), more preferably $R^4$ is hydrogen (hereinafter referred to as "$R^4$ is $R^4$-3"), (5) a compound wherein $R^5$ is optionally substituted alkyl, optionally substituted alkenyl, optionally substituted aryl or optionally substituted heterocyclic (hereinafter referred to as "$R^5$ is $R^5$-1"), preferably $R^5$ is optionally substituted aryl or optionally substituted heterocyclic (hereinafter referred to as "$R^5$ is $R^5$-2"), more preferably $R^5$ is optionally substituted aryl wherein the substituent is alkyl, alkoxy or alkylenedioxy or optionally substituted heterocyclic wherein the substituent is halogen, alkyl, alkoxy or alkylenedioxy (hereinafter referred to as "$R^5$ is $R^5$-3"), most preferably $R^5$ is optionally substituted aryl wherein the substituent is alkyl, alkoxy or alkylenedioxy (hereinafter referred to as "$R^5$ is $R^5$-4"), (6) a compound wherein $R^6$ is hydrogen or alkyl (hereinafter referred to as "$R^6$ is $R^6$-1"), preferably $R^6$ is hydrogen (hereinafter referred to as "$R^6$ is $R^6$-2"), (7) a compound wherein $R^7$ is optionally substituted alkyl, optionally substituted alkenyl, optionally substituted alkynyl, optionally substituted cycloalkyl, optionally substituted alkenyloxy, optionally substituted alkynyloxy, optionally substituted aryl, optionally substituted aryloxy, optionally substituted heteroaryl, optionally substituted heterocyclooxy, optionally substituted acyloxy, optionally substituted alkenylthio or optionally substituted alkynylthio (hereinafter referred to as "$R^7$ is $R^7$-1"), preferably $R^7$ is optionally substituted alkyl, alkenyl, alkynyl, cycloalkyl, alkenyloxy, optionally substituted aryl, optionally substituted aryloxy or optionally substituted thienyl (hereinafter referred to as "$R^7$ is $R^7$-2"), more preferably $R^7$ is optionally substituted alkyl, optionally substituted aryl or optionally substituted aryloxy (hereinafter referred to as "$R^7$ is $R^7$-3"), most preferably $R^7$ is optionally substituted aryl wherein the substituent is alkyl, alkoxy, carboxyalkoxy, halogen, alkylenedioxy, amino or alkylamino or optionally substituted aryloxy wherein the substituent is alkyl, alkoxy, carboxyalkoxy, halogen, alkylenedioxy, amino or alkylamino (hereinafter referred to as "$R^7$ is $R^7$-4"), (8) a compound wherein A is O, (9) a compound wherein a broken line represents a bond,

(10) a compound wherein $R^1$ is $R^1$-1, $R^2$ is $R^2$-1, $R^3$ is $R^3$-1 and $R^4$ is $R^4$-1, preferably $R^1$ is $R^1$-2, $R^2$ is $R^2$-2, $R^3$ is $R^3$-2 and $R^4$ is $R^4$-2, more preferably $R^1$ is $R^1$-3, $R^2$ is $R^2$-3, $R^3$ is $R^3$-3 and $R^4$ is $R^4$-3,

(11) a compound wherein $R^1$ is $R^1$-1, $R^2$ is $R^2$-1, $R^3$ is $R^3$-1, $R^4$ is $R^4$-1, $R^5$ is $R^5$-1, $R^6$ is $R^6$-1, $R^7$ is $R^7$-1 and A is O, preferably $R^1$ is $R^1$-1, $R^2$ is $R^2$-1, $R^3$ is $R^3$-1, $R^4$ is $R^4$-1, $R^5$ is $R^5$-2, $R^6$ is $R^6$-1, $R^7$ is $R^7$-1 and A is O, preferably $R^1$ is $R^1$-.1, $R^2$ is $R^2$-1, $R^3$ is $R^3$-1, $R^4$ is $R^4$-1, $R^5$ is $R^5$-3, $R^6$ is $R^6$-1, $R^7$ is $R^7$-1 and A is O,

(12) a compound wherein $R^1$ is $R^1$-1, $R^2$ is $R^2$-1, $R^3$ is $R^3$-1, $R^4$ is $R^4$-1, $R^5$ is $R^5$-1, $R^6$ is $R^6$-2, $R^7$ is $R^7$-1 and A is O,

(13) a compound wherein $R^1$ is $R^1$-1, $R^2$ is $R^2$-1, $R^3$ is $R^3$-1, $R^4$ is $R^4$-1, $R^5$ is $R^5$-1, $R^6$ is $R^6$-1, $R^7$ is $R^7$-2 and A is O, preferably $R^1$ is $R^1$-1, $R^2$ is $R^2$-1, $R^3$ is $R^3$-1, $R^4$ is $R^4$-1, $R^5$ is $R^5$-1, $R^6$ is $R^6$-1, $R^7$ is $R^7$-3 and A is O,

(14) a compound wherein $R^1$ is $R^1$-1, $R^2$ is $R^2$-1, $R^3$ is $R^3$-1, $R^4$ is $R^4$-1, $R^5$ is $R^5$-2, $R^6$ is $R^6$-2, $R^7$ is $R^7$-1 and A is O, preferably $R^1$ is $R^1$-1, $R^2$ is $R^2$-1, $R^3$ is $R^3$-1, $R^4$ is $R^4$-1, $R^5$ is $R^5$-3, $R^6$ is $R^6$-2, $R^7$ is $R^7$-1 and A is O,

(15) a compound wherein $R^1$ is $R^1$-1, $R^2$ is $R^2$-1, $R^3$ is $R^3$-1, $R^4$ is $R^4$-1, $R^5$ is $R^5$-2, $R^6$ is $R^6$-2, $R^7$ is $R^7$-2 and A is O, preferably $R^1$ is $R^1$-1, $R^2$ is $R^2$-1, $R^3$ is $R^3$-1, $R^4$ is $R^4$-1, $R^5$ is $R^5$-3, $R^6$ is $R^6$-1, $R^7$ is $R^7$-2 and A is O, preferably $R^1$ is $R^1$-1, $R^2$ is $R^2$-1, $R^3$ is $R^3$-1, $R^4$ is $R^4$-1, $R^5$ is $R^5$-2, $R^6$ is $R^6$-1, $R^7$ is $R^7$-3 and A is O, preferably $R^1$ is $R^1$-1, $R^2$ is $R^2$-1, $R^3$ is $R^3$-1, $R^4$ is $R^4$-1, $R^5$ is $R^5$-3, $R^6$ is $R^6$-1, $R^7$ is $R^7$-3 and A is O,

(16) a compound wherein $R^1$ is $R^1$-1, $R^2$ is $R^2$-1, $R^3$ is $R^3$-1, $R^4$ is $R^4$-1, $R^5$ is $R^5$-1, $R^6$ is $R^6$-2, $R^7$ is $R^7$-2 and A is O, preferably $R^1$ is $R^1$-1, $R^2$ is $R^2$-1, $R^3$ is $R^3$-1, $R^4$ is $R^4$-1, $R^5$ is $R^5$-1, $R^6$ is $R^6$-2, $R^7$ is $R^7$-3 and A is O,

(17) a compound wherein $R^1$ is $R^1$-1, $R^2$ is $R^2$-1, $R^3$ is $R^3$-1, $R^4$ is $R^4$-1, $R^5$ is $R^5$-2, $R^6$ is $R^6$-2, $R^7$ is $R^7$-2 and A is O, preferably $R^1$ is -1, $R^2$ is $R^2$-1, $R^3$ is $R^3$-1, $R^4$ is $R^4$-1, $R^5$ is $R^5$-2, $R^6$ is $R^6$-2, $R^7$ is $R^7$-3 and A is O, preferably $R^1$ is $R^1$-1, $R^2$ is $R^2$-1, $R^3$ is $R^3$-1, $R^4$ is $R^4$-1, $R^5$ is $R^5$-3, $R^6$ is $R^6$-2, $R^7$ is $R^7$-2 and A is O, preferably $R^1$ is $R^1$-1, $R^2$ is $R^2$-1, $R^3$ is $R^3$-1, $R^4$ is $R^4$-1, $R^5$ is $R^5$-3, $R^6$ is $R^6$-2, $R^7$ is $R^7$-3 and A is O,

(18) a compound wherein $R^1$ is $R^1$-2, $R^2$ is $R^2$-2, $R^3$ is $R^3$-2, $R^4$ is $R^4$-2, $R^5$ is $R^5$-1, $R^6$ is $R^6$-1, $R^7$ is $R^7$-1 and A is O, preferably $R^1$ is $R^1$-2, $R^2$ is $R^2$-2, $R^3$ is $R^3$-2, $R^4$ is $R^4$-2, $R^5$ is $R^5$-2, $R^6$ is $R^6$-1, $R^7$ is $R^7$-1 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-1, $R^7$ is $R^7$-1 and A is O,

(19) a compound wherein $R^1$ is $R^1$-2, $R^2$ is $R^2$-2, $R^3$ is $R^3$-2, $R^4$ is $R^4$-2, $R^5$ is $R^5$-1, $R^6$ is $R^6$-2, $R^7$ is $R^7$-1 and A is O,

(20) a compound wherein $R^1$ is $R^1$-2, $R^2$ is $R^2$-2, $R^3$ is $R^3$-2, $R^4$ is $R^4$-2, $R^5$ is $R^5$-1, $R^6$ is $R^6$-1, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-1, $R^6$ is $R^6$-1, $R^7$ is $R^7$-3 and A is O,

(21) a compound wherein $R^1$ is $R^1$-2, $R^2$ is $R^2$-2, $R^3$ is $R^3$-2, $R^4$ is $R^4$-2, $R^5$ is $R^5$-2, $R^6$ is $R^6$-2, $R^7$ is $R^7$-1 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-2, $R^7$ is $R^7$-1 and A is O,

(22) a compound wherein $R^1$ is $R^1$-2, $R^2$ is $R^2$-2, $R^3$ is $R^3$-2, $R^4$ is $R^4$-2, $R^5$ is $R^5$-2, $R^6$ is $R^6$-1, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-1, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-2, $R^6$ is $R^6$-1, $R^7$ is $R^7$-3 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-1, $R^7$ is $R^7$-3 and A is O,

(23) a compound wherein $R^1$ is $R^1$-2, $R^2$ is $R^2$-2, $R^3$ is $R^3$-2, $R^4$ is $R^4$-2, $R^5$ is $R^5$-1, $R^6$ is $R^6$-2, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-1, $R^6$ is $R^6$-2, $R^7$ is $R^7$-3 and A is O,

(24) a compound wherein $R^1$ is $R^1$-2, $R^2$ is $R^2$-2, $R^3$ is $R^3$-2, $R^4$ is $R^4$-2, $R^5$ is $R^5$-2, $R^6$ is $R^6$-2, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-2, $R^6$ is $R^6$-2, $R^7$ is $R^7$-3 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-2, $R^7$ is $R^7$-2 and A is O, preferably $R^1$ is $R^1$-2, $R^2$ is $R^2$-2, $R^3$ is $R^3$-2, $R^4$ is $R^4$-2, $R^5$ is $R^5$-3, $R^6$ is $R^6$-2, $R^7$ is $R^7$-3 and A is O,

(25) a compound wherein $R^1$ is $R^1$-3, $R^2$ is $R^2$-3, $R^3$ is $R^3$-3, $R^4$ is $R^4$-3, $R^5$ is $R^5$-1, $R^6$ is $R^6$-1, $R^7$ is $R^7$-1 and A is O, preferably $R^1$ is $R^1$-3, $R^2$ is $R^2$-3, $R^3$ is $R^3$-3, $R^4$ is $R^4$-3, $R^5$ is $R^5$-2, $R^6$ is $R^6$-1, $R^7$ is $R^7$-1 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-1, $R^7$ is $R^7$-1and A is O,

(26) a compound wherein $R^1$ is $R^1$-3, $R^2$ is $R^2$-3, $R^3$ is $R^3$-3, $R^4$ is $R^4$-3, $R^5$ is $R^5$-1, $R^6$ is $R^6$-2, $R^7$ is $R^7$-1 and A is O,

(27) a compound wherein $R^1$ is $R^1$-3, $R^2$ is $R^2$-3, $R^3$ is $R^3$-3, $R^4$ is $R^4$-3, $R^5$ is $R^5$-1, $R^6$ is $R^6$-1, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-1, $R^6$ is $R^6$-1, $R^7$ is $R^7$-3 and A is O,

(28) a compound wherein $R^1$ is $R^1$-3, $R^2$ is $R^2$-3, $R^3$ is $R^3$-3, $R^4$ is $R^4$-3, $R^5$ is $R^5$-2, $R^6$ is $R^6$-2, $R^7$ is $R^7$-1 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-1 and A is O,

(29) a compound wherein $R^1$ is $R^1$-3, $R^2$ is $R^2$-3, $R^3$ is $R^3$-3, $R^4$ is $R^4$-3, $R^5$ is $R^5$-2, $R^6$ is $R^6$-1, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-1, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-2, $R^6$ is $R^6$-1, $R^7$ is $R^7$-3 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-1, $R^7$ is $R^7$-3 and A is O,

(30) a compound wherein $R^1$ is $R^1$-3, $R^2$ is $R^2$-3, $R^3$ is $R^3$-3, $R^4$ is $R^4$-3, $R^5$ is $R^5$-1, $R^6$ is $R^6$-2, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-1, $R^6$ is $R^6$-2, $R^7$ is $R^7$-3 and A is O,

(31) a compound wherein $R^1$ is $R^1$-3, $R^2$ is $R^2$-3, $R^3$ is $R^3$-3, $R^4$ is $R^4$-3, $R^5$ is $R^5$-2, $R^6$ is $R^6$-2, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-2, $R^6$ is $R^6$-2, $R^7$ is $R^7$-3 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-2 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-3 and A is O, preferably $R^1$ is $R^1$-3, $R^2$ is $R^2$-3, $R^3$ is $R^3$-3, $R^4$ is $R^4$-3, $R^5$ is $R^5$-4, $R^6$ is $R^6$-2, $R^7$ is $R^7$-3 and A is O, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-4 and A is O, preferably $R^1$ is $R^1$-3, $R^2$ is $R^2$-3, $R^3$ is $R^3$-3, $R^4$ is $R^4$-3, $R^5$ is $R^5$-4, $R^6$ is $R^6$-2, $R^7$ is $R^7$-4 and A is O,

(32) a compound wherein $R^1$ is $R^1$-3, $R^2$ is $R^2$-3, $R^3$ is $R^3$-3, $R^4$ is $R^4$-3, $R^5$ is $R^5$-2, $R^6$ is $R^6$-2, $R^7$ is $R^7$-2, A is O and a broken line represents a bond, preferably $R^1$ is $R^1$-3, $R^2$ is $R^2$-3, $R^3$ is $R^3$-3, $R^4$ is $R^4$-3, $R^5$ is $R^5$-2, $R^6$ is $R^6$-2, $R^7$ is $R^7$-3, A is O and a broken line represents a bond, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-2, A is O and a broken line represents a bond, preferably $R^1$ is $R^1$-3, $R^2$ is $R^2$-3, $R^3$ is $R^3$-3, $R^4$ is $R^4$-3, $R^5$ is $R^5$-3, $R^6$ is $R^6$-2, $R^7$ is $R^7$-3, A is O and a broken line represents a bond,

(33) a compound wherein $R^1$ is hydrogen, $R^2$ is optionally substituted alkoxy, both of $R^3$ and $R^4$ are hydrogens, $R^5$ is benzo[1,3]dioxol-5-yl, $R^6$ is hydrogen, $R^7$ is hydrogen, halogen, optionally substituted alkoxy, thienyl, optionally substituted amino or optionally substituted alkylthio, A is O or S and a broken line represents a bond, pharmaceutically acceptable salts or hydrates thereof Another preferable embodiments is, in the formula (I'), (1) a compound wherein $Ar^1$ and $Ar^2$ are each independently optionally substituted phenyl, optionally substituted phenyloxy or optionally substituted thienyl, preferably $Ar^1$ and $Ar^2$ are each independently phenyl, phenyloxy or thienyl optionally substituted with one to three substituents selected from the group consisting of optionally substituted alkyl, optionally substituted alkoxy, halogen, alkylenedioxy and optionally substituted amino, more preferably $Ar^1$ and $Ar^2$ are each independently phenyl, phenyloxy or thienyl optionally substituted with I to 3 substituents selected from the group consisting of alkyl, alkoxy, halogen, alkylenedioxy, optionally substituted amino and carboxyalkoxy, most preferably $Ar^1$ is phenyl or phenyloxy optionally substituted with 1 to 3 substituents selected from the group consisting of alkyl, alkoxy and alkylenedioxy and $Ar^2$ is phenyl optionally substituted with 1 to 3 substituents selected from the group consisting of alkyl, alkoxy and alkylenedioxy, (2) a compound wherein $R^{1'}$, $R^{2'}$, $R^{3'}$ and $R^{4'}$ are each independently hydrogen, optionally substituted alkyl, hydroxy or optionally substituted alkoxy, more preferably $R^{1'}$, $R^{2'}$, $R^{3'}$ and $R^{4'}$ are each independently hydrogen or optionally substituted alkoxy, most preferably $R^{1'}$, $R^{2'}$, $R^{3'}$ and $R^{4'}$ are each independently hydrogen or alkoxy, (3) a compound wherein $R^{1'}$, $R^{2'}$, $R^{3'}$ and $R^{4'}$ are each independently hydrogen, optionally substituted alkyl, hydroxy or optionally substituted alkoxy and $Ar^1$ and $Ar^2$ are each independently optionally substituted phenyl or phenyloxy, preferably $R^{1'}$, $R^{2'}$, $R^{3'}$ and $R^{4'}$ are each independently hydrogen or optionally substituted alkoxy and $Ar^1$ and $Ar^2$ are each independently phenyl or phenyloxy optionally substituted with 1 to 3 substituents selected from the group consisting of alkyl, alkylenedioxy and alkoxy, more preferably $R^{1'}$, $R^{3'}$ and $R^{4'}$ are hydrogen, $R^{2'}$ is hydrogen or optionally substituted alkoxy and $Ar^1$ and $Ar^2$ are each independently phenyl substituted with 1 to 3 substituents selected from the group consisting of alkyl, alkylenedioxy and alkoxy, most preferably $R^{1'}$, $R^{3'}$ and $R^{4'}$ are hydrogen, $R^{2'}$ is hydrogen or optionally substituted alkoxy, $Ar^1$ is phenyl or phenyloxy substituted with 1 to 3 substituents selected from the group consisting of alkyl, alkylenedioxy and alkoxy and $Ar^2$ is phenyl substituted with 1 to 3 substituents selected from the group consisting of alkyl, alkylenedioxy and alkoxy, pharmaceutically acceptable salts and hydrates thereof.

A compound of the following formula (III):

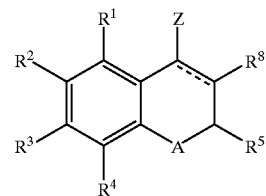

(III)

wherein $R^1$, $R^2$, $R^3$ and $R^4$ are each independently hydrogen, optionally substituted alkyl, optionally substituted alkenyl, optionally substituted alkynyl, optionally substituted cycloalkyl, hydroxy, halogen, optionally substituted alkoxy, optionally substituted alkenyloxy, optionally substituted alkynyloxy, optionally substituted cycloalkoxy, optionally substituted acyloxy, nitro or optionally substituted amino, $R^5$ is optionally substituted alkyl, optionally substituted alkenyl, optionally substituted alkynyl, optionally substituted aryl, optionally substituted heterocyclic or optionally substituted cycloalkyl, $R^8$ is formyl carboxy, optionally substituted alkoxycarbonyl or optionally substituted aryloxycarbonyl, Z is halogen, hydroxy, optionally substituted alkoxy, optionally substituted alkenyloxy, optionally substituted alkynyloxy, optionally substituted alkylsulfonyloxy or optionally substituted arylsulfonyloxy, A is S or O, and a broken line represents presence or absence of a bond can be used as intermediates of the above compounds (I).

In the formula (III), preferable embodiments are (1) a compound wherein $R^1$, $R^2$, $R^3$ and $R^4$ are each independently hydrogen, optionally substituted alkyl, optionally substituted alkenyl, optionally substituted alkynyl, optionally substituted cycloalkyl hydroxy, halogen, optionally substituted alkoxy, optionally substituted alkenyloxy, optionally substituted alkynyloxy, optionally substituted cycloalkoxy, optionally substituted acyloxy, nitro or optionally substituted amino, $R^5$ is optionally substituted alkyl, optionally substituted alkenyl, optionally substituted alkynyl, optionally substituted aryl, optionally substituted heterocyclic or optionally substituted cycloalkyl, $R^8$ is formyl, carboxy, optionally substituted alkoxycarbonyl or optionally substituted aryloxycarbonyl and Z is halogen, hydroxy, optionally substituted alkoxy, optionally substituted alkenyloxy, optionally substituted alkynyloxy, optionally substituted alkylsulfonyloxy or optionally substituted arylsulfonyloxy, (2) a compound wherein $R^1$ to $R^4$ are each independently hydrogen, optionally substituted alkyl, hydroxy, optionally substituted alkoxy or optionally substituted cycloalkoxy, $R^5$ is optionally substituted alkyl, optionally substituted alkenyl, optionally substituted aryl or optionally substituted heterocyclic, $R^8$ is formyl, carboxyl or optionally substituted alkoxycarbonyl and Z is halogen, hydroxy, optionally substituted alkoxy, optionally substituted alkenyloxy, optionally substituted alkynyloxy, optionally substituted alkylsulfonyloxy or optionally substituted arylsulfonyloxy, (3) a compound wherein $R^1$–$R^4$ are each independently hydrogen or optionally substituted alkoxy, $R^5$ is optionally substituted alkyl or optionally substituted aryl, $R^8$ is formyl carboxyl or alkoxycarbonyl, Z is halogen or optionally substituted alkoxy and A is O, (4) a compound wherein $R^1$, $R^3$ and $R^4$ is hydrogen, $R^2$ is optionally substituted alkoxy, $R^5$ is benzo[1,3]dioxol-5-yl, $R^8$ is formyl, carboxyl or alkoxycarbonyl, Z is halogen or alkoxy, A is O and a broken line represents a bond, (5) a compound wherein $R^1$, $R^3$ and $R^4$ is hydrogen, $R^2$ is optionally substituted lower alkoxy, $R^5$ is benzo[1,3]dioxol-5-yl, $R^8$ is formyl, carboxyl or lower alkoxycarbonyl, Z is halogen or lower alkoxy, A is O and a broken line represents a bond, (6) a compound wherein $R^1$, $R^3$ and $R^4$ is hydrogen, $R^2$ is isopropyloxy, $R^5$ is benzo[1,3]dioxol-5-yl, $R^8$ is formyl, carboxyl or lower alkoxycarbonyl, Z is halogen or lower alkoxy, A is O and a broken line represents a bond, (7) a compound wherein $R^1$, $R^2$, $R^3$ and $R^4$ are each independently hydrogen, optionally substituted alkyl, optionally substituted alkenyl, optionally substituted alkynyl, optionally substituted cycloalkyl, hydroxy, halogen, optionally substituted alkoxy, optionally substituted alkenyloxy, optionally substituted alkynyloxy, optionally substituted cycloalkoxy, optionally substituted acyloxy, nitro or optionally substituted amino, $R^5$ is optionally substituted alkyl, optionally substituted alkenyl, optionally substituted alkynyl, optionally substituted aryl, optionally substituted heterocyclic or optionally substituted cycloalkyl, $R^8$ is formyl, carboxy, optionally substituted alkoxycarbonyl or optionally substituted aryloxycarbonyl and Z is hydroxy, optionally substituted alkenyloxy, optionally substituted alkynyloxy, optionally substituted alkylsulfonyloxy or optionally substituted arylsulfonyloxy, (8) a compound wherein $R^1$–$R^4$ are each independently hydrogen or optionally substituted alkoxy, $R^5$ is optionally substituted alkyl or optionally substituted aryl, $R^8$ is formyl, carboxyl or alkoxycarbonyl, Z is hydroxy, optionally substituted alkenyloxy, optionally substituted alkynyloxy, optionally substituted alkylsulfonyloxy or optionally substituted arylsulfonyloxy and A is O, and (9) a compound wherein $R^1$, $R^3$ and $R^4$ are hydrogen, $R^2$ is optionally substituted alkoxy, $R^5$ is benzo[1,3]dioxol-5-yl, $R^8$ is formyl, carboxyl or alkoxycarbonyl, Z is hydroxy, optionally substituted alkenyloxy, optionally substituted alkynyloxy, optionally substituted alkylsulfonyloxy or optionally substituted arylsulfonyloxy, A is O and a broken line represents a bond.

In the present specification, the term "alkyl" means straight or branched chain alkyl having 1 to 10 carbon atoms, preferably 1 to 8 carbon atoms, more preferably 1 to 6 carbon atoms and most preferably 1 to 4 carbon atoms. The examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, nonyl, decyl and the like.

The "optionally substituted alkyl" may have one or more substituents such as halogen, hydroxy, cyano, cycloalkyl, carboxy, optionally substituted alkoxy (examples of the substituents are cycloalkyl, heterocyclic optionally substituted with alkyl or the like, hydroxy, cyano, alkoxy, acyl, amino, alkylamino, carboxy, optionally substituted aryl wherein the substituents include alkyl, alkoxy, carboxyalkoxy, alkylenedioxy, halogen, amino, alkylamino, carboxy, alkoxycarbonyl, acyl or the like, etc.), acyl, alkylenedioxy such as methylenedioxy, ethylenedioxy or the like, optionally substituted amino (an example of the substituent is alkyl, i.e., examples of the substituted amino are dimethylamino, diethylamino and the like), optionally substituted aryl (examples of the substituents are alkyl, alkoxy, carboxyalkoxy, alkylenedioxy, halogen, amino, alkylamino, carboxy, alkoxycarbonyl, acyl and the like) and optionally substituted heterocyclic (examples of the substituents are alkyl, alkoxy, carboxyalkoxy, alkylenedioxy, halogen, amino, alkylamino, carboxy, alkoxycarbonyl, acyl and the like) at any possible positions. As substituted alkyl exemplified are cycloalkylalkyl such as cyclopropylmethyl, cyclobutylethyl and the like, haloalkyl such as chloromethyl, trifluoromethyl and the like, arylalkyl such as methoxyphenylalkyl and the like, alkoxyarylalkyl such as methoxybenzyl and the like, alkoxyalkyl such as methoxypropyl and the like, cycloalkylalkyl such as cyclohexylmethyl and the like, hydroxyalkyl such as hydroxybutyl and the like, aldehydoalkyl such as formylpropyl and the like.

The alkyl parts of "alkylthio", "optionally substituted alkylthio", "alkylamino", "haloalkyl", "arylalkyl", "alkylsulfonyloxy" and "cycloalkylalkyl" are the same as defined above.

The alkyl parts of "alkoxy" is the same as the above alkyl and examples of alkoxy include methoxy, ethoxy, n-propoxy, 2-methylpropoxy, 1-ethylpropoxy, isopropoxy, n-butoxy, sec-butoxy, tert-butoxy, 2-ethylbutoxy, 3-methylbutoxy, 3,3-dimethylbutoxy, 1-propylbutoxy, n-pentyloxy, isopentyloxy, 4-methylpentyloxy, n-hexyloxy, n-heptyloxy, n-octyloxy, n-nonyloxy, n-decyloxy and the like. Otherwise mentioned "lower alkoxy" means alkoxy having 1–4 carbon atoms.

Substituents for "optionally substituted alkoxy" are the same as those for the above alkyl and the examples of the substituted alkoxy include cyclopropylmethoxy, 2-cyclopropylethoxy, benzyloxy, dimethylaminoethoxy, formylethoxy, formylpropoxy, hydroxypentyloxy, dihydroxyethoxy, dimethoxybutoxy, diethoxyethoxy, cyanopropyloxy, 4-methoxyphenylethoxy and the like.

The alkoxy part of "alkoxycarbonyl" and the alkoxy part and substituents for "optionally substituted alkoxycarbonyl" are the same as those for the defined above. Otherwise mentioned, "lower alkoxycarbonyl" means alkoxycarbonyl wherein the alkyl part has 1–4 carbon atoms.

The alkoxy part and substituents for "optionally substituted alkoxycarbonyl" and the alkoxy part of "carboxyalkoxy" are the same as the above alkoxy.

The term "alkylenedioxy" means alkylenedioxy having 1–3 carbon atoms and exemplified are methylenedioxy, ethylenedioxy, propylenedioxy and the like.

The term "alkenyl" means a straight or branched chain alkenyl having 2–10 carbon atoms, preferably 2–8 carbon atoms and more preferably 2–6 carbon atoms. For example, vinyl, propenyl, isopropenyl, butenyl, pentenyl, hexenyl, heptenyl, octenyl, nonenyl, decenyl and the like are exemplified. These have one or more double bonds at any possible positions. Substituents for "optionally substituted alkenyl" are the same as those for the above alkyl.

The alkenyl part of "alkenyloxy" and "alkenylthio" and the alkenyl part and substituents for "optionally substituted alkenyloxy" and "optionally substituted alkenylthio" are the same as the above alkenyl.

The term "alkynyl" means a straight or branched chain alkynyl having 2–10 carbon atoms, preferably 2–8 carbon atoms and more preferably 2–6 carbon atoms. Examples are ethynyl, propynyl, butynyl, pentynyl, hexynyl heptynyl, octynyl, nonyl, decynyl and the like. These have one or more triple bonds at any possible positions and may have an additional double bond. Substituents for optionally substituted alkynyl" are the same as those for the above alkyl.

The alkynyl part of "alkynyloxy" and "alkynylthio" and the alkynyl part and substituents for "optionally substituted alkynyloxy" and "optionally substituted alkynylthio" are the same as the above alkynyl.

The term "cycloalkyl" means a cyclic alkyl having 3–7 carbon atoms, preferably 3–6 carbon atoms, more preferably 3–5 carbon atoms and exemplified are cyclopropyl, cyclobutyl, cyclopentyl, cyclohexyl, cycloheptyl and the like. As substituents for "optionally substituted cycloalkyl" are exemplified the substituents for the above alkyl, alkyl, alkenyl and the like.

The cycloalkyl part of "cycloalkylalkyl" is the same as defined above.

The cycloalkyl part of "cycloalkoxy" is the same as defined above and examples of cycloalkoxy include cyclopropoxy, cyclobutoxy, cyclopentyloxy and the like. Substituents for "optionally substituted cycloalkoxy" are the same as the above cycloalkyl.

The term "halogen" means fluorine, chlorine, bromine and iodine. The halogen part of "haloalkyl" are the same as these.

The term "acyl" means a straight or branched chain acyl having 1–10 carbon atoms, preferably 1–8 carbon atoms, more preferably 1–6 carbon atoms which are derived from aliphatic carboxylic acids and the examples include formyl, acetyl, propionyl, butyryl, isobutyryl, valeryl, pivaloyl, hexanoyl and the like. Substituents for "optionally substituted acyl" are the same as those for the above alkyl.

The acyl part of "acyloxy" is the same as the above acyl and examples include formyloxy, acetyloxy, propionyloxy, butyryloxy, valeryloxy, pivaloyloxy, hexanoyloxy and the like. Substituents for "optionally substituted acyloxy" are the same as those for the above alkyl.

The term "optionally substituted amino" includes unsubstituted amino and substituted amino. Examples of the substituted amino include mono- or di-substituted amino such as alkylamino (methylamino, ethylamino etc.), dialkylamino (dimethylamino, diethylamino etc.), cycloalkylamino (cyclohexylamino etc.), phenylamino, diphenylamino, acylamino (acetylamino etc.), and the like and cyclic amino such as piperidino, piperadino, morpholino and the like.

The term "aryl" means a monocyclic group or a fused ring group having 6–14 carbon atoms, preferably 6–10 carbon atoms. Phenyl, naphthyl such as 1-naphthyl and 2-naphthyl, anthryl such as 1-anthryl and 2-anthryl, indanyl such as 1-indanyl and 6-indanyl, indenyl such as 1-indenyl and 7-indenyl, phenanthryl such as 1-phenanthryl and 2-phenanthryl etc. are exemplified. Phenyl is specifically preferable.

As substituents for "optionally substituted aryl" exemplified are the same as those for the above alkyl, alkyl, alkenyl and the like. Examples of the substituted aryl are 2-, 3- or 4-methoxyphenyl, 2,4- or 3,4-dimethoxyphenyl, 3,4,5-trimethoxyphenyl, 4-chlorophenyl, 3-or 4-fluorophenyl, 3,4-difluorophenyl, 4-methylphenyl, 4-propylphenyL 4-isopropylphenyl, 4-dimethylaminophenyL 2-carboxymethoxy-4-methoxyphenyl, 3,4-methylenedioxyphenyl, 3,4-ethylenedioxyphenyl and the like.

The aryl part of "aryloxy", "arylalkyl" and "arylsulfonyloxy" and the aryl part and substituents for "optionally substituted aryloxy" are the same as the above aryl.

The term "heterocyclic" means a saturated or unsaturated 3- to 7-membered ring, preferably 5- to 7-membered ring containing discretionally selected one or more of oxygen, sulfur and/or nitrogen atoms, and also they may be condensed with a carbocyclic ring or a heterocyclic ring. These heterocyclic ring may bond with substituents at any possible positions. Examples include non-aromatic heterocyclic groups such as oxiranyl, dioxanyl thiiranyl, dioxolanyl, oxathiolanyl, azethidinyl, pyrrolidinyl, pyrrolinyl, imidazolidinyl, imidazolinyl, pyrazolidinyl, pyrazolinyl, piperidinyl, piperazinyl, morpholinyl, dihydrobenzofuryl (for example, 2,3-dihydro-5-benzofuryl and 2,3-dihydro-6-benzofuryl) and the like, and heteroaryls such as pyrrolyl such as 1-pyrrolyl, indolyl such as 2- or 6-indolyl, carbazolyl such as 3-carbazolyl, imidazolyl such as 1-imidazolyl, pyrazolyl such as 3-pyrazolyl, benzimidazolyl such as 2-benzimidazolyl, indazolyl such as 3-indazolyl, pyridyl such as 3-pyridyl and 4-pyridyl, quinolyl such as 8-quinolyl, isoquinolyl such as 3-isoquinolyl, pyrimidinyl such as 4-pyrimidinyl, pyrazinyl such as 2-pyrazinyl, isoxazolyl such as 4-isoxazolyl, oxazolyl such as 2-oxazolyl, furyl such as $^2$-furyl, benzofuryl such as 3-, 4-, 5- or 6-benzofuryl, thienyl such as 2-thienyl, benzothienyl such as 1-benzothiophen-2-yl and 2-benzothiophen-1-yl and the like. Substituents for "optionally substituted heterocyclic" and "optionally substituted heteroaryl" are, for example, those for the above alkyl, alkyl, alkenyl and the like.

The heterocyclic part of "heterocyclooxy" and the heterocyclic part and substituents for "optionally substituted heterocyclooxy" are the same as the above.

The compound group (I) also includes pharmaceutically acceptable salts and hydrates thereof Alkaline metal salts such as lithium, sodium, potassium and the like, salts with alkaline earth metals such as calcium, magnesium and the like, salts with ammonium, salts with organic bases such as triethylamine, pyridine and the like, salts with amino acids, salts with mineral acids such as hydrogen chloride, sulfuric acid, nitric acid and the like, salts with organic acids such as citric acid, para toluenesulfonic acid, methanesulfonic acid, and the like are exemplified as "the pharmaceutically acceptable salts". These salts may be prepared by usual method. The arbitrary number of water molecules may hydrate to one molecule of a compound selected from the compound group (I).

Corresponding racemates, both of enantiomers and all of possible stereoisomers such as diastereomer, epimer, enantiomer and the like are also included in the compound group (I).

The term "endothelin antagonist" includes all of compounds which has an endothelin receptor antagonistic activity. Typical examples are the compound group (I), triterpene derivatives of the following formula:

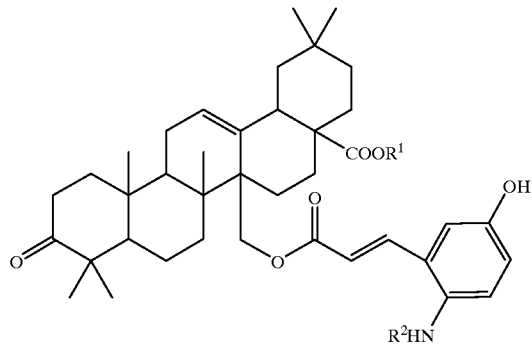

wherein $R^1$ is hydrogen or a metabolizable ester residue; $R^2$ is hydrogen or $-R^3-R^4$ wherein $R^3$ is $-SO_3-$, $-CH_2COO-$, $-COCOO-$, or $-COR^5COO-$ wherein $R^5$ is alkylene having 1 to 6 carbon atoms or alkenylene having 2 to 6 carbon atoms, and $R^4$ is hydrogen or alkyl having 1 to 6 carbon atoms (WO 92/12991, JP-A 7-53484 ), bosentan (4-tert-butyl-N-[6-(2-hydroxyethoxy)-5-(2-methoxyphenoxy)-[2,2'-bipyrimidinyl-4-yl]-benzenesulfonamide; British Journal of Pharmacology, November 1994, 113 (3), p. 845–852), (1S,2R,3S)-3-(2-carboxymethoxy-4-methoxyphenyl)-1-(3,4-methylenedioxyphenyl)-5-(prop-1-yloxy)indane-2-carboxylic acid (SB-209670; Biochemistry, December 1994, 33 (48), p. 14543–14549), (−)-N-(4-isopropylbenzenesulfonyl)-α-(4-carboxy-2-n-propylphenoxy)-3,4-methylenedioxyphenylacetamide (L-754142; The Journal of Pharmacology and Experimental Therapeutics, 1995, 275 (3), p. 1518–1526), cyclo[D-Asp-L-Pro-D-Val-L-Leu-D-Trp-] (BQ-123; Life Science, 1992, 50, p. 247–255), 2(R)-[2(R)-[2(S)[[1-(hexahydro-1H-azepinyl)]carbonyl]amino-4-methylpentanoyl]amino-3-[3-(1-methyl-1H-indolyl)]propionyl]amino-3-(2-pyridyl) propionic acid (FR-139317; Pharmacology, 1994, 49 (5), p. 319–324), cyclo[D-aspartyl-L-[3-(4-phenylpiperazin-1-ylcarbonyl)]-alanyl-L-aspartyl-D-[2-(2-thienyl)]glycyl-L-leucyl-D-tryptophyl].2Na (TAK-044; Life Science, 1994, 55 (4), p. 301–310), α-12-(4-methoxyphenyl)-2-oxo-1-[(3,4,5-trimethoxyphenyl)methyl]ethylidene-1,3-benzodioxol-5-acetic acid sodium salt (PD156707; WO 95/05376), (N-(4-chloro-3-methylisoxazol-5-yl)-2-[2-(6-methyl-1,3-benzodioxol-5-yl)acetyl]thiophen-3-sulfonamide (TBC-11251, U.S. Pat. No. 5,464,853), (1S-(α,2β,3α))-1-(1,3-benzodioxol-5-yl)-2,3-dihydro-3-(2-(2-hydroxyethoxy)-4-methoxyphenyl)- 5-propoxy-(1H-indene)-2-carboxylic acid (SB-217242), (2R)-N-acetyl-2-(10,11-dihydro-5H-dibenzo[a,d]cyclohepten-5-yl)glycyl-L-leucyl-L-α-aspartyl-L-isoleucyl-L-isoleucyl-L-tryptophan disodium salt (PD 145065), [2S-(2α,3β,4α)]-4-(1,3-benzodioxol-5-yl)-1-12-(dibutylamino)-2-oxoethyl]-2-(4-methoxyphenyl)-3-pyrrolidine carboxylic acid (A-127722), (2R-cis)-N-[N-[(2,6-dimethyl-1-piperidinyl)carbonyl]-4-methyl-L-leucyl]-1-(methoxycarbonyl)-D-tryptophyl]-D-norleucine monosodium salt (BQ-788) Exp. Opin. Invest. Drugs (1997) 6 (5):475–487) and the like. The compounds (Iα) are preferable and the compound (I) is more preferable and the compounds (I') are specifically preferable.

The compound () can be synthesized, for example, via a key intermediate, a compound (III) or (IV) prepared by the following method A, B, C, D or E. A suitable combination of Z and $R^8$ for the compounds (III) can discretionally be selected according as various conditions which are necessary for a synthesis of the compound of the present invention. Some examples of the combinations are illustrated as follows but the combinations are generally discretional and ones which are not described below are also applicable as a person skilled in the art can easily understand.

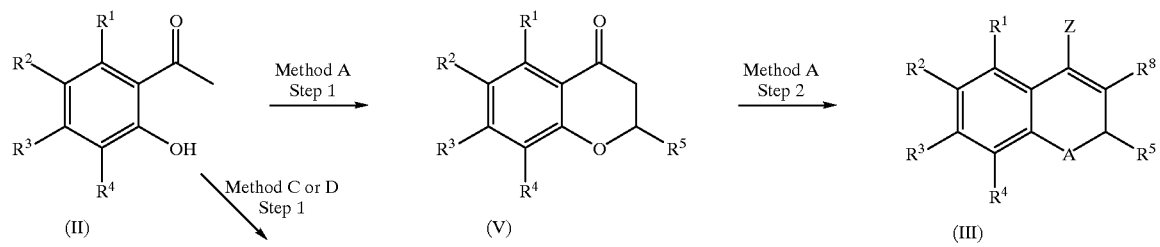

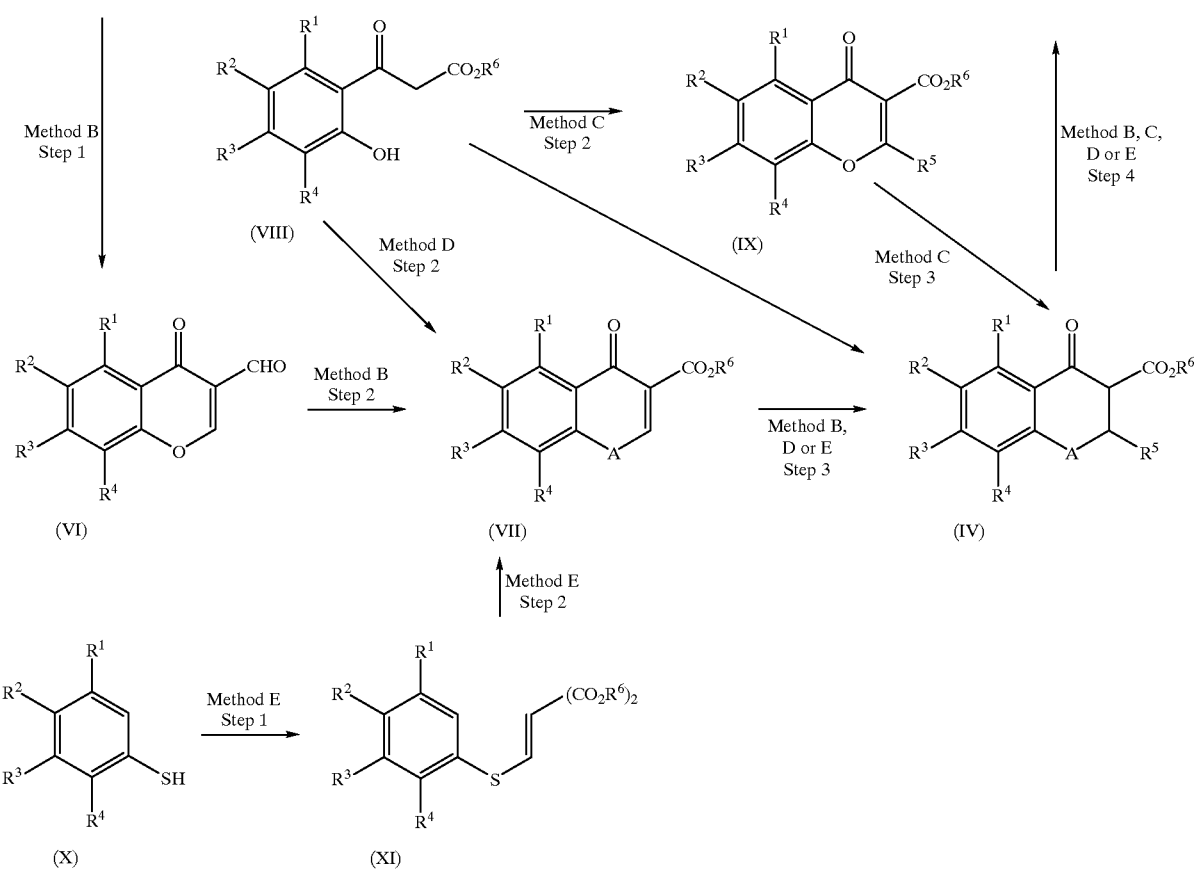

wherein $R^1$–$R^6$ and A is the same as defined above, $R^8$ is formyl, carboxy, optionally substituted alkoxycarbonyl or optionally substituted aryloxycarbonyl, Z is halogen, hydroxy, optionally substituted alkoxy, optionally substituted alkenyloxy, optionally substituted alkynyloxy, optionally substituted alkylsulfonyloxy or optionally substituted arylsulfonyloxy.

[Method A] (II→V→III; Z=halogen or optionally substituted alkoxy, A=O)

In Step 1, one of the compound (II), used as the starting material, undergoes cyclization and introduction of $R^5$ at the same time to give chromanon (V) and, in Step 2, $R^8$ and a leaving group Z are introduced into the compound (V).

(Method A, Step 1)(II→V)

This step can be carried out by a method described in J. Org. Chem., 1970, 35(7), 2286. Condensation of one of the compound (II) and an aldehyde $R^5$—CHO in the presence of a base wherein $R^5$ is the same as defined above gives chromanon (V). An inorganic base such as sodium hydroxide, potassium hydroxide or sodium hydride or an organic base such as potassium t-butoxide or piperidine can be employed as a base. A lower alcohol such as methanol t-butanol or the like, an etheral solvent such as tetrahydrofuran, dioxane or the like, water, or mixture thereof can be used as a solvent.

The starting compounds (II) are either commercially available or otherwise can be prepared from commercially available compounds by a known method. Examples of the starting compound (II) are ortho-hydroxyacetophenone, 2',3'-dihydroxyacetophenone, 2',4'-dihydroxyacetophenone, 2',5'-dihydroxyacetophenone, 2', 6'-dihydroxyacetophenone, 2'-hydroxy-6'-propoxyacetophenone, 5'-cyclopropylmethyl-2'-hydroxyacetophenone, 5'-benzyloxy-2'-hydroxyacetophenone, 2'-hydroxy-5'-propoxyacetophenone, 2'-hydroxy-4'-propoxyacetophenone, 2'-hydroxy-3'-propoxyacetophenone, 2'-hydroxy-5'-isopropoxyacetophenone, 2'-hydroxy-5'-nitroacetophenone, 2'-hydroxy-3'-nitroacetophenone, 2'-hydroxy-5'-propoxy-3'-propylacetophenone, 2'-hydroxy-5'-isopropylacetophenone and the like.

(Method A, Step 2) (V→III)

This step is generally known as the Vilsmeier Reaction. When one of the compounds (V) is reacted with an N,N'-di-substituted formamide such as dimethylformamide and a chlorinating agent such as phosphorous oxychloride, thionyl chloride or the like, the corresponding intermediate (III) wherein Z is chlorine and $R^8$ is formyl can be obtained. When phosphorous oxybromide, thionyl bromide or the like is used instead of a chlorinating agent, the compound (III) wherein Z is bromine and $R^8$ is formyl can be obtained. This reaction may be carried out at −30° C. to 100° C.

The compounds (III) wherein Z is alkoxy and $R^8$ is formyl can be obtained by reacting the compound (III) obtained in the above process with an alkaline metal salt or alkaline earth metal salt of alcohols. The reaction may be casrried out in a solvent such as methanol, dimethylformamide, tetrahydrofuran, 1,4-dioxane or the like at room temperature to refluxing temperature of solvent.

Oxidation of the compound (III) wherein $R^8$ is formyl can give the compound (III) wherein $R^8$ is carboxy. Although the oxidation may be carried out under usual oxidization conditions of aldehydes, an oxidation with a chlorite salt is specifically preferable (Acta. Chem. Scand., 1973, 27 (3), 888–890). Examples of the oxidizing agents are sodium chlorite, potassium chlorite and the like and these are usually used in the presence of sulfamic acid, dimethylsulfoxide, hydrogen peroxide, 2-methyl-2-butene or the like. A buffer such as sodium dihyrogen phosphate or the like can be added if necessary. Dichloromethane, chloroform, dichloroethane, dimethylsulfoxide, acetone, acetonitrile, water or mixture thereof can be used as a solvent. The reaction is usually carried out at 0–40° C.

The compounds (III) wherein $R^8$ is an ester group can be prepared from a corresponding compounds (II) wherein $R^8$ is carboxy. Although an explanation about esterification is not necessary for a person skilled in the art, exemplified are a method wherein diazomethane is used, a method wherein one of the compounds (III) is refluxed in an alcohol in the presence of an acidic catalyst such as hydrogen chloride, sulfuric acid, para-toluene sulfonic acid or the like, a method wherein carboxyl of the compounds (II) is condensed with an alcohol in the presence of a dehydrating agent such as dicyclohexylcarbodiimide or the like and a basic catalyst such as dimethylaminopyridine, a method wherein carboxyl of the compound (III) is reacted with a halide in the presence of a base such as potassium carbonate in dimethylformamide, a method wherein one of the compound (III) is converted into the corresponding acid chloride using oxalyl chloride, thionyl chloride or the like, then reacted with an alcohol and the like.

[Method B] (II→VI→VII→IV→III; $R^8$=carboxy, optionally substituted alkoxycarbonyl or optionally substituted aryloxycarbonyl, A═O)

Step 1 is generally called as the Vilsmeier Reaction, in which a starting material, one of the compounds (II), is simultaneously cyclized and formylated to obtain the compound (VI). Step 2 is a process for oxidizing a formyl group of the compound (VI). In step 3, a substituent $R^5$ is introduced to the compound (VII) at the 2-position to obtain the compound (V). In Step 4, the carbonyl group of the compound (IV) is converted into a suitable leaving group Z.

(Method B, Step 1) (II→VI)

This step can be carried out by the method described in Tetrahedron, 1974, 30, 3553–3561. The compound (VI) can be obtained by reacting the compounds (II) with an N,N'-di-substituted formamide such as dimethylformamide in the presence of phosphorous oxychloride, thionyl chloride or the like for a few hours to several tens hours, preferably 3–24 hours. The starting compounds (II) are known compounds or compounds which can be synthesized from known compounds by a usual method. Examples of the starting compound (II) include ortho-hydroxyacetophenone, 2', 3'-dihydroxyacetophenone, 2', 4'-dihydroxyacetophenone, 2', 5'-dihydroxyacetophenone, 2', 6'-dihydroxyacetophenone, 2'-hydroxy-6'-propoxyacetophenone, 5'-cyclopropylmethyl-2'-hydroxyacetophenone, 5'-benzyloxy-2'-hydroxyacetophenone, 2'-hydroxy-5'-propoxyacetophenone, 2'-hydroxy-4'-propoxyacetophenone, 2'-hydroxy-3'-propoxyacetophenone, 2'-hydroxy-5'-isopropoxyacetophenone, 2'-hydroxy-5'-nitroacetophenone, 2'-hydroxy-3'-nitroacetophenone, 2'-hydroxy-5'-propoxy-3'-propylacetophenone, 2'-hydroxy-5'-isopropylacetophenone and the like.

(Method B, Step 2) (VI→VII)

In this step, an aldehyde compound (VI) is oxidized to a carboxyl compound (VII) wherein $R^6$ is hydrogen, followed by being converted into a corresponding ester derivative wherein $R^6$ is optionally substituted alkyl or optionally substituted aryl. The oxidation reaction may be carried out under usual conditions used for oxidizing aldehydes. Preferable examples are a method of light exposure with N-bromosuccinimide in carbon tetrachloride (Synth. Commun., 1980, 10, 889–890) and a method of oxidizing with a chlorite in the presence of a chlorine scavenger (Acta. Chem. Scand., 1973, 27 (3), 888–890). Among the oxidation with a chlorite, sodium chlorite, potassium chlorite or the like is available with a chlorine scavenger such as sulfamic acid, dimethylsulfoxide, hydrogen peroxide, 2-methyl-2-buten or the like. A buffer such as sodium dihydrogen phosphate may be added if needed. Dichloromethane, chloroform, dichloroethane, dimethylsulfoxide, acetone, acetonitrile, water or mixed solvent thereof can be used as a solvent. The reaction is usually carried out at 0–40° C. The esterification can be carried out by the method described in the above Step 2 of Method A.

(Method B, Step 3) (VII→IV)

Step 3 is a process wherein a substituent $R^5$ is introduced into 2-position of an ester compound (VII) and can be carried out by a similar method described in Org. Reaction, 1972, 19, 1. A Grignard Reagent $R^5MgX$ wherein $R^5$ is the same as defined above and X represents halogen is prepared by a standard method. Then, $R^5MgX$ is subjected to a 1,4-addition reaction with the compound (VII) in the presence of a copper catalyst such as copper iodide to obtain the compound (IV). Tetrahydrofuran or ether may be used as a solvent and tetrahydrofuran is preferable. Copper iodide (I), copper cyanide (I), copper bromide (I)-dimethylsulfide complex or the like can be used as a copper catalyst. The reaction may be usually carried out at room temperature to refluxing temperature of solvent. Because of keto-enol tautomerism of an ester group at 3-position and a carbonyl group at 4-position of the chromanone ring, the compound (II) gives a mixture of keto-enol tautomers, and, as a results, a mixture of stereoisomers as well. In the above scheme, only one of possible structures is shown for convenience. These mixture of isomers can be used without further isolation and purification in the following Step 4 of Method B and can also be used as intermediates for the synthesis of the compounds (1) in the following Methods a, b, c and d.

(Method B, Step 4) (IV→III)

In the present step, a leaving group Z is introduced into the 4-position of the compound (IV). Preferable examples of Z include halogen, optionally substituted alkoxy and optionally substituted alkylsulfonyloxy and more preferable examples include chlorine, methoxy and perfluoroalkylsulfonyloxy (trifluoromethanesulfonyloxy (hereinafter referred to as triflate) is preferable).

The reaction of the compound (V) wherein $R^6$ is optionally substituted alkyl or optionally substituted aryl with a sulfonating agent gives the compound (III) wherein Z is alkylsulfonyloxy or arylsulfonyloxy and $R^8$ is optionally substituted alkoxycarbonyl or optionally substituted aryloxycarbonyl.

For example, the compound (II) wherein Z is methanesulfonyloxy (hereinafter referred to as mesylate), para-tluenesulfonyloxy (hereinafter referred to as tosylate), triflate or perfluorobutanesulfonyloxy can be synthesized by reacting the compound (IV) with a sulfonyl chloride or sulfonic acid anhydride corresponding to an objective compound in a solvent such as dichloromethane, dimethylformamide, tetrahydrofuran or the like in the presence of a tertiary base such as pyridine, triethylamine, ethyldiisopropylamine or the like. The reaction may usually be carried out at 0° C. to room temperature.

The compound (III) wherein Z is triflate can also be obtained by reacting the compound (IV) and 2-[N,N'-bistrifluoromethanesulfonylamino]pyridine or N,N'-bis(trifluoromethanesulfonyl)aniline or the like in a solvent such as dimethylformamide, tetrahydrofuran or the like in the presence of a base such as sodium hydride, lithium diisopropylamide, lithium hexamethyldisilazane or the like. The reaction may usually be carried out at −78° C. to room temperature.

The compound (III) wherein Z is halogen and $R^8$ is optionally substituted alkoxycarbonyl or optionally substituted aryloxycarbonyl can be synthesized by the reaction of the compounds (V) with tetrahalogenomethane in the presence of triphenylphosphine. For example, the reaction of the compound (IV) with carbon tetrachloride gives the compounds (III) wherein Z is chlorine and $R^8$ is optionally substituted alkoxycarbonyl or optionally substituted aryloxycarbonyl. Chloroform, carbon tetrachloride, ether or the like is used as a solvent. The reaction may usually be carried out at room temperature to the reaction solvent-refluxing temperature.

The compound (III) wherein Z is optionally substituted alkoxy, optionally substituted alkenyloxy or optionally substituted alkynyloxy and $R^8$ is optionally substituted alkoxycarbonyl or optionally substituted aryloxycarbonyl can be synthesized by the reaction of the compounds (IV) with a diazo reagent such as diazomethane or by the reaction of the compound (IV) with a corresponding alcohol in the presence of triphenylphosphine or tributylphosphine and dialkylazodicarboxylate such as diethylazodicarboxylate or tetraalkylazodicarboxamide such as 1,1'-(azodicarbonyl)dipiperidine or N, N, N', N'-tetramethylazodicarboxamide (Mitsunobu Reaction). In the reaction with a diazo reagent, a lower alcohol such as ethanol and the like, acetone, ether, tetrahydrofuran or mixture thereof can be used as a reaction solvent. The reaction may usually be carried out at 0° C. to room temperature. The Mitsunobu Reaction is a method described in Synthesis, 1981, 1, 1. An etheral solvent such as tetrahydrofuran or the like, benzene, toluene or the like is used as a reaction solvent. The reaction may be carried out at −15° C. to room temperature.

The compound (III) wherein $R^8$ is optionally substituted alkoxycarbonyl or optionally substituted aryloxycarbonyl obtained by the above method, if necessary, can be converted by hydrolysis into a compound (III) wherein $R^8$ is carboxyl.

[Method C] (II→VIII→IX→IV→III or II→VIII→IV→III; $R^8$=carboxy, optionally substituted alkoxycarbonyl or optionally substituted aryloxycarbonyl, A=O) Step 1 is a process for converting starting materials, the compounds (II), to ketoester compounds (VIII). Step 2 is a process for condensing compounds (VIII) with a carboxylate halide $R^5COX$ wherein $R^5$ and X is the same as defined above or an aldehyde $R^5CHO$. Step 3 is a process for reducing an internal double bond of a ring of compound (IX) to give compound (IV). Step 4 is the same as Step 4 of Method B.

(Method C, Step 1) (II→VIII)

One of the compound (II) is reacted with a dialkyl carbonate or diaryl carbonate $(R^6O)_2CO$ wherein $R^6$ is optionally substituted alkyl or optionally substituted aryl in the presence of a base to obtain the corresonding keto-ester compound (VIII). The compounds (II) to be used can be the same as those described in Method A or B. Examples of the dialkyl carbonate include dimethylcarbonate, diethylcarbonate, dipropyl carbonate and the like and examples of diaryl carbonate include diphenyl carbonate and the like. Sodium hydride, potassium hydride, lithium hexamethyldisilazane or the like is used as a base. As a solvent, tetrahydrofuran or the like is usually used and in the case that a low-boiling point dialkyl carbonate is used as a reactant, it can also be used as a solvent. The reaction may usually be carried out at ice-bath temperature to solvent-refluuxing temperature.

Method C, Step 2) (VIII→IX or VIII→IV)

The present step can be carried out by the similar method as described in J. Org. Chem., 1984, 49(7), 1280–1282.

One of the compounds (VIII) is reacted with a magnesium pieces in the presence of ethanol to give the corresponding magnesium salt, which is then reacted with a carboxylate halide $R^5COX$ to give a compound (IX). Benzene, toluene or the like can be used as a solvent. The reaction may be carried out at room temperature to solvent-refluxing temperature.

The compound (VIII) and an aldehyde $R^5CHO$ wherein $R^5$ is the same as defined above are refluxed with a catalytic amount of acetic acid and an organic base, preferably piperidine, in an organic solvent, preferably toluene, with aziotropic removal of water to directly obtain a compound (V). In this case, the following Step 3 can be eliminated. Piperonal, 4-methoxybenzaldehyde, 4-isopropylbenzaldehyde or the like is representative as an aldehyde.

Method C, Step 3) (IX→IV)

To a reduction of the present step, catalytic reduction, a hydride reduction or the like may be applied. A noble metal catalyst such as platinum oxide, palladium retained in a carrier such as carbon and the like can be used as a catalyst of a catalytic reduction. Any of solvents usually used for a catalytic reduction can be used as a solvent and a lower alcohol acetic acid, an acetate ester, tetrahydrofuran or mixture thereof is preferable. The reaction may usually be carried out under atomospheric or pressurized pressure at room temperature to 50° C. The hydride reduction may be carried out under an acidic condition in a solvent such as a lower alcohol, tetrahydrofuran or the like with a reductant such as sodium borohydride, triethylsilane or the like, preferably sodium cyanoborohydride at 0° C. to room temperature for 30 minutes to 24 hours.

The compound (V) obtained can be converted into the compound (III) by the method in Step 4 of Method B.

[Method D] (II→VIII→VII→IV→III; $R^8$=carboxy, optionally substituted alkoxycarbonyl or optionally substituted aryloxycarbonyl, A=O)

Step 1 is the same as Step 1 of Method C and Step 2 is cyclization of the compounds (VIII) to give the compounds (VII). Steps 3 and 4 are the same as Steps 3 and 4 of Method B, respectively.

(Method D, Step 2)

The compound (VIII) is condensed with a formaldehyde equivalent such as dimethylformamide dialkylacetal or an orthoformate ester to obtain compounds (VII) wherein $R^6$ is optionally substituted alkyl or optionally substituted aryl. The reaction can be carried out in a solvent such as benzene, toluene, acetic anhydride or the like or without a solvent. The reaction temperature is usually at 0° C. to the solvent-refluxing temperature.

The thus-obtained compound (VII) can be converted into compounds (III) by the method described in the above Steps 3 and 4 of Method B.

[Method E] (X→XI→VII→IV→III; $R^8$=carboxy, optionally substituted alkoxycarbonyl or optionally substituted aryloxycarbonyl, A=S)

The compound (VII) wherein A is S can be synthesized by the known method described in WO91/11443 starting from a compound (X) obtained in a usual method. The compound (III) wherein A is S can be obtained by subjecting the compound (VII) to the similar reactions as Steps 3 and 4 of Method B.

The intermediate (III) or (IV) thus obtained can be converted into the compounds (I) of the present invention by the following Method a, b, c or d.

wherein X is the same as defined above can be used as $R^7$-M. A preferable method is the Suzuki Reaction using an organe boron compound. As a palladium catalyst, tetrakistriphenylphosphine palladium (0), bis(triphenylphosphine) palladium (II) chloride, palladium (II) acetate-triphenylphosphine complex or the like in an amount of 0.01–0.1 molar equivalent to each of the compounds (III-a)

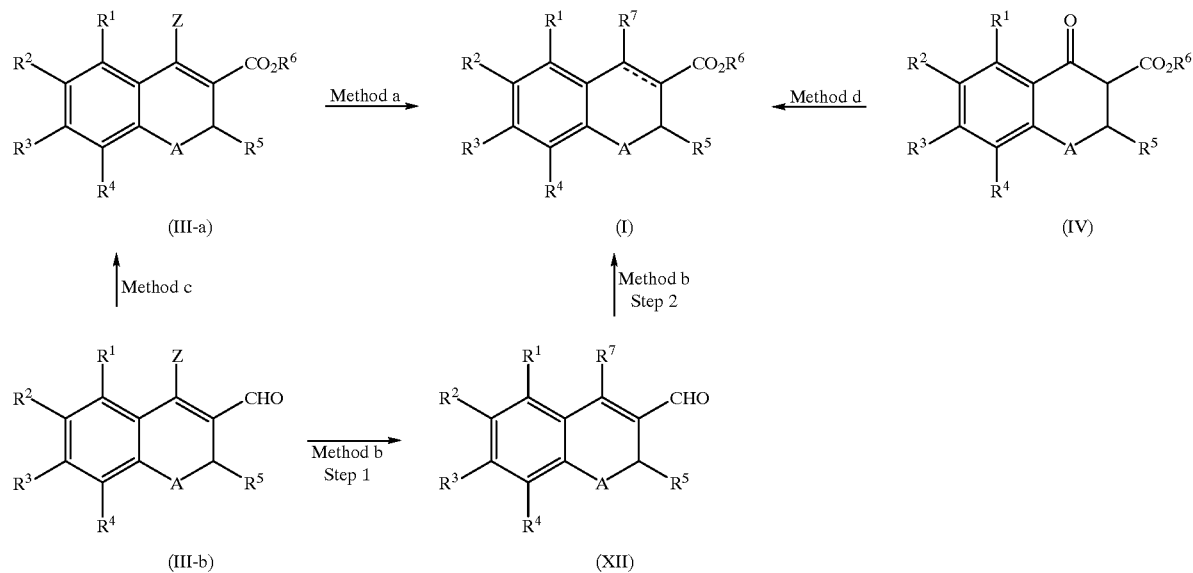

wherein $R^1$–$R^7$, A, Z and a broken line represents the same as defined above.

Method a] (III-a→I)

(Method a-1)

The compound (I) wherein $R^7$ is optionally substituted alkyl optionally substituted alkenyl, optionally substituted alkynyl, optionally substituted cycloalkyl, optionally substituted aryl or optionally substituted heteroaryl can be obtained by a reaction of the compounds (III-a) wherein Z is halogen or optionally substituted alkoxy with a Grignard reagent $R^7$-MgX wherein $R^7$ is optionally substituted alkyl, optionally substituted alkenyl optionally substituted alkynyl, optionally substituted cycloalkyl, optionally substituted aryl or optionally substituted heteroaryl and X is halogen. The Grignard reagent can be prepared in a usual manner. Ferric chloride, tris(dibenzoylmethanato)iron, iron acetylacetonate or the like may be added as a catalyst, if necessary. As a reaction solvent, anhydrous etheral solvents such as anhydrous tetrahydrofuran or anhydrous ether or the like is usually employed. The reaction may generally be carried out at 0° C. to the solvent-refluxing temperature.

(Method a-2)

The compound (I) wherein $R^7$ is optionally substituted aryl or optionally substituted heteroaryl and $R^6$ is optionally substituted alkyl or optionally substituted aryl can also be synthesized by the reaction of the compound (III-a) wherein $R^6$ is optionally substituted alkyl or optionally substituted aryl, Z is halogen or perfluoroalkylsulfonyloxy represented by —$OSO_2(C_qF_{2q+})$ and q=0–4 with $R^7$-M wherein $R^7$ is optionally substituted aryl or optionally substituted heteroaryl and M is a metallic group in the presence of a palladium catalyst. An organic boron compound (Suzuki Reaction, Chem. Rev. 1995, 95, 2457), an organic tin compound (Stille Reaction, Chem. Int. Ed. 1986, 25, 508) or an organic halogeno zinc compound represented by ZnX is usually used. In the Suzuki Reaction, 1.5–2 equivalents of an inorganic base such as sodium carbonate, potassium carbonate, thallium carbonate, barium hydroxide, thallium hydroxide or the like, and an inorganic salt such as a copper salt, lithium chloride or the like are usually added. Dioxane, 1,2-dimethoxyethane, tetrahydrofuran, toluene, benzene, acetonitrile, DMF, water and/or the like can be used solely or as a mixed solvent. The reaction may usually be carried out at room temperature to solvent-refluxing temperature.

(Method a-3)

The compound (I) wherein $R^7$ is optionally substituted alkylamino and $R^6$ is optionally substituted alkyl or optionally substituted aryl can be synthesized by the reaction of the compounds (III-a) wherein Z is halogen, optionally substituted-alkylsulfonyloxy or optionally substituted arylsulfonyloxy and $R^6$ is optionally substituted alkyl or optionally substituted aryl with a mono- or di-substituted amine. The reaction is carried out using tetrahydrofuran, dimethylformamide or the like at 0° C. to 60° C.

Hydrolysis of the compound (I) wherein $R^6$ is optionally substituted alkyl or optionally substituted aryl gives the compound (I) wherein $R^6$ is hydrogen.

(Method a-4)

The compound (I) wherein $R^6$ is hydrogen, optionally substituted alkyl or optionally substituted aryl, preferably $R^6$ is hydrogen, and $R^7$ is optionally substituted alkoxy, optionally substituted aryloxy, optionally substituted alkenyloxy, optionally substituted alkynyloxy, optionally substituted alkylthio, optionally substituted alkenylthio or optionally substituted alkynylthio can be synthesized by the reaction of the compounds (III-a) wherein $R^6$ is hydrogen and Z is halogen, optionally substituted alkylsulfonyloxy or optionally substituted arylsulfonyloxy with an alkaline metal salt or alkaline earth metal salt of the corresponding alcohol or thiol. Tetrahydrofuran, dimethylformamide or the like is used as a reaction solvent. The reaction is usually carried out at room temperature to 50° C.

The compound (III-a) can be converted into another class of compounds (III-a) by an appropriate reaction. For example, ester group of compounds (III-a) can be hydrolyzed with an acid or an alkali in a usual manner to give a carboxylic acids (III-a). A carboxylic acids (III-a) can be esterified by a similar method as described in the above Method A, Step 2 to give a ester compound (III-a).

[Method b] (III-b→XII→I)

(Method b, Step 1) (III-b→XII)

An aldehyde (XII) wherein $R^7$ is optionally substituted alkyl, optionally substituted alkenyl, optionally substituted alkynyl, optionally substituted cycloalkyl, optionally substituted aryl or optionally substituted heteroaryl can be synthesized by the reaction of the compound (III-b) wherein Z is halogen or perfluoroalkylsulfonyloxy represented by —$OSO_2(C_qF_{2q+1})$; q=0–4 with $R^7$-M wherein $R^7$ is optionally substituted alkyl, optionally substituted alkenyl, optionally substituted alkynyl, optionally substituted cycloalkyl, optionally substituted aryl or optionally substituted heteroaryl and M is the same as defined above in the presence of a palladium catalyst by a similar method as the above Method a-2.

The compound (XII) wherein $R^7$ is optionally substituted alkoxy, optionally substituted alkenyloxy, optionally substituted alkynyloxy, optionally substituted aryloxy, optionally substituted alkylthio, optionally substituted alkenylthio or optionally substituted alkynylthio can also be synthesized by the reaction of compounds (III-b) wherein Z is halogen with an alkaline metal salt or alkaline earth metal salt of the corresponding alcohol or thioalcohol in the same manner as the above Method a-4. Tetrahydrofuran, dimethylformamide, dimethylsulfoxide or the corresponding alcohol such as methanol or the like is used as a reaction solvent. The reaction may be carried out at room temperature to the solvent-refluxing temperature.

(Method b, Step 2) (XII→I)

The compounds (I) wherein $R^6$ is hydrogen can be synthesized by oxidation of the corresponding formyl compounds (XII). The methods of oxidation of a formyl compound to a carboxyl compound are exemplified in Step 2 of Method B.

Method c] (III-b→III-a→I)

The compounds (III-a) wherein Z is halogen or optionally substituted alkoxy and $R^6$ is hydrogen can be synthesized by oxidation of the formyl group in the compounds (III-b) wherein Z is halogen or optionally substituted alkoxy. The method for the oxidation of the formyl group to the carboxyl group is the same as described in Step 2 of Method B.

Finally, the objective compounds (I) can be prepared by the same method as described in the above Method a.

[Method d] (IV→I)

The compound (I) wherein $R^7$ is optionally substituted alkoxy, optionally substituted alkenyloxy or optionally substituted alkynyloxy and $R^6$ is optionally substituted alkyl or optionally substituted aryl can be synthesized by the reaction of a compound (V) wherein $R^6$ is optionally substituted alkyl or optionally substituted aryl with a corresponding alcohol in the presence of triphenylphosphine or tributylphosphine, and dialkylazodicarboxylate such as diethylazodicarboxylate or tetraalkylazodicarboxamide such as 1,1'-(azodicarbonyl)dipiperidine, N,N,N',N'-tetramethylazodicarboxamide. This reaction is carried out by a similar manner as described in Synthesis, 1981, 1, 1 (the Mitsunobu Reaction). A preferable solvent is an etheral solvent such as tetrahydrofuran etc., benzene, toluene or the like. The reaction is usually carried out at −15° C. to room temperature.

Further, the chromane derivative (I) wherein a double bond between the 3- and 4- positions is reduced can be obtained by the reduction of the obtained compounds (I).

The double bond at the C3–C4 positions is reduced by catalytic reduction. A platinum catalyst such as platinum oxide or the like or a palladium catalyst retained on a carrier such as palladium/carbon, palladium oxide, palladium chloride, palladium/calcium carbonate, palladium/barium sulfate or the like can be used as a catalyst. A lower alcohol, an acetate ester, acetic acid, acidic lower alcohol or the like is used as a solvent. The reaction is preferably carried out under atomospheric pressure but, if the reaction speed is slow, under medium-pressure. The reaction temperature is usually at room temperature to 50° C. Stereoisomers may be produced under a certain reaction condition in a reduction of a double bond. Chromane derivatives may be either of a mixture of stereoisomers or any of single stereoisomer and may be either of racemates or optically active compounds.

A certain compound (I) can be converted into the other type of compounds (I) by a method easily carried out by a person skilled in the art. For example, ester compounds (I) wherein $R^6$ is optionally substituted alkyl or optionally substituted aryl can be converted into free carboxylic acids (I) wherein $R^6$ is hydrogen by hydrolysis. Although an explanation for the hydrolysis method is not necessary for a person skilled in the art, a method carried out in a mixture of water-lower alcohol or water-dimethylsulfoxide with an inorganic base is preferable. Examples of an inorganic base are sodium hydroxide, lithium hydroxide, potassium hydroxide and the like. The reaction is usually carried out at ice-bath to refluxing temperature of solvent.

The free carboxylic acids (I) wherein $R^6$ is hydrogen can be esterified by a similar method as described in the above Step 2 of Method A giving an ester compounds (I) wherein $R^6$ is optionally substituted alkyl or optionally substituted aryl.

The free carboxylic acids (1) can be converted into the corresponding salts on treatment with various kinds of organic or inorganic bases. Although there is no need for a person skilled in the art to explain a method for forming a salt, for example, the compound (I) wherein $R^6$ is hydrogen gives a sodium salt with an equal amount of sodium hydroxide in water or a mixture of water and lower alcohol. The salt can be purified by recrystallization, freeze-drying or the like for example.

In the case that $R^1$, $R^2$, $R^3$ or $R^4$ is nitro group, it can be converted into amino group by a catalytic reduction. A noble metal catalyst such as palladium or the like retained on a carrier such as carbon or the like is used for the reduction of nitro group. The reduction is carried out in a solvent such as a lower alcohol, an acetate ester or the like under atmospheric pressure at room temperature.

In the case that $R^1$, $R^2$, $R^3$ or $R^4$ is hydroxy, it can be converted into alkoxy, alkenyloxy or alkynyloxy on treatment with halogenoalkyl, halogenoalkenyl or halogenoalkynyl, respectively, in the presence of a base such as potassium carbonate, cesium carbonate, sodium hydride or the like in a solvent such as acetone, acetonitrile, dimethylformamide or the like. In the case that $R^1$, $R^2$, $R^3$ and $R^4$ is hydroxy, it can be converted into optionally substituted alkoxy, optionally substituted alkenyloxy or optionally substituted alkynyloxy by the reaction with an alcohol in the presence of triphenylphosphine or tributylphosphine, and dialkylazodicarboxylate such as diethylazodicarboxylate or tetraalkylazodicaarboxamide such as 1,1'-(azodicarbonyl)dipiperidine, N,N,N',N'-tetramethylazodicarboxamide (the Mitsunobu Reaction).

In the case that $R^1$, $R^2$, $R^3$ or $R^4$ is hydroxy or amino, although there is no need for a person skilled in the art to explain, it can be converted into acyloxy or acylamino by the reaction with an acid halide, an acid anhydride or the like, in the presence of a base such as pyridine.

If there is an interfering group at any position in a molecule in any of the above-mentioned reaction steps, the group may previously be protected by a method as explained in Protective Groups in Organic Synthesis; John Wiley & Sons: New York, 1991 and the like. A protecting group may be removed in a later suitable step.

For example, if there is hydroxy or amino, a preferable protecting group is benzyl, acetyl, benzoyl and the like. When the protecting group is benzyl, it can be deprotected by catalytic reduction. When the protecting group is acyl such as acetyl, benzoyl or the like, it can be removed by the hydrolysis with sodium carbonate, potassium carbonate, sodium hydroxide, potassium hydroxide, lithium hydroxide or the like in a solvent such as a mixture of lower alcohol and water. Tetrahydrofuran, dioxane or the like may be further added to the mixture. Carbonyl group such as an aldehyde may be synthesized via a suitable reacted intermediates, acetal or ketal, which is deprotected by the hydrolysis in a later suitable step. Compounds having a double bond can also be converted into a carbonyl derivative by oxidation such as hydroxylation, hydroboration, epoxidation and the like.

The compounds (I) of the present invention or intermediates thereof have a asymmetric carbon atom and therefore exists as a racemate and optically active compounds ((+)-compound, (=)-compound). All of them are included in the present invention.

Optical active compounds of the compound (I) can be obtained by optical resolution of their racemates. Alternatively, suitable intermediates may be resolved at first and then converted into the optical active compounds (I) by the same method as used for a racemate. Examples of the optical resolution method include a method using an enzyme, resolution by a fractional recrystallization or chromatography after conversion into a diastereomeric salt or a diastereomer derivative, a synthesis by an asymmetric synthesis and the like.

The compound group (I) has an endothelin receptor antagonistic activity and can be used as a medicament. Because an endothelin is considered to associate with circulatory system diseases such as hypertension, pulmonary hypertension, stroke, acute renal insufficiency, stenocardia, cardiac insufficiency, myocardial infarction, renal ischemia, renal insufficiency, cerebral ischemia, cerebral infarction, cerebral edema, cerebrovascular spasm, and asthma, peripheral circulatory insufficiency (for example, acute or chronic artery obstruction, obstructive arteriosclerosis, obstructive thromboangiitis, Raynaud's disease, Raynaud's syndrome, diabetic cutaneous ulcer, diabetic neuropathy, diabetic vulnerary insufficiency, peripheral circulatory insufficiency of unknown etiology, subjective symptoms caused by a peripheral circulatory insufficiency such as pain, feeling of cold, shoulder stiffness and the like), the antagonist is useful for treating and/or preventing these diseases. The endothelin receptor antagonists such as the compound group (I) and the like have an inhibitory activity for macrophage foam cell formation and are effective also for treating and/or preventing atherosclerosis, diseases caused by atherosclerosis such as stenocardia, myocardial infarction, cerebral infarction, renal infarction, aortic aneurysm, coronary arteriosclerosis, renal arterial hypertension, necrosis of lower limb and circulatory injury of organs.

When the compound group (I) is applied as a medicament or when the endothelin antagonist is applied as a macrophage foam cell formation inhibitor, it can safely be administered either orally or parenterally. In the case of an oral administration, it may be in any usual forms such as tablets, granules, powders, capsules, pills, solutions, suspensions, syrups, buccal tablets, sublingual tablets and the like for the administration. When the compound is parenterally administered, any usual forms are preferable, for example, injections such as intravenous injections or intramuscular injections, suppositories, endermic agents, inhalations and the like. An oral administration is preferable for the compound group (I).

A pharmaceutical composition may be manufactured by mixing an effective amount of the compound group (I) or the endothelin antagonist with various pharmaceutical ingredients suitable for the administration form, such as excipients, binders, moistening agents, disintegrators, lubricants, diluents and the like. When the composition is an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxymethylcellulose, hydroxypropylcellulose, gelatin, polyvinylpyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methyl cellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added. For an oral administration, sweetening agents, flavors and the like may be added.

Although a dosage of the compound group (I) as an endothelin receptor antagonist or a dosage of the endothelin antagonist as a macrophage foam cell formation inhibitor should be determined in consideration of the patient's age and body weight, the type and degree of diseases, the administration route and the like, a usual oral dosage for human adults is 0.05–100 mg/kg/day and the preferable dosage is 0.1–10 mg/kg/day. In the case that it is parenterally administered, although the dosage highly varies with administration routes, a usual dosage is 0.005–10 mg/kg/day, preferably, 0.01–1 mg/kg/day. The dosage may be administered in one or some separate administrations.

EXAMPLES

The present invention is further explained by the following Examples and Experiments, which are not intended to limit the scope of the present invention. The structures of the compounds are tabulated in Tables 1 to 6 and physical constants are summarized in Tables 7 to 18.

The following abbreviations are used in the Examples.

| | |
|---|---|
| Me | methyl |
| Et | ethyl |
| nPr | n-propyl |
| iPr | isopropyl |
| cPr | cyclopropyl |

-continued

| | |
|---|---|
| cPent | cyclopentyl |
| cHex | cyclohexyl |
| nBu | n-butyl |
| nPent | n-pentyl |
| nHex | n-hexyl |
| nHep | n-heptyl |
| Ph | phenyl |
| MD | methylenedioxy |
| Th | thienyl |
| Bn | benzyl |
| Tf | trifluoromethanesulfonyl |
| THF | tetrahydrofuran |
| DMF | dimethylformamide |
| DME | dimethoxyethane |
| MeOH | methanol |
| DMSO | dimethylsulfoxide |

Reference Example 1 3,4-Methylenedioxyphenyl boric acid

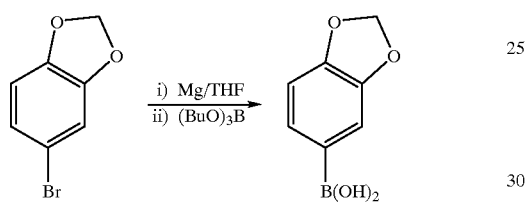

A solution of 3,4-methylenedioxybromobenzene (2.00 g, 9.95 mmol) in anhydrous THF (20 ml) was added dropwise to magnesium turnings(254 mg, 10.45 mmol) and stirred for 1 h. After the reaction completed, the reaction mixture was cooled to −78° C., and a solution of tributyl borate (3.22 ml, 11.94 mmol) in anhydrous THF (30 ml) was added dropwise and stirred for 15 min at the same temperature. Cooling bath was removed and the reaction mixture was allowed to warm to ambient temperature and stirred for another 15 min. Ice water was added and the mixture was acidified with hydrochloric acid and extracted twice with ether. A combined organic layers were washed with brine and dried over magnesium sulfate and the solvent was removed under reduced pressure. The residue was air-dried to give 3,4-methylenedioxyphenyl boric acid (986 mg, 60%) as white crystals.

Reference Example 2 Methyl 2-(benzo[1,3]dioxol-5-yl-6-benzyloxy-4-(trifluoromethanesulfonyloxy)-2H-chromen-3-carboxylate (III-1)

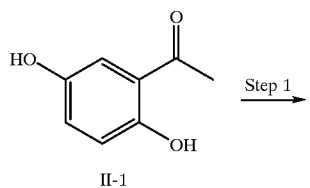

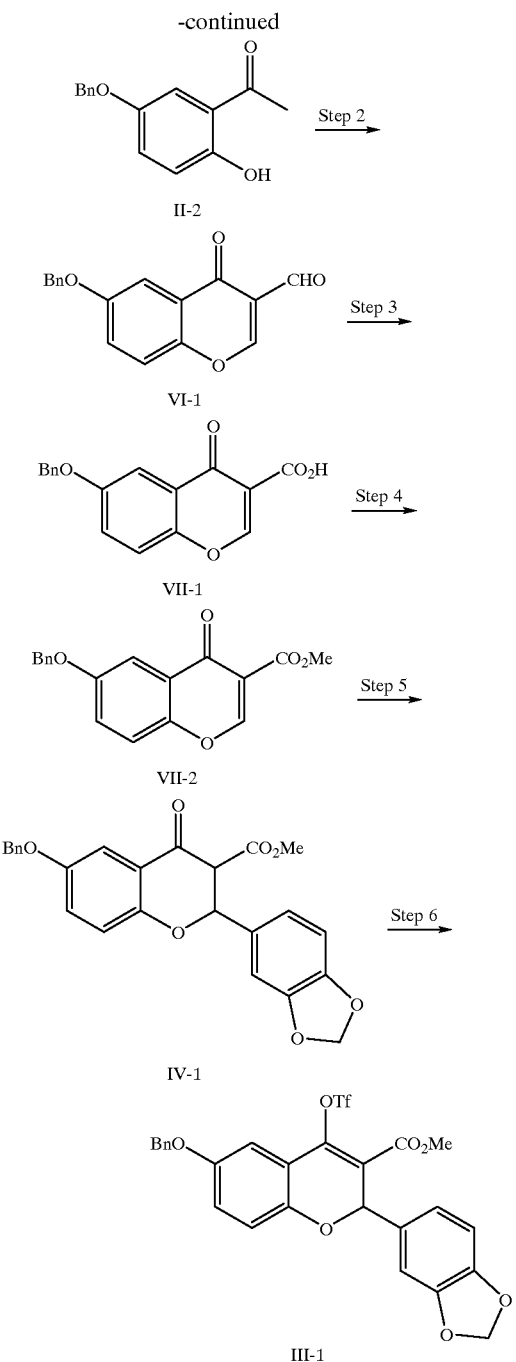

(Step 1) 5'-Benzyloxy-2'-hydroxyacetophenone (II-2)

2', 5'-Dihydroxyacetophenone (II-1) (15.22 g, 0.100 mol), benzyl bromide (17.96 g, 0.105 mol) and potassium carbonate (14.51 g, 0.105 mol) in acetone (200 ml) were refluxed for 16 h. After the solvent was removed under reduced pressure, water was added and the residue was extracted three times with ethyl acetate. The ethyl acetate layer was washed with water and brine, dried over magnesium sulfate, and the solvent removed under reduced pressure. The residue was purified by chromatography on silica gel (500 g) eluting with ethyl acetate/hexane=1:4 to give compound (II-2) as yellow crystals (20.96 g, 87%) accompanied by a small amount of di-benzyl derivative. The products were used without further purification. NMR(CDCl₃): 2.57(3H, s), 5.04(2H, s), 6.92(1H, d, J=8.8), 7.14–7.31(2H, m), 7.34–7.45(5H, m)

(Step 2) 6-Benzyloxy-4-oxo-4H-chromen-3-carbaldehyde (VI-1)

The compound (II-2) (20.96 g, 0.087 mol) was dissolved in DMF (90 ml) and cooled to −15° C. Phosphorous oxychloride (32.3 g, 0.346 mol) was added dropwise to the solution at a rate to maintain the reaction temperature below −10° C. and the solution was stirred for 30 min at the same temperature. Cooling bath was removed and the reaction mixture was allowed to warm to ambient temperature and left stand overnight. The reaction mixture was poured into about 300 ml of ice water and the precipitate was collected, washed with water and air-dried. Recrystallization from acetone-isopropylether gave compound (VI-1) as colorless crystals (13.25 g, 56%). m.p. 163–165.5° C NMR(CDCl$_3$): 5.18(2H, s), 7.37–7.52(7H, m), 7.76(1H, d, J=2.8), 8.54(1H, s), 10.41(1H, s)

(Step 3) 6-Benzyloxy-4-oxo-4H-chromen-3-carboxylic acid (VII-1)

The compound (VI-1) (3.20 g, 0.0114 mol) in methylene chloride (86 ml) and an aqueous solution (64 ml) of sulfamic acid (6.41 g, 0.066 mol) were stirred at ice-bath temperature to which an aqueous solution (4 ml) of sodium chlorite (80% purity, 4.88 g, 0.0432 mol) was added. The cooling bath was removed and the solution was stirred for 2 h at ambient temperature. The organic layer was separated and the aqueous layer was extracted twice with chloroform. The organic layers were combined, washed with water and brine, dried over magnesium sulfate, and the solvent removed under reduced pressure. The residue was recrystallized from 95% ethanol to give compound (VII-1) (2.42 g, 72%) as colorless crystals. m.p. 170–173° C. NMR(CDCl$_3$): 5.20(2H, s), 7.36–7.76(8H,m), 8.99(1H, s)

(Step 4) Methyl 6-benzyloxy-4-oxo-4H-chromen-3-carboxylate (VII-2)

Oxalyl chloride (1.03 ml, 11.62 mmol) was gradually added dropwise to a solution of compound (VII-1) (2.87 g, 9,69 mmol) and DMF (0.3 ml) in methylene chloride (60 ml) and the resulting mixture was stirred for 1 h at ambient temperature. Methanol (10 ml) was added. The solvent was removed under reduced pressure. The residue was purified by silica gel chromatography (30 g) eluting with ethyl acetate/hexane=1:3. The products were recrystallized from ethyl acetate/hexane to give compound (VII-2) (2.39 g, 79%) as colorless crystals. m. p. 88–89° C. NMR(CDCl$_3$): 3.93(3H, s), 5.16(2H, s), 7.32–7.47(7H, m), 7.74(1H, d, J=2.8), 8.67(1H, s)

(Step 5) Methyl 2-(benzo[1,3]dioxol-5-yl)-6-benzyloxy-4-oxo-chroman-3-carboxylate (IV-1)

3,4-methylenedioxybromobenzene (2.63 g, 13.09 mmol) and magnesium turnings(334 mg, 13.74 mmol) were reacted in refluxing anhydrous THF (60 ml) for 1 h. After the reaction completed, the reaction mixture was allowed to cool to ambient temperature, and copper iodide (97 mg, 0.51 mmol) was added and stirred for additional 15 min. After the reaction mixture was cooled to 0° C., a solution of compound (VII-2) (2.39 g, 7.70 mmol) in anhydrous THF (100 ml) was added dropwise over 30 min period and stirred for 1 h at the same temperature. The reaction mixture was poured into ice water and hydrochloric acid and extracted three times with ether. The ether layer was washed with water and brine, dried over magnesium sulfate, and the solvent removed under reduced pressure. The residue was purified by silica gel (99 g) chromatography eluting with toluene followed by toluene/acetonitrile=9:1. Compound (IV-1) (3.29 g, 99%) was obtained as an yellow oil. NMR spectrum of compound (IV-1) indicated that the products were a mixture of keto-enol tautomeric isomers.

(Step 6) Methyl 2-(benzo[1,3]dioxol-5-yl)-6-benzyloxy-4-(trifluoromethanesulfonyloxy)-2H-chromen-3-carboxylate (III-1)

A solution of compound (IV-1) (3.02 g, 6.98 mmol) in DMF (50 ml) was added dropwise to a suspension of sodium hydride (60% oil dispersion, 335 mg, 8.38 mmol) in DMF (30 ml) at ambient temperature. After stirring for 30 min, 2-[N,N'-bis(trifluoromethanesulfonyl)amino]pyridine (2.87 g, 8.03 mmol) was added and stirred for another 2 h. The reaction was quenched by addition of ice water and the layers were extracted three times with ether. The organic layer was successively washed with saturated aqueous solution of ammonium chloride, water and brine, dried over magnesium sulfate and concentrated. The residue was purified by chromatography on silica gel (100 g) eluting with toluene. Compound (III-1) (3.53 g, 90%) was obtained as an yellow oil.

NMR(CDCl$_3$): 3.83(3H, s), 4.99(2H, s), 5.92(2H, s), 6.33(1H, s), 6.68–7.00(6H, m), 7.35–7.39(5H, m)

Reference Example 3 Methyl 6-butoxy-4-oxo-4H-chromen-3-carboxylate (VII-3)

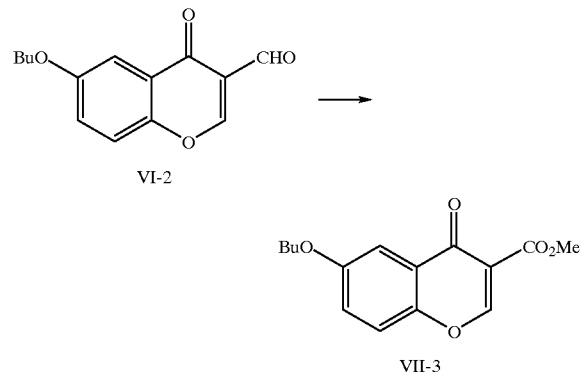

6-Butoxy-4-oxo-4H-chromen-3-carbaldehyde (VI-2; 5 g, 0.02 mol) prepared by the method described in Steps 1 and 2 of the Reference Example 2 and N-bromo succinicimide (4.4 g) were refluxed in carbon tetrachloride (350 ml) for 1 h while it was irradiated externally with 250W Matsushita Electric tungsuten lamp. The mixture was allowed to cool in an ice-bath and anhydrous methanol (6 ml) was added slowly and stirred for additional 30 min. The solvent was removed under reduced pressure and the residue was dissolved in ethyl acetate. The organic layer was washed successively with water, 1 M sodium hydroxide, water and brine and dried. The solvent was evaporated under reduced pressure to give 6.2 g of an orange solid. Recrystallization from 95% ethanol afforded 4.3 g (77%) of compound (VII-3) as pale yellow prisms. m.p. 88–89° C.

NMR(CDCl$_3$): 0.99(3H, t, J=7.3), 1.51(2H, m), 1.81(2H, m), 3.94(3H, s), 4.06(2H, t, J=6.4), 7.28(1H, dd, J=9.0, 3.0), 7.62(1H, d, J=3.0), 7.43(1H, d, J=9.0), 8.68(1H, s)

Reference Example 4 Methyl 4-oxo-8-propyl-4H-chromen-3-carboxylate (VII-4)

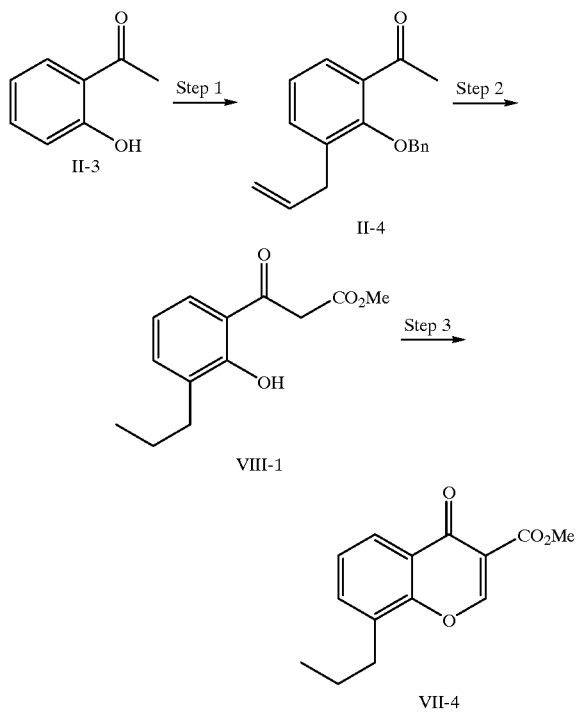

(Step 1) 3'-Allyl-2'-benzyloxy-acetophenone (II-4)

2'-Hydroxyacetophenone (1I-3) (14.0 g, 0.103 mol), allyl bromide (20.4 g, 0.169 mol) and potassium carbonate (14.2 g, 0.103 mol) in acetone (140 ml) were refluxed for 16 h. The solvent was removed under reduced pressure and water was added. The layers were extracted with ether and the organic extracts were washed with water, dried over magnesium sulfite and concentrated under reduced pressure leaving 17.9 g of 2'-allyloxyacetophenone as a colorless oil. 8.6 g of allyl ether thus obtained was refluxed in 1,2-dichlorobenzene (40 ml) in an oil bath heated at 210° C. for 18 h. The solvent was removed under reduced pressure to give 8.9 g of 3'-allyl-2'-hydroxyacetophenone. Without purification, the product was dissolved in DMF (60 ml) and was added dropwise to a suspension of sodium hydride (60% oil dispersion, 2.4 g, 0.06 mol) in DMF (25 ml) at a rate keeping the reaction temperature between 40 to 45° C. After stirring for additional 20 min, a solution of benzyl bromide (8.6 g, 0.05 mol) in DMF (10 ml) was added dropwise. After 2 h and 4 h, each 0.7 g of additional benzyl bromide was added. After 6 h, the reaction mixture was poured into ice water and extracted with ether. The organic layer was washed with water, dried over magnesium sulfate, and the solvent was removed to give 14.0 g of an orange oil. This was purified by 250 g of silica gel chromatography (ethyl acetate/hexane=1:4) to give compound (II-4) (9.6 g) as a pale yellow oil.

NMR(CDCl$_3$): 2.60(3H, s), 3.46(2H, d), 4.85(2H, s), 5.0–5.2(2H, m), 5.85–6.06(1H, m), 7.11–7.49(8H, m)

(Step 2) Methyl 3-(2-hydroxy-3-propyl-phenyl)-3-oxo-propionate (VIII-1)

Sodium hydride (60% oil dispersion, 3.2 g, 0.08 mol) was suspended in dimethyl carbonate (15 ml) and allowed to warm to about 82° C. A solution of compound (II-4) (9.6 g, 0.0361 mol) in dimethyl carbonate (40 ml) was added dropwise and the reaction was continued for 1 h at 80° C. The reaction mixture was poured into ice water, acidified with acetic acid and extracted with ether. The organic layer was washed with water, dried, and the solvent was removed under reduced pressure. Without further purification, the products were hydrogenated over 10% palladium/carbon (39 mg) in ethanol (60 ml) to give compound (VIII-1) (8.42 g, 99%) as an oil. NMR(CDCl$_3$): 0.96(3H, t, J=7.3), 1.64(2H, m), 2.64(2H, t, J=7.6), 3.77(3H, s), 4.03(2H, s), 6.85(1H, dd, J=7.7 and 7.7), 7.37(1H, m), 7.52(1H, dd, J=7.7 and 1.6)

(Step 3) Methyl 4-oxo-8-propyl-4H-chromen-3-carboxylate (VII-4)

Compound (VIII-1) was refluxed in a mixture of methyl orthoformate (48 ml) and acetic anhydride (24 ml) for 17 h. The solvent was removed under reduced pressure and the residue was chromatographed on 280 g of silica gel and ethyl acetate/hexane (1:4) as eluent to give compound (VII-4) (5.5 g, 67%) as an oil.

NMR(CDCl$_3$): 0.99(3H, t, J=7.3), 1.70(2H, m), 2.85(2H, t, J=7.4), 3.94(3H, s), 7.33–7.56(2H, m), 8.14(1H, dd, J=8.0 and 1.8), 8.74(1H, s).

Reference Example 5 Methyl 2-(benzo[1,3]dioxol-5-yl)-6-isopropoxy-4-oxo-chroman-3-carboxylate (IV-2)

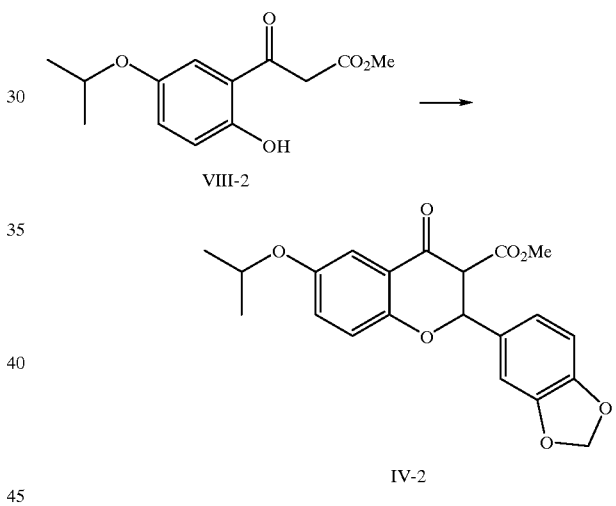

A solution of piperonal (182.4 g, 1.22 mol) in toluene (1 L) was heated to reflux in a flask equipped with a Dean Stark dehydration apparatus to which a mixture of methyl 3-(2-hydroxy-5-isopropoxy-phenyl)-3-oxo-propionate (VIII-2) (151 g, 0.61 mol) synthesized by the method described in Reference Example 4, piperidine (1.55 g, 0,018 mol), acetic acid (3.65 g, 0.061 mol) in toluene (1.3 L) was added dropwise over a period of 1 h and the solution was refluxed for another 1 h. After cooling, the reaction mixture was poured into ice water (3 L) and extracted with toluene. The organic layer was washed with water, dried, and concentrated under reduced pressure. The residue was treated with Girard T reagent (143 g) in methanol (500 ml) and toluene (2 L) for 2 h. Brine (3.5 L) was added and the organic layer was separated and the aqueous layer was further extracted with toluene. The combined organic layers were washed with water, dried, and concentrated. The residue was subjected to a chromatographed on silica gel (toluene). During the elution, the products gradually cyclized to give compound (IV-2) (102 g, 44%) as an oil. The oil was clarified a keto-enol tautomeric mixture as shown by NMR. NMR (CDCl₃):1.3 1(d, J=6.0), 1.32*(d, J=6.2), 3.67*(s), 3.76(s), 4.02*(d, J=12.0), 4.46(m), 4.53*(m), 5.55*(d, J=12.0), 5.91*(s), 6.00(s),6.10(s), 6.67–7.36(m) (* are signals derived from a major product)

Reference Example 6 Methyl 6-methoxy-4-oxo-4H-thiochromen-3-carboxylate (VII-5)

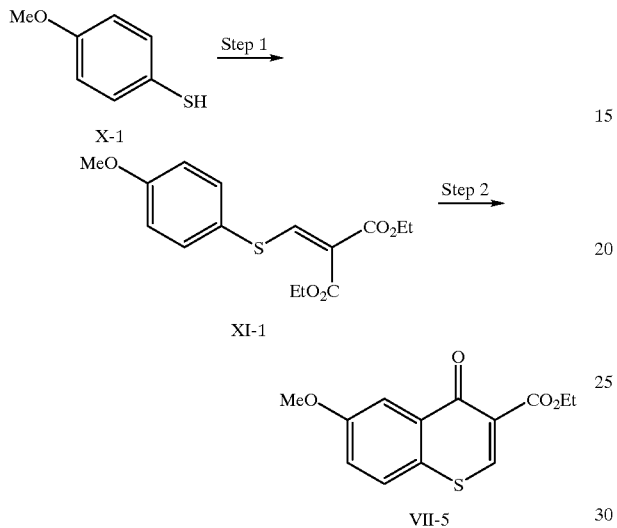

(Step 1) Diethyl 2-(4-methoxy-phenylsulfanylmethylene)-malonate (XI-1)

4-Methoxybenzenethiol (X-1; 5 g, 0.0357 mol), diethyl ethoxymethylene malonate (7.3 ml) and sodium hydrogen sulfate monohydrate (100 mg) were heated with stirring in an oil bath at 166° C. for 2 h. After cooling, ice water was added to the reaction mixture and extracted with ether. The crude product was purified by silica gel (250 g) and ethyl acetate/hexane (1:4) to give compound (XI-1) (5.7 g, 51%) as an oil. NMR(CDCl₃):1.29(3H,t, J=7.1), 1.38(3H, t, J=7.1), 3.83(3H, s), 4.23(2H, q, J=7.1), 4.35(2H, q, J=7.1), 6.93, 7.45(4H, AB, J=8.8), 8.30(1H,s)

(Step 2) Ethyl 6-methoxy-4-oxo-4H-thiochromen-3-carboxylate (VII-5)

Compound (XI-1) (238 mg, 0.77 mmol) and polyphosphoric acid(84%, 2.8 g) were heated with stirring in an oil bath at 95° C. for 6h. After cooling, ice water was added to the reaction mixture and the layers were extracted with ether. The crude extract was purified by chromatography on silica gel (12 g) and ethyl acetate/hexane (1:3) as eluent. Compound (VII-5) (180 mg, 89%) was obtained as a colorless solid. Recrystallization from ethyl acetate/hexane afforded colorless plates. m.p. 85–86° C. NMR(CDCl₃): 1.41(3H, t, J=7.1), 3.93(3H, s), 4.41(2H, q, J=7.1), 7.26(1H, dd, J=8.8 and 2.8), 7.53(1H, d, J=8.8). 8.07(1H, d, J=2.8), 8.71(1H, s)

Reference Example 7 Methyl 2-(benzo[1,3]dioxol-5-yl)-6-isopropoxy-4-(trifluoromethanesulfonyloxy)-2H-chromene-3-carboxylate (III-2)

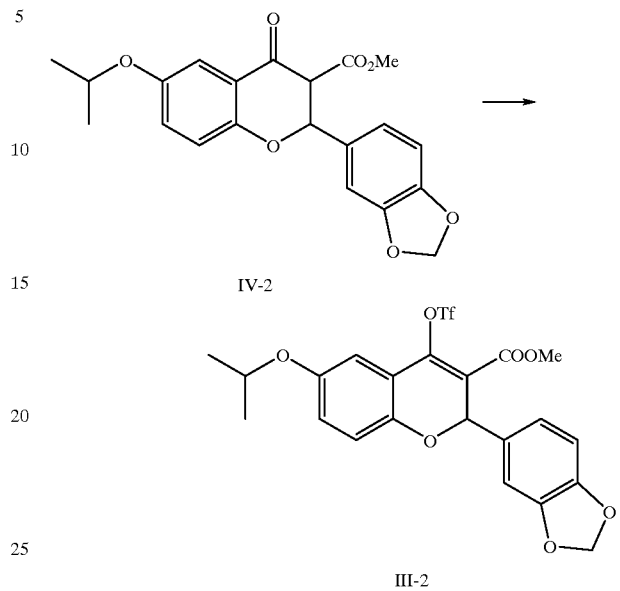

The compound (IV-2) prepared in the Reference Example 5 was converted to compound (III-2) by the method described in Step 5 of the Reference Example 2. m.p. 88–90° C.

NMR(CDCl₃):1.30(3H, d, J=6.0), 1.31(3H, d, J=6.0), 3.83(3H, s), 4.40(1H, m), 5.92(2H, s), 6.32(1H, s), 6.62–6.98(6H, m).

Analysis for: C22H19O9SF3

Calculated: C,51.17; H,3.71; S,6.21; F,11.04

Found: C,51.30; H,3.77; S,6.14; F,11.07

Example 1 2-(Benzo[1,3]dioxol-5-yl)-6-isopropoxy-4-methoxy-2H-chromen-3-carboxylic acid (I-54)

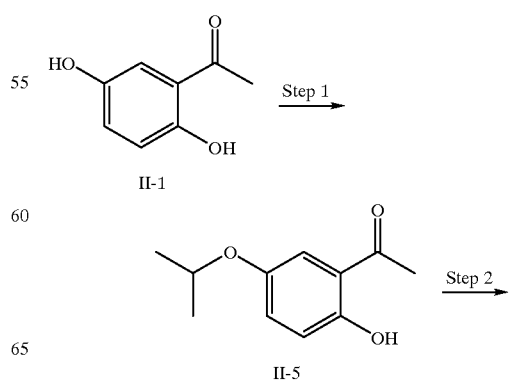

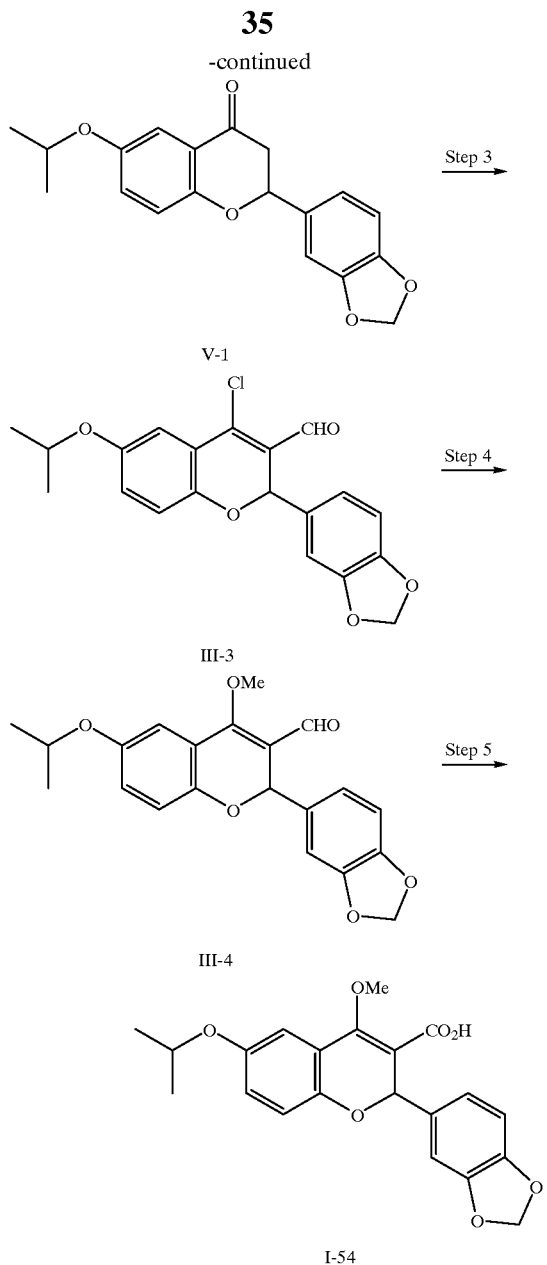

(Step 1) 5'-Isopropoxy-2'-hydroxyacetophenone (II-5)

A mixture of compound (II-1) (1000 g, 6.58 mol), acetonitrile (15 L), potassium carbonate (2271 g, 16.46 mol) and 2-bromopropane (2021 g, 16.57 mol) was stirred at 75° C. for 24.5 h. Insoluble matrerials were removed by filtration and the solvent removed under reduced pressure. The residue was dissolved in 1.2 M solution of sodium hydroxide (7.8 L) and extracted with hexane. An aqueous layer was acidified with hydrochloric acid and extracted with toluene. Toluen layers were washed with water and dried over sodium sulfate. Removal of the solvent afforded compound (II-5) (978 g, 77%) as a yellow oil.

NMR(CDCl$_3$): 1.32(6H, d, J=6.1), 2.6(3H, s), 4.34–4.52 (1H, m), 6.89–7.23(3H, m)

(Step 2) 2-(Benzo[1,3]dioxol-5-yl)-6-isopropoxychroman-4-on (V-1)

To a suspension of compound (II-5) (219 g, 1.13 mol) in methanol (0.57 l) was added piperonal (170 g, 1.13 mol) followed by 2M solution of sodium hydroxide (1.13 l) and stirred for 3 days at ambient temperature. A red precipitate was collected by filtration, washed with water, and dried. Compound (V-1) was obtained as yellow crystals (336 g, 91%).

m.p. 125–126° C.

NMR(CDCl$_3$):1.33(6H, d, J=6.1), 2.76–3.11(2H, m), 4.44–4.62(1H, m), 5.34(1H, dd, J=13.0, 3.2), 5.99(2H, s), 6.81–7.36(6H, m)

Analysis for: C19H18O5

Calculated: C,69.95; H,5.56

Found: C,70.03; H,5.63

(Step 3 2-(Benzo[1,3]dioxol-5-yl)-4-chloro-6-isopropoxy-2H-chromen-3-carbaldehyde (III-3)

Phosphorus oxychloride (280 ml) was added dropwise to DMF (900 ml) over 50 min while the reaction temperature was kept below 16° C. in an ice-bath. The mixture was stirred for further 30 min then a solution of compound (V-l) (392 g, 1.20 mol) in DMF (276 ml) was added dropwise and stirred for 26h at ambient temperature. The reaction mixture was poured into a mixture of sodium acetate (1.23 kg), water (4.7 l), and ethyl acetate (235 ml) below −35° C. and stirred for 1 h. The precipitate was collected by filtration and dried to give the compound (III-3) (437 g, 98%). m.p. 126–127° C.

NMR(CDCl$_3$): 1.33(6H, d, J=6.0), 4.38–4.57(1H, m), 5.9(2H, s), 6.23(1H, 8), 6.60–7.26(6H, m),10.26(1H, s)

(Step 4) 2-(Benzo[1,3]dioxol-5-yl)-6-isopropoxy-4-methoxy-2H-chromen-3-carbaldehyde (III-4)

A mixture of compound (II-3) (20 g, 0.054 mol), sodium methoxide (11.37 g, 0.211 mol), and methanol (200 ml) was refluxed under nitrogen for 40 min. After the reaction mixture was concentrated, ice water was added and extracted with ethyl acetate. The organic layer was washed with water and dried over magnesium sulfate, and the solvent was removed under reduced pressure to give the compound (III-4) (22.64 g) as an oil.

NMR(CDCl$_3$):1.32(6H, d, J=6.0), 4.06(3H, s), 4.35–4.53 (1H, m), 5.88(2H, s), 6.24(1H, s), 6.64–7.26(6H, m), 10.21 (1H, s)

(Step 5) 2-(Benzo[1,3]dioxol-5-yl)-6-isopropoxy-4-methoxy-2H-chromen-3-carboxylic acid (I-54)

Into a rigorously stirred mixture of compound (III-4) in DMSO (300 ml) and sodium dihydrogen phosphate (16.08 g) in water (40 ml) was added dropwise an aqueous solution (60 ml) of sodium chlorite (45.15 g) over 49 min period while the reaction temperature was maintained below 23° C. After 25 min, another sodium chlorite (3.03 g) was added and stirred for 25 min then sodium dihydrogen phosphate (1.61 g) and sodium chlorite (1.52 g) were added. Stirring was continued for further 35 min, then the reaction mixture was poured into water and extracted with ethyl acetate. The organic layer was washed with 5% solution of sodium thiosulfate and water, dried over magnesium sulfate, and concentrated. Toluene was added to the residue and the precipitate was collected to give compound (I-54) (14.82 g, 72% from (III-3)).

Example 2 Isopropyl 2-(benzo[1,3]dioxol-5-yl-6-isopropoxy-4-methoxy-2H-chromen-3-carboxylate (Ia-7)

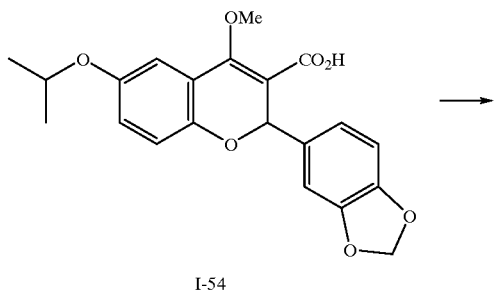

I-54

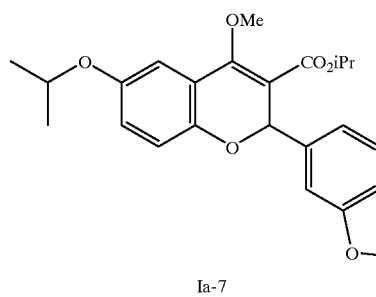

Ia-7

Potassium carbonate (2.16 g), 2-bromopropane (1.92 g) and compound (I-54) (3.0 g, 0.0078 mol) in DMF (30 ml) were stirred at 50° C. for 17 h. The reaction mixture was poured into ice water and extracted with ethyl acetate. The solvent was removed under reduced pressure and the residue was purified by silica gel chromatography (hexane/ethyl acetate=4:1) to give the compound (Ia-7) (3.56 g, 96%).

Example 3 2-(Benzo[1,3]dioxol-5-yl)-4-chloro-6-isopropoxy-2H-chromen-3-carboxylic acid (I-88)

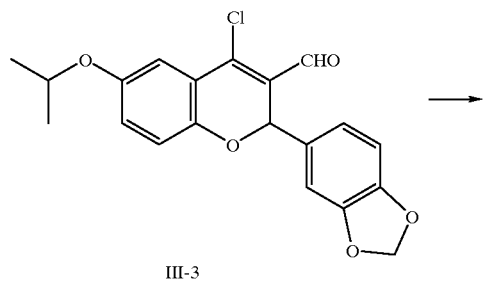

III-3

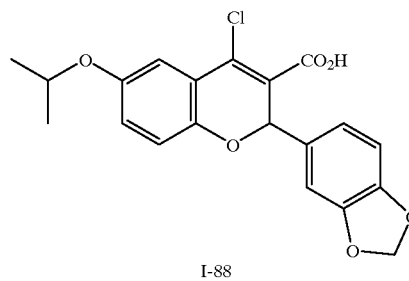

I-88

An aqueous solution (346 ml) of amidosulfuric acid (57.6 g) was added to a solution of compound (III-3) (92 g, 0.247 mol) dissolved in toluene (1.38 L). Sodium chlorite (55.9 g) in water (346 ml) was added over 1 h while the reaction mixture was kept below 10° C. in an ice-bath. After being stirred for 20 min, an aqueous solution (100 ml) of sodium sulfite (31 g), aqueous solution of sodium hydroxide, and toluene was added successively. The layers were separated and an aqueous layer was acidified with hydrochloric acid. The precipitate was collected to give compound (I-88) (87.47 g, 91%) as yellow crystals.

Example 4 Methyl 2-(benzo[1,3]dioxol-5-yl)-4-chloro-6-isopropoxy-2H-chromen-3-carboxylate (Ia-9)

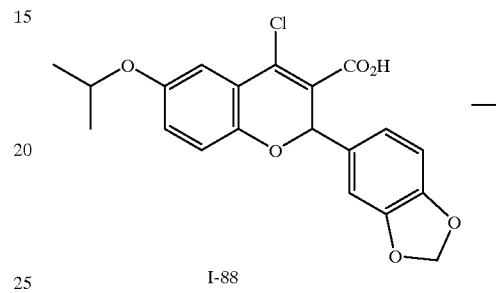

I-88

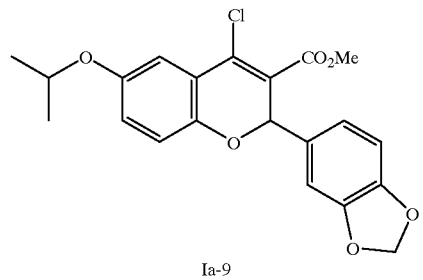

Ia-9

Potassium carbonate (3.73 g, 0.027 mol) and methyl iodide (3.83 g, 0.027 mol) were added to a solution of compound (I-88) (7.0 g, 0.018 mol) in DMF (70 ml) and stirred for 3 h at 15° C. The reaction mixture was poured into ice water and extracted with toluene. The crude product was purified by silica gel chromatography (hexane/ethyl acetate=4:1) to give compound (Ia-9) (7.3 g, 100%).

Example 5 2-(Benzo[1,3]dioxol-5-yl)-6-isopropoxy-4-(4-methoxy-phenoxy)-2H-chromen-3-carboxylic acid (I-74)

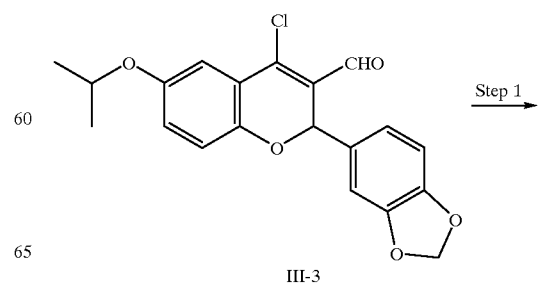

III-3

Step 1

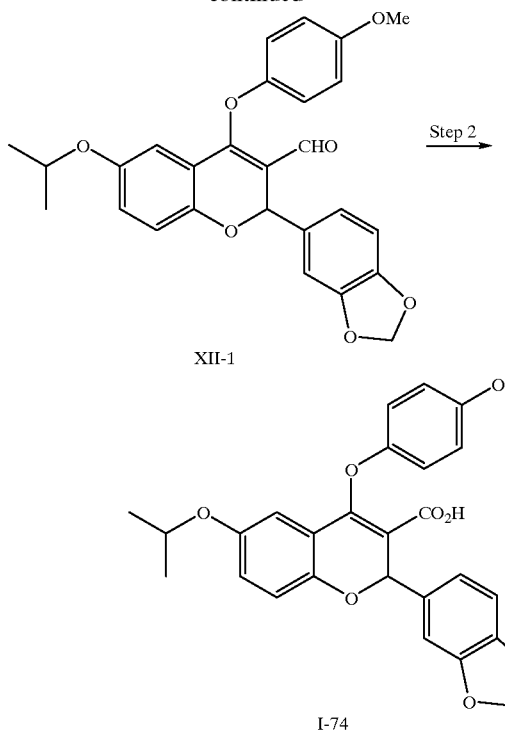

XII-1

I-74

(Step 1) 2-(Benzo[1,3]dioxol-5-yl)-6-isopropoxy-4-(4-methoxy-phenoxy)-2H-chromen-3-carbaldehyde (XII-1)

To a suspension of 60% sodium hydride (60% oil dispersion, 134 mg, 3.35 mmol) in anhydrous THF (2 ml) was added a solution of 4-methoxyphenol (366 mg, 2.95 mmol) in anhydrous THF(4 ml). After being stirred for 1 h at ambient temperature, a solution of compound (III-3) (500 mg, 1.34 mmol) in anhydrous THF (5 ml) was added dropwise and stirred for 6 h. Water was added to the reaction mixture and extracted three times with ether. Ether layer was washed with water and brine and dried over magnesium sulfate. After the solvent was removed under reduced pressure, the residue was purified by silica gel chroamtography (6 g )(toluene/ethyl acetate=9:1). The product was recrystallized from isopropyl ether-acetone to give compound (XII-1) (480 mg, 78%) as yellow crystals. m.p. 94–95° C.

NMR(CDCl$_3$):1.05(3H, d, J=6.0), 1.19(3H, d, J=6.0), 3.75(3H, s), 4.14–4.23(1H, m), 5.89(2H, s), 6.32(1H, s), 6.69(2H, d, J=8.1), 6.80–6.88(6H, m), 6.98(2H, d, J=9.0), 10.09(1H, s)

Analysis for: C27H24O7

Calculated: C,70.42; H,5.25

Found: C,70.19; H,5.34

(Step 2) 2-(Benzo[1,3]dioxol-5-yl-6-isopropoxy-4-(4-methoxy-phenoxy)-2H-chromen-3-carboxylic acid (I-74)

An aqueous solution (1.16 ml) of sodium dihydrogen phosphate (466 mg) followed by an aqueous solution (1 ml) of sodium chlorite (80% purity, 65 mg) were added to a stirred solution of compound (XII-1) (100 mg, 0.217 mmol) in DMF (7 ml) at ice-bath temperature. After 3.5 h, an aqueous solution (1 ml) of sodium chlorite (80% purity, 65 mg) was added and the mixture was stirred for 16 h. Water was added to the reaction mixture and the layers were extracted twice with ethyl acetate. An ethyl acetate layer was washed with water and brine and dried over magnesium sulfate. The solvent was removed under reduced pressure, and the residue was recrystallized from ethyl acetate/hexane to give compound (I-74) (148 mg, 82%) as yellow crystals.

Example 6 2-(Benzo[1,3]dioxol-5-yl)-4-butylsulfanyl-6-isopropoxy-2H-chromen-3-carboxylic acid (I-89)

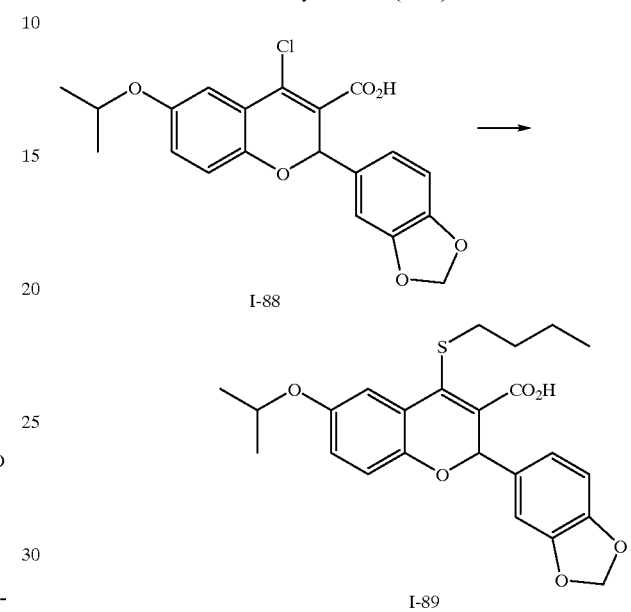

I-88

I-89

To an ice-cooled suspension of sodium hydride (60% oil dispersion, 84 mg, 2.10 mmol) in anhydrous THF (1 ml) was added n-butylmercaptan (0.129 ml, 1.20 mmol). After being stirred for 30 min at ambient temperature, the reaction mixture was cooled in an ice-bath again and a solution of compound (I-88) (382 mg, 0.983 mmol) in anhydrous THF (6 ml) was added dropwise. Stirring was continued for 30 min at ambient temperature, 0.2 ml of acetic acid was added and the solvent was removed under reduced pressure. Water was added to the residue and the mixture was extracted twice with ethyl acetate. An ethyl acetate layer was washed with water and brine, dried over magnesium sulfate, and concentrated. The residue was chromatographed on silica gel (10 g) eluting with ethyl acetate/hexane=1:9 then 1:4. Compound (I-89) was obtained as yellow crystals after recrystallization from isopropylalcohol-hexane(33 mg, 15%).

Example 7 Methyl 2-(benzo[1,3]dioxol-5-yl)-6-isopropoxy-4-(4-methoxy-phenyl)-2H-chromen-3-carboxylate (Ia-10)

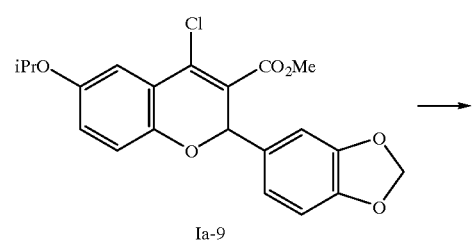

Ia-9

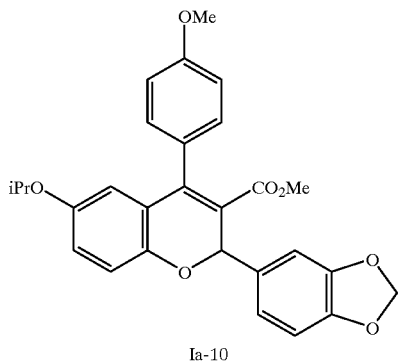

Ia-10

A mixture of compound (Ia-9) (105 mg, 0.261 mmol), N-methylpyrrolidinone (1.0 ml) and ferric chloride (10 mg) in anhydrous THF (1.0 ml) was cooled to 5° C. and 1 M solution of p-methoxyphenylmagnesium bromide in THF (0.76 ml) was added and stirred for 1 h. The reaction mixture was poured into an aqueous solution of ammonium chloride and extracted with toluene. An organic layer was washed with water, dried, and concentrated. The residue was purified by silica gel chromatography (toluene/ethyl acetate =95:5) to give the compound (Ia-10) (42 mg, 35%).

Example 8 2-(Benz[1,3]dioxol-5-yl)-6-isopropoxy-4-(4-methoxy-phenyl)-2H-chromen-3-carboxylic acid (I-36)

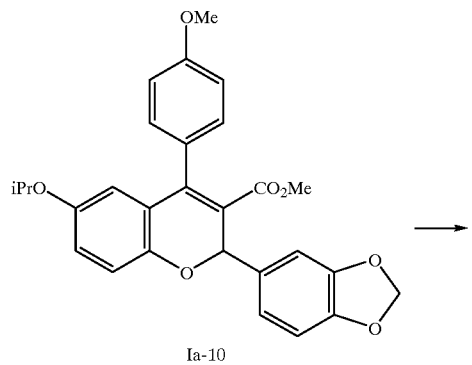

Ia-10

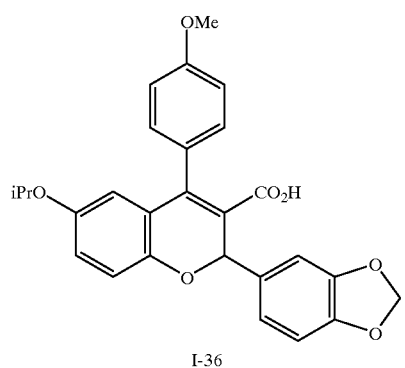

I-36

A solution of compound (Ia-10) in THF (4 ml) and methanol(4 ml) was refluxed with 1M aqueous solution of sodium hydroxide (4.2 ml) for 3 h. The solvent was removed under reduced pressure and water was added. The mixture was acidified with hydrochloric acid and extracted three times with ether. An ether layer was washed with water and brine, dried over magnesium sulfate, and concentrated. The residue was recrystallized from 95% ethanol to give the compound (I-36) as yellow crystals (254 mg, 66%).

Example 9 2-(Benzo[1,3]dioxol-5-yl)-4-cyclopentyl-6-isopropoxy-2H-chromen-3-carboxylic acid (I-79)

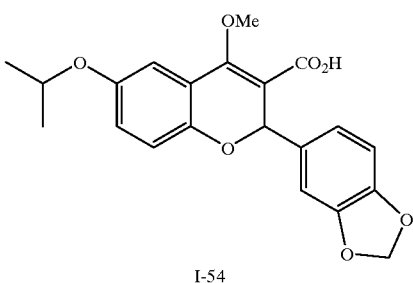

I-54

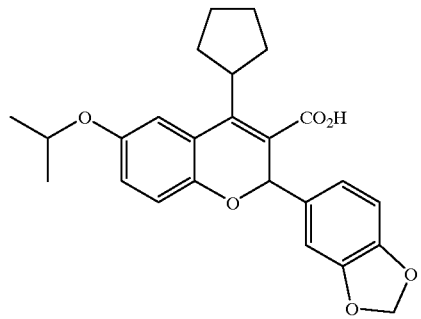

I-79

A solution of compound (I-54) (192 mg, 0.50 mmol) in anhydrous THF (2.5 ml) was added dropwise to Grignard reagent, prepared from magnesium turnings(53 mg, 2.18 mmol) and cyclopentyl bromide (298 mg, 2.00 mmol) in anhydrous THF (2.5 ml), at −30° C. over 5 min. The mixture was allowed to warm to 0° C. over a period of 1 h with stirring and the reaction was continued for 2 h at 2° C. Acetic acid (0.15 ml) was added and the solvent was removed under reduced pressure. Ice water was added to the residue and the layers were extracted with ethyl acetate. An organic layer was washed with water and brine, dried over magnesium sulfate then concentrated under reduced pressure. The residue was purified by silica gel (9 g) chromatography (ethyl acetate/hexane=1:4) to give compound (I-79) as a yellow solid (162 mg). Recrystallization from diisopropylether gave yellow crystals (112 mg, 53%).

IR(Nujol): 2551, 1674 (C=O)

Example 10 2-(Benzo[1,3]dioxol-5-yl)-6-isopropoxy-4-(4-methoxy-benzyl)-2H-chromen-3-carboxylic acid (I-81)

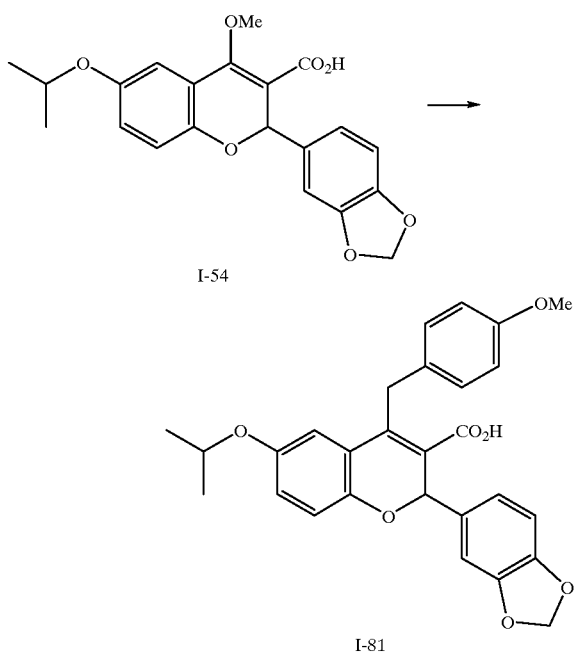

A solution of compound (I-54) in anhydrous THF (3 ml) was added dropwise to Grignard reagent prepared from magnesium (53 mg, 2.18 mmol) and 4-methoxy benzyl bromide (313 mg, 2.00 mmol) in anhydrous THF (0.5 ml), at −33° C. to −27° C. over 5 min. The mixture was warmed to 2° C. over 1 h period and stirring was continued for 3 h at the same temperature. Acetic acid (0.15 ml) was added and the solvent was removed under reduced pressure. Ice water was added to the residue and and the layers were extracted with ethyl acetate. An organic layer was washed with water and brine and dried over magnesium sulfate. The solvent was removed under reduced pressure and the residue was purified by silica gel (15 g) chromatography eluting with ethyl acetate/hexane=1:4 then 1:2. Compound (I-81) (102 mg) was obtained as a yellow solid which was recrystallized from diisopropylether to give yellow prisms (82 mg, 34%).

IR(Nujol): 2633, 1683 (C=O)

Example 11 2-(Benzo[1,3]dioxol-5-yl)-6-isopropoxy-4-pentyl-2H-chromen-3-carboxylic acid (I-77)

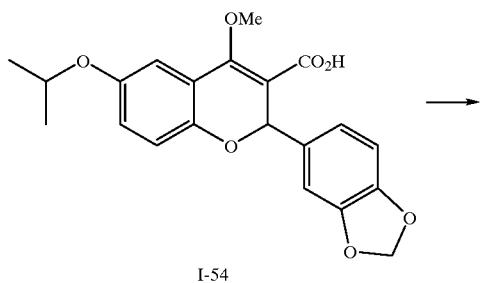

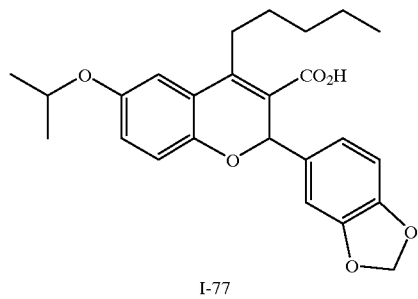

After a solution of amyl bromide (302 mg, 2.00 mmol) in anhydrous THF (2 ml) was added dropwise to magnesium (53 mg, 2.18 mmol), the mixture was heated to reflux for 30 min. The reaction mixture was cooled to −35° C. and a solution of compound (I-54) (192 mg, 0.50 mmol) in anhydrous THF (3 ml) was added dropwise over 5 min. After stirring at the same temperature for 1 h, the solution was allowed to warm to 0° C. and stirred for further 2 h. To the reaction mixture was added to 0.15 ml of glacial acetic acid and the solvent was removed under reduced pressure. Water was added to the residue and the layers were extracted twice with ethyl acetate. An ethyl acetate layer was washed with water and brine, dried over magnesium sulfate, and the solvent removed under reduced pressure. The residue was purified by 9 g of silica gel, eluting with ethyl acetate/hexane=1:4 then 1:2 to give the compound (I-77) (151 mg, 71%) as yellow crystals.

Example 12 2-(Benzo[1,3]dioxol-5-yl)-6-isopropoxy-4-(5-methyl-thiophen-2-yl)-2H-chromen-3-carboxylic acid (I-80)

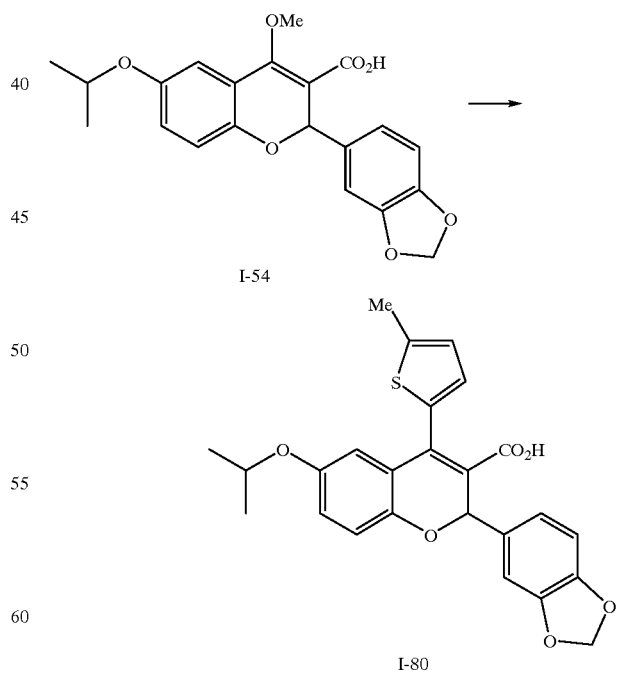

In a similar manner as the Example 11, the compound (I-80) was synthesized by reacting the compound (I-54) with Grignard reagent prepared from 2-bromo-5-methylthiophen.

Example 13 Methyl 2-(benzo[1,3]dioxol-5-yl)-6-butoxy-4-isopropoxy-2H-chromen-3-carboxylate (Ia-11)

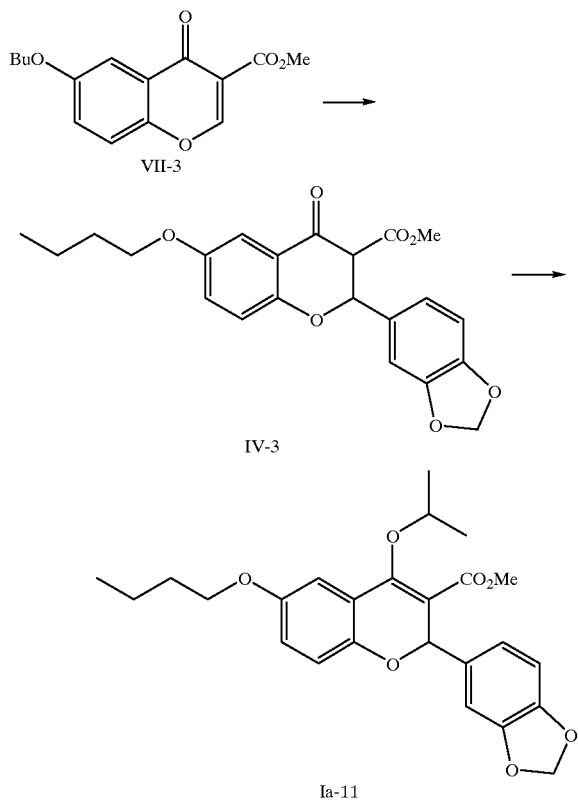

The compound (VII-3) was converted to methyl 2-(benzo[1,3]dioxol-5-yl)-6-butoxy- 4-oxo-chroman-3-carboxylate (IV-3) by a similar method as Step 5 of Reference Example 2. Compound (V-3) (250 mg, 0.628 mmol), triphenylphosphine (247 mg, 0.943 mmol) and isopropanol (57 mg, 0.943 mmol) were dissolved in 7 ml of THF and cooled to −10° C. A solution of diethylazodicarboxylate (164 mg, 0.943 mmol) in THF (2 ml) was added dropwise and stirred for 2 h at the same temperature. After the solvent was removed under reduced pressure, the residue was purified by 10 g of silica gel chromatography (ethyl acetate/hexane=1:4) to give the compound (Ia-11) (220 mg, 80%) as a yellow oil.

Example 14 2-(Benzo[1,3]dioxol-5-yl)-6-butoxy-4-isopropoxy-2H-chromen-3-carboxylic acid (I-61)

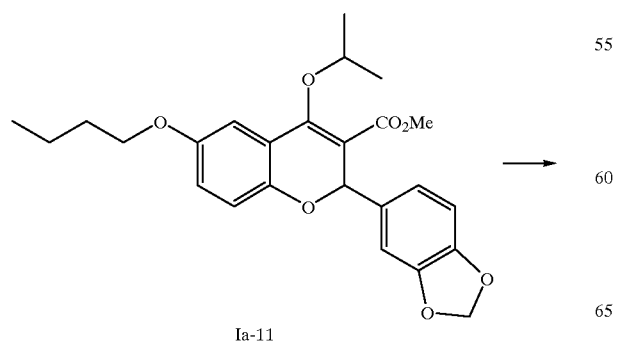

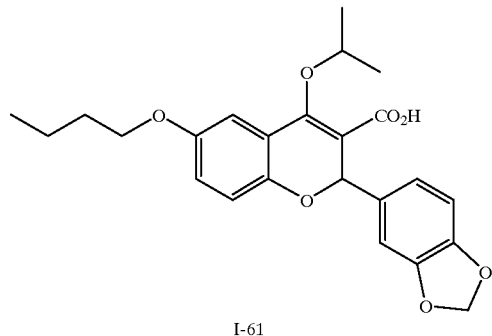

Compound (Ia-11)(210 mg, 0.477 mol) and 1 M aqueous solution of sodium hydroxide in THF (3 ml) and methanol(3 ml) were refluxed for 3 h. After the solvent was removed under reduced pressure, the residue was dissolved in water, acidified with hydrochloric acid, and extracted with ether three times. The ether layer was washed with water and brine and dried over magnesium sulfate. The solvent was removed under reduced pressure and the residue was recrystallized from 95% ethanol to give the compound (I-61) as yellow crystals (148 mg, 72%).

Example 15 Methyl 2-(benzo[1,3]dioxol-5-yl-6-isopropoxy-4-(4-pentenyloxy-1-yl)-2H-chromen-3-carboxylate (Ia-13)

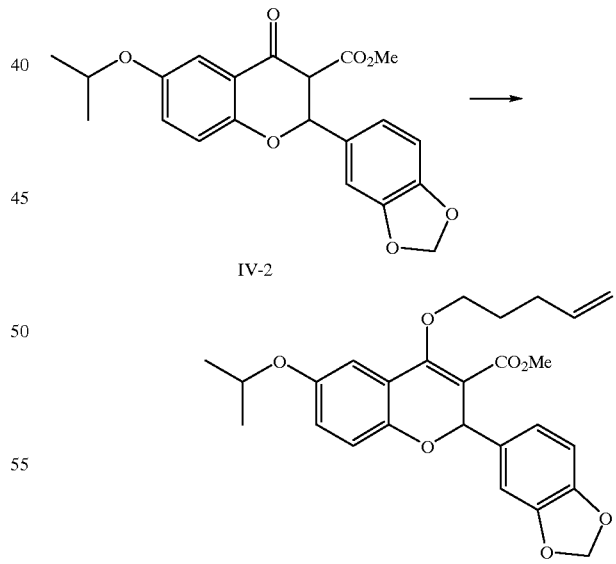

The compound (IV-2) and 4-penten-1-ol were reacted in a similar manner as described in Example 13 to give the compound (Ia-13).

Example 16 2-(Benzo[1,3]dioxol-5-yl)-6-isopropoxy-4-(4-pentenyloxy-1-yl)-2H-chromen-3-carboxylic acid (I-65)

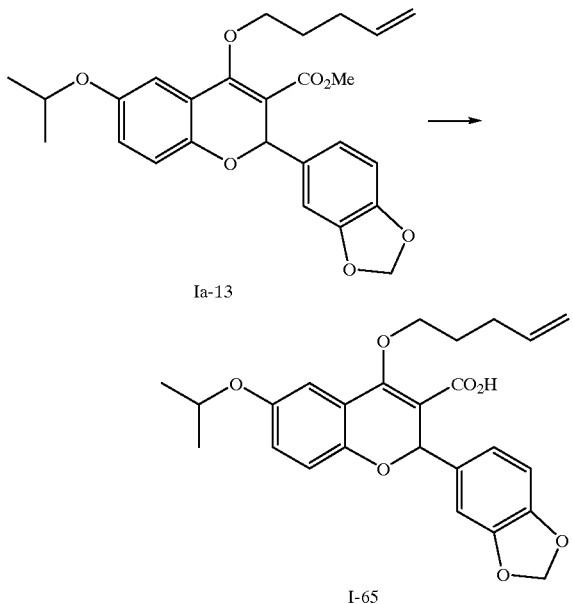

The compound (Ia-13) was hydrolyzed with alkaline in a similar manner as the Example 14 to give the compound (I-65).

Example 17 Methyl 2-(benzo[1,3]dioxol-5-yl)-4-(butyl-methyl-amino)-6-isopropoxy-2H-chromen-3-carboxylate (Ia-12)

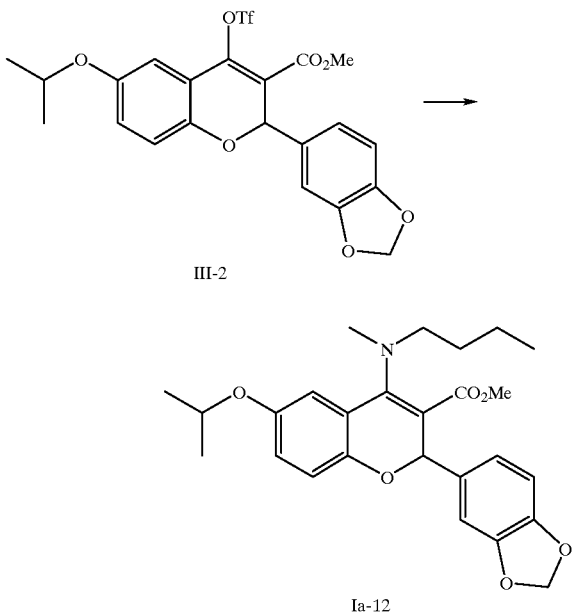

A mixture of compound (III-2) (200 mg, 0.387 mmol), butylamine (101 mg, 1.16 mmol) and THF (2 ml) was stirred for 3 h at ambient temperature. Water was added and the layers were extracted with ether three times. The ether layer was washed with water and brine and dried over magnesium sulfate. After the solvent was removed under reduced pressure, the residue was purified on 2 g of silica gel column and ethyl acetate/hexane=1:2 to give the compound (Ia-12) (176 mg, 100%) as a yellow oil.

Example 18 Methyl 6-benzyloxy-2,4-di(benzo[1,3]dioxol-5-yl)-2H-chromen-3-carboxylate (Ia-1)

A mixture of compound (III-1) (530 mg, 0.939 mmol), 3,4-methylenedioxyphenyl boric acid (218 mg, 1.314 mmol), tetrakis(triphenylphosphine)palladium (0) (22 mg, 0.02 mmol), lithium chloride (119 mg, 2.82 mmol), and 2 M aqueous solution of sodium carbonate (1.3 ml) in DME (5 ml) was refluxed for 2 h. The mixture was extracted with ether three times, and the organic layer was washed with 2 M aqueous solution of sodium carbonate, water and brine, and dried over magnesium sulfate. The solvent was removed under reduced pressure and the residue was purified by 25 g of silica gel chromatography (ethyl acetate/hexane=1:3). Compound (Ia-1) (481 mg, 95%) was obtained as yellow solid.

The solid was recrystallization from ethyl acetate/hexane to give pale yellow crystals.

Example 19 Methyl 2.4-di(benzo[1,3]dioxol-5-yl)-6-hydroxy-2H-chromen-3-carboxylate (Ia-2)

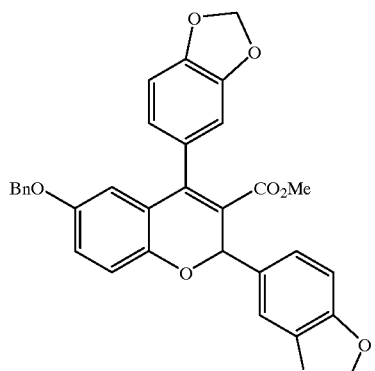

Ia-1

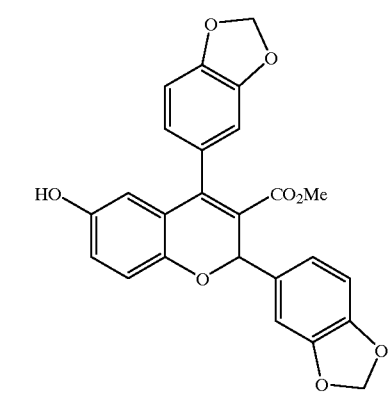

Ia-2

The compound (Ia-1) (310 mg, 0.593 mmol) was stirred with 10% palladium/carbon (20 mg) in glacial acetic acid (3 ml) under atmosphere of hydrogen for 24 h. The catalyst was removed through a pad of celite and the filtrate was concentrated under reduced pressure. The residue was purified by 30 g of silica gel chromatography (ethyl acetate/hexane= 1:3) to give the compound (Ia-2) (234 mg, 88%) as an yellow oil.

Example 20 Methyl 2,4-di(benzo[1,3]dioxol-5-yl)-6-isopropoxy-2H-chromen-3-carboxylate (Ia-3)

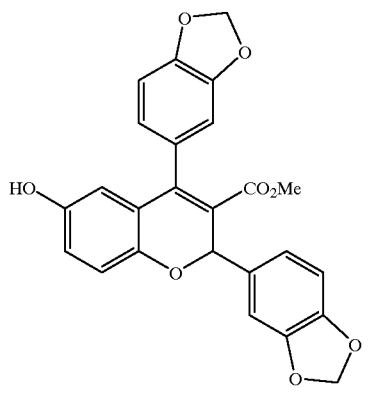

Ia-2

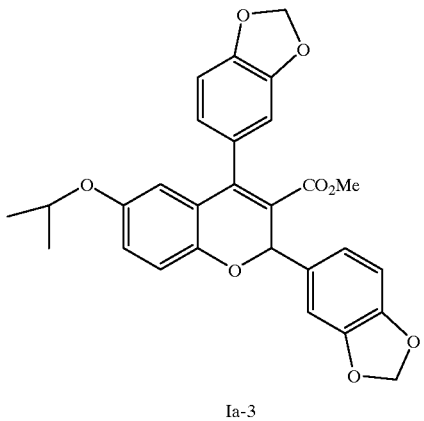

Ia-3

The compound (Ia-2) (100 mg, 0.224 mmol), 2-bromopropane (33 mg, 0.269 mmol) and potassium carbonate (74 mg, 0.57 mmol) were stirred in DMF (2 ml) at 100° C. for 3 days. Water was added to the reaction mixture and the layers were extracted with ether three times. The combined ether layers were washed with water and brine and dried over magnesium sulfate. The solvent was removed under reduced pressure and the residue was purified by 7.5 g of silica gel chromatography (ethyl acetate/hexane=1:3) to give the compound (Ia-3) (57 mg, 52%) as an yellow oil.

Example 21 2,4-Di(benzo[1,3]dioxol-5-yl)-6-isopropoxy-2H-chromen-3-carboxylic acid (I-1)

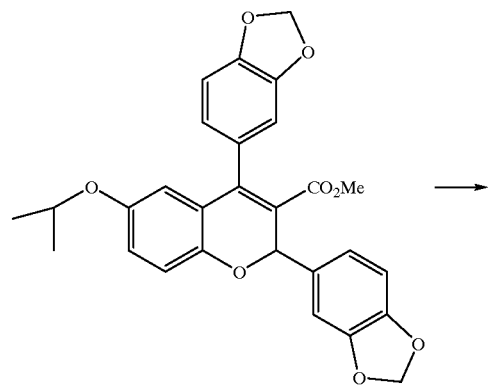

Ia-3

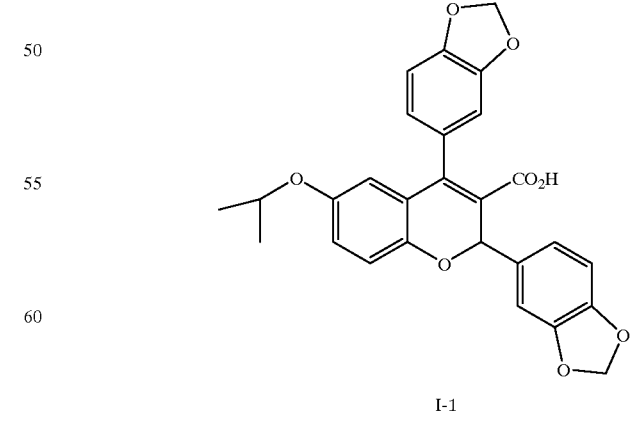

I-1

A mixture of compound (Ia-3) (57 mg, 0.117 mmol) and 1 M aqueous solution of sodium hydroxide (1.2 ml) in THF (2 ml) and methanol (2 ml) were refluxed for 1 h. The solvent was removed under reduced pressure, acidified with hydrochloric acid and extracted with ether three times. The ether layers were combined, washed with water and brine, dried over magnesium sulfate, and concentrated under reduced pressure. The residue was recrystallized from acetone-isopropylether to give compound (I-1) (37 mg, 66%) as yellow crystals.

Example 22 Methyl 2-(benzo[1,3]dioxol-5-yl)-4-(4-methoxy-phenyl)-chroman-3-carboxylate (Ib-1)

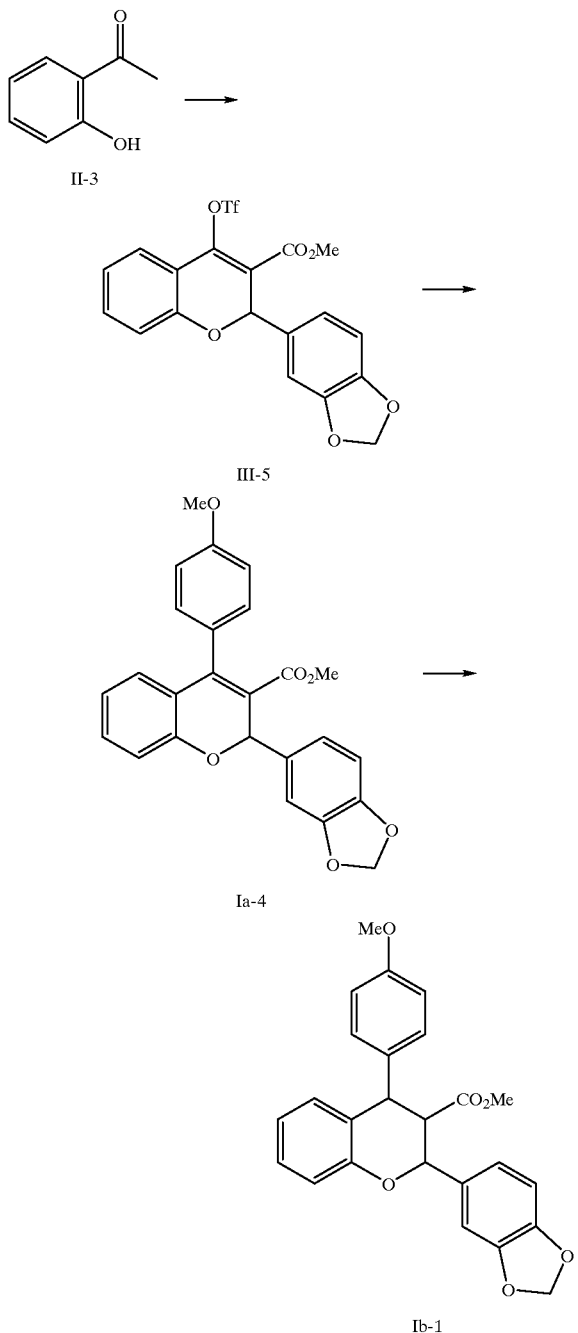

3-carboxylate (III-5) synthesized from the compound (II-3) by a similar method as described in Reference Example 2 were reacted in a similar manner as described in Example 18 to give methyl 2-(benzo[1,3]dioxol-5-yl)-4-(4-methoxy-phenyl)-2H-chromen-3-carboxylate (Ia-4).

(Step 2)

The compound (Ia-4) (100 mg, 0.240 mmol) was hydrogenated over 5% palladium/carbon (10 mg) in a mixture of ethyl acetate (4 ml), acetic acid (1 ml), and THF (2 ml). The catalyst was filtered off and the filtrate concentrated under reduced pressure to leave a colorless solid. Recrystallization from diisopropylether-acetone afforded the compound (Ib-1) (56 mg, 56%) as colorless crystals.

Example 23 2-(Benzo[1,3]dioxol-5-yl)-4-(4methoxy-phenyl)-chroman-3-carboxyl i acid (I-2)

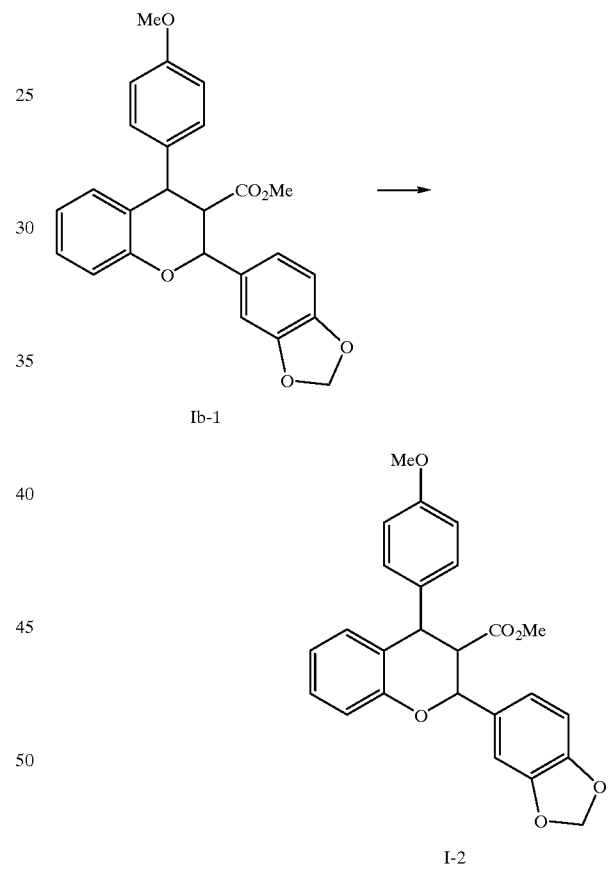

(Step 1)

4-Methoxyphenyl boric acid and methyl 2-(benzo[1,3]dioxol-5-yl)-4-(trifluoromethanesulfonyloxy)-2H-chromen- The compound (Ib-1) (72 mg, 0.172 mmol) and 1 M aqueous solution of sodium hydroxide (0.52 ml, 0.52 mol) in methanol (2 ml) and THF (1 ml) were refluxed for 10 h. The solvent was removed under reduced pressure and water was added to the residue. The aqueous layer was acidified with hydrochloric acid and extracted with ethyl acetate three times. The organic layer was washed with brine, dried over magnesium sulfate, and the solvent removed under reduced pressure. The residue was recrystallized from methanol to give the compound (I-2) (59 mg, 84) as colorless crystals.

Example 24 Methyl 2,4-(dibenzo[1,3]dioxol-5-yl)-6-isopropoxy-chroman-3-carboxylate (Ib-2)

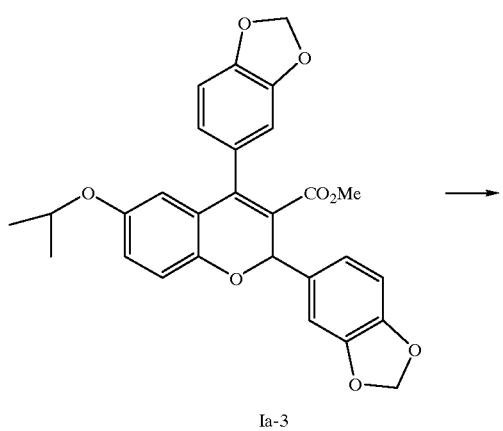

Ia-3

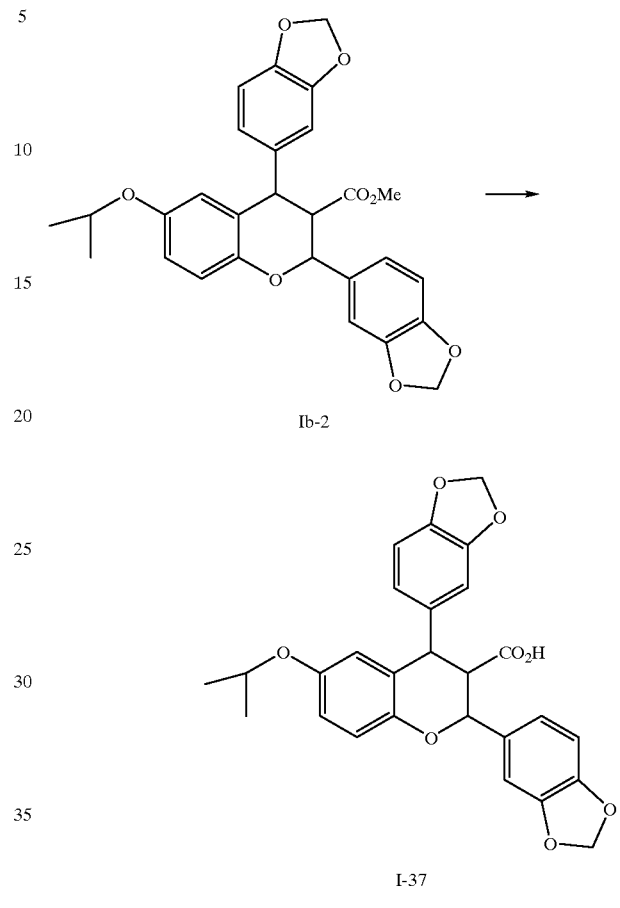

Ib-2

The compound (Ia-3) (1.0 mg, 0.002 mmol) and palladium chloride (660 mg) were rigourously stirred in methanol (60 ml) and chloroform (20 ml) under 5 atm of hydrogen atomsphere for 3 days at ambient temperature. The insoluble materials were separated by filtration and throughly washed with methanol. The precipitates were eluted with chloroform to give the compound (Ib-2) (300 mg). The filtrate was combined and the solvent removed. The precipitate was collected and washed with methanol to give additional crop of compound (Ib-2) (261 mg). Total 561 mg (57%).

IR (Nujol ν max cm$^{-1}$): 2952, 2923, 2855, 1729, 1707, 1488, 1251, 1209

Example 25 2.4-(Dibenzo[1,3]dioxol-5-yl)-6-isopropoxy-chroman-3-carboxylic acid (I-37)

The compound (Ib-2) (48.2 mg, 0.2 mmol) was dissolved in DMSO (6 ml) and stirred with 1 M aqueous solution of sodium hydroxide at 90° C. for 1 h. Then, the mixture was adjusted to pH 3 by adding water and dilute hydrochloric acid and extracted with ethyl acetate. The organic layer was washed with water three times, brine once, and dried over sodium sulfate. The solvent was removed under reduced pressure and the residue was purified by column chromatography on silica gel (methanol/chloroform=1:40 to 1:10) to give the compound (I-37) (32.8 mg, 34%). IR (Nujol ν max cm$^{-1}$): 3600–2400 (br), 2924, 2855, 1729, 1692, 1488, 1446, 1247,

Example 26 (+)-2.4-Di(benzo[1,3]dioxol-5-yl)-6-isopropoxy-2H-chromen-3-carboxylic acid ((+)-I-1)

A salt prepared from the compound (I-1) (30.0 g, 63.23 mmol) and (R)-(+)-phenylethylamine (7.66 g, 63.23 mmol) was recrystallized from 95% ethanol twice to give 12.36 g (66%) of an amine salt as white crystals.

m.p. 167–171 (dec.)

[α]D+95.0 (c1.00, MeOH)

The salt was suspended in water and 1 M hydrochloric acid (22 ml) was added under ice-cooling and the liberated acid was extracted with ether three times. The ether layer was washed with water and brine and dried over magnesium sulfate. The solvent was removed and the residue was recrystallized from ethyl acetate/hexane=1:1 to give (+)-I-1 (7.88 g, 53%) as yellow crystals.

m.p. 131.5–134.5° C.

[α]D +168.9 (c1.00, MeOH)

Example 27 (−)-2,4-Di(benzo[1,3]dioxol-5-yl)-6-isopropoxy-2H-chromen-3-carboxylic acid (−)-I-1)

The titled compound was obtained in a similar method as Example 26 except that (S)-(−)-phenylethylamine was used as resolving reagent.

m.p. 131–133° C.

[α]D −168.2 (c1.00, MeOH)

Example 28 (+)-2-(Benzo[1,3]dioxol-5-yl)-6-isopropoxy-4-(4-methoxyphenyl)-2H-chromen-3-carboxylic acid ((+)-I-36)

m.p. 158° C., 171.5–173.0° C.

[α]D +178.8 (c1.00, MeOH)

Example 29 (−)-2-(Benzo[1,3]dioxol-5-yl)-6-isopropoxy-4(4-methoxyphenyl)-2H-chromen-3-carboxylic acid ((−)-I-36)

m.p. 158° C., 170–171° C.

[α]D −177.3 (c1.01, MeOH)

Example 30 (+)-2-(Benzo[13]dioxol-5-yl)-6-isopropoxy-4-methoxy-2H-chromen-3-carboxylic acid ((+)-I-54)

m.p. 127–128.5° C.

[α]D +51.0 (c1.00, MeOH)

Example 31 (+2-(Benzo[1,3]dioxol-5-yl)-4-butyl-6-isopropyl-2H-chromen-3-carboxylic acid ((+)-I-76)

The compound (+)-I-54 was converted to the compound (+)-I-76 in a similar method as Example 11.

m.p. 148–149° C.

[α]D +61.3 (c1.00, MeOH)

The following compounds (1) were synthesized in a similar manner as described in any one of the above Examples.

TABLE 1

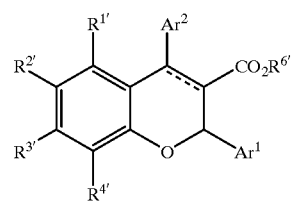

(I')

| Compound No. | $R^{1'}$ | $R^{2'}$ | $R^{3'}$ | $R^{4'}$ | $R^{6'}$ | $^{*1}Ar^1$ | $^{*1}Ar^2$ | presence or absence of a bond |
|---|---|---|---|---|---|---|---|---|
| I-1 | H | OiPr | H | H | H | 3,4-MD-Ph | 3,4-MD-Ph | Presence |
| I-2 | H | H | H | H | H | 3,4-MD-Ph | 4-OMe—Ph | Absence |
| I-3 | H | H | H | H | H | 3,4-MD-Ph | 3,4-MD-Ph | Presence |
| I-4 | H | H | H | H | H | 3,4-MD-Ph | 4-OMe—Ph | Presence |
| I-5 | H | H | H | H | H | 3,4-MD-Ph | 2-OMe—Ph | Presence |
| I-6 | H | H | H | H | H | 3,4-MD-Ph | 3-OMe—Ph | Presence |
| I-7 | H | H | H | H | H | 3,4-MD-Ph | 3,4,5-OMe—Ph | Presence |
| I-8 | H | H | H | H | H | 3,4-MD-Ph | 4-Cl—Ph | Presence |
| I-9 | H | H | H | H | H | 3,4-MD-Ph | 4-Me—Ph | Presence |
| I-10 | H | H | H | H | H | 3,4-MD-Ph | 4-nPr—Ph | Presence |
| I-11 | H | H | H | H | H | 3,4-MD-Ph | Ph | Presence |
| I-12 | H | H | H | H | H | 3,4-MD-Ph | 4-iPr—Ph | Presence |
| I-13 | H | H | H | H | H | 3,4-MD-Ph | 4-NMe$_2$—Ph | Presence |
| I-14 | H | H | H | H | H | 4-OMe—Ph | 3,4-MD-Ph | Absence |
| I-15 | OnPr | H | H | H | H | 3,4-MD-Ph | 3,4-MD-Ph | Presence |
| I-16 | H | OnPr | H | H | H | 3,4-MD-Ph | 3,4-MD-Ph | Presence |
| I-17 | H | OCH$_2$cPr | H | H | H | 3,4-MD-Ph | 3,4-MD-Ph | Presence |
| I-18 | H | OBn | H | H | H | 3,4-MD-Ph | 3,4-MD-Ph | Presence |
| I-19 | H | H | OnPr | H | H | 3,4-MD-Ph | 3,4-MD-Ph | Presence |
| I-20 | OnPr | H | H | H | H | 3,4-MD-Ph | 4-OMe—Ph | Presence |
| I-21 | H | OnPr | H | H | H | 3,4-MD-Ph | 4-OMe—Ph | Presence |
| I-22 | H | OEt | H | H | H | 3,4-MD-Ph | 4-OMe—Ph | Presence |
| I-23 | H | OnBu | H | H | H | 3,4-MD-Ph | 4-OMe—Ph | Presence |
| I-24 | H | OH | H | H | H | 3,4-MD-Ph | 4-OMe—Ph | Presence |
| I-25 | H | H | OnPr | H | H | 3,4-MD-Ph | 4-OMe—Ph | Presence |
| I-26 | H | H | H | nPr | H | 3,4-MD-Ph | 4-OMe—Ph | Presence |
| I-27 | H | H | H | H | H | 3,4-MD-Ph | 2-OCH$_2$CO$_2$H-4-OMe—Ph | Presence |
| I-28 | OnPr | H | H | H | H | 4-OMe—Ph | 3,4-MD-Ph | Presence |

TABLE 1-continued (I')

$$\text{structure with } R^{1'}, R^{2'}, R^{3'}, R^{4'} \text{ on benzene ring fused to pyran bearing } Ar^1, Ar^2, CO_2R^{6'}$$

| Compound No. | $R^{1'}$ | $R^{2'}$ | $R^{3'}$ | $R^{4'}$ | $R^{6'}$ | *¹$Ar^1$ | *¹$Ar^2$ | presence or absence of a bond |
|---|---|---|---|---|---|---|---|---|
| I-29 | H | OnPr | H | H | H | 4-OMe—Ph | 3,4-MD-Ph | Presence |
| I-30 | H | H | OnPr | H | H | 4-OMe—Ph | 3,4-MD-Ph | Presence |

TABLE 2

| Compound No. | $R^{1'}$ | $R^{2'}$ | $R^{3'}$ | $R^{4'}$ | $R^{6'}$ | *¹$Ar^1$ | *¹$Ar^2$ | Presence or absence of a bond |
|---|---|---|---|---|---|---|---|---|
| I-31 | H | H | OnPr | H | H | 4-OMe-Ph | 3,4-MD-Ph | Absence |
| I-32 | H | H | H | nPr | H | 4-OMe-Ph | 3,4-MD-Ph | Presence |
| I-33 | H | H | OnPr | H | H | 4-OMe-Ph | 4-ipr-Ph | Presence |
| I-34 | H | H | H | H | H | 3,4-MD-Ph | 2-Th | Presence |
| I-35 | H | H | H | H | H | 4-OMe-Ph | 3,4-MD-Ph | Presence |
| I-36 | H | OiPr | H | H | H | 3,4-MD-Ph | 4-OMe-Ph | Presence |
| Ia-1 | H | OBn | H | H | Me | 3,4-MD-Ph | 3,4-MD-Ph | Presence |
| Ia-2 | H | OH | H | H | Me | 3,4-MD-Ph | 3,4-MD-Ph | Presence |
| Ia-3 | H | OiPr | H | H | Me | 3,4-MD-Ph | 3,4-MD-Ph | Presence |
| Ia-4 | H | H | H | H | Me | 3,4-MD-Ph | 4-OMe-Ph | Presence |
| Ia-6 | H | OiPr | H | H | Et | 3,4-MD-Ph | 4-OMe-Ph | Presence |
| Ia-8 | H | OiPr | H | H | iPr | 3,4-MD-Ph | 4-OMe-Ph | Presence |
| Ia-10 | H | OiPr | H | H | Me | 3,4-MD-Ph | 4-OMe-Ph | Presence |
| Ib-1 | H | H | H | H | Me | 3,4-MD-Ph | 4-OMe-Ph | Absence |
| I-37 | H | OiPr | H | H | H | 3,4-MD-Ph | 3,4-MD-Ph | Absence |
| I-38 | H | OiPr | H | H | H | 3,4-MD-Ph | 4-iPr-Ph | Presence |
| I-39 | H | OiPr | H | H | H | 4-OMe-Ph | 4-OMe-Ph | Presence |
| I-40 | H | OiPr | H | H | H | 4-OMe-Ph | 3,4-MD-Ph | Presence |
| I-41 | H | OiPr | H | H | H | 4-iPr-Ph | 4-OMe-Ph | Presence |
| I-42 | H | OiPr | H | H | H | 4-iPr-Ph | 3,4-MD-Ph | Presence |
| I-43 | H | OCH$_2$CHMe$_2$ | H | H | H | 3,4-MD-Ph | 3,4-MD-Ph | Presence |
| I-44 | H | O(CH$_2$)$_2$CHMe | H | H | H | 3,4-MD-Ph | 3,4-MD-Ph | Presence |
| I-45 | H | O(CH$_2$)$_3$CHM$_2$ | H | H | H | 3,4-MD-Ph | 3,4-MD-Ph | Presence |
| I-46 | H | O(CH$_2$)$_2$cPr | H | H | H | 3,4-MD-Ph | 3,4-MD-Ph | Presence |
| I-47 | H | O(CH$_2$)$_2$CMe$_3$ | H | H | H | 3,4-MD-Ph | 3,4-MD-Ph | Presence |
| I-48 | H | OCH$_2$CHEt$_2$ | H | H | H | 3,4-MD-Ph | 3,4-MD-Ph | Presence |
| I-49 | H | OCHEt$_2$ | H | H | H | 3,4-MD-Ph | 3,4-MD-Ph | Presence |
| I-50 | H | OCHnPr$_2$ | H | H | H | 3,4-MD-Ph | 3,4-MD-Ph | Presence |
| I-51 | H | OcPent | H | H | H | 3,4-MD-Ph | 3,4-MD-Ph | Presence |
| I-52 | H | O(CH$_2$)$_2$NMe$_2$ | H | H | H | 3,4-MD-Ph | 3,4-MD-Ph | Presence |

TABLE 3

(I-O)

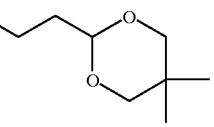

| Compound No. | R¹ | R² | R³ | R⁴ | *¹R⁵ | R⁶ | *¹R⁷ | Presence or absence of a bond |
|---|---|---|---|---|---|---|---|---|
| I-53 | H | OiPr | H | H | 3,4-MD-Ph | H | H | Presence |
| I-54 | H | OiPr | H | H | 3,4-MD-Ph | H | OMe | Presence |
| I-55 | H | OiPr | H | H | 3,4-MD-Ph | H | OEt | Presence |
| I-56 | H | OiPr | H | H | 3,4-MD-Ph | H | OnPr | Presence |
| I-57 | H | OiPr | H | H | 3,4-MD-Ph | H | OnBu | Presence |
| I-58 | H | OiPr | H | H | 3,4-MD-Ph | H | OnPent | Presence |
| I-59 | H | OiPr | H | H | 3,4-MD-Ph | H | OiPr | Presence |
| I-60 | H | OiPr | H | H | 3,4-MD-Ph | H | OCH$_2$cPr | Presence |
| I-61 | H | OnBu | H | H | 3,4-MD-Ph | H | OiPr | Presence |
| I-62 | H | H | OnPr | H | 3,4-MD-Ph | H | OnBu | Presence |
| I-63 | OnPr | H | H | H | 3,4-MD-Ph | H | OnBu | Presence |
| I-64 | H | OiPr | H | H | 3,4-MD-Ph | H | O(CH$_2$)$_9$CH$_3$ | Presence |
| I-65 | H | OiPr | H | H | 3,4-MD-Ph | H | O(CH$_2$)$_3$CH=CH$_2$ | Presence |
| I-66 | H | OiPr | H | H | 3,4-MD-Ph | H | 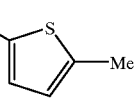 | Presence |
| I-67 | H | OiPr | H | H | 3,4-MD-Ph | H | OnHex | Presence |
| I-68 | H | OiPr | H | H | 3,4-MD-Ph | H | O(CH$_2$)$_5$OH | Presence |
| I-69 | H | OiPr | H | H | 3,4-MD-Ph | H | O(CH$_2$)$_3$CN | Presence |
| I-70 | H | OiPr | H | H | 3,4-MD-Ph | H | O(CH$_2$)$_3$CH(OMe)$_2$ | Presence |
| I-71 | H | OiPr | H | H | 3,4-MD-Ph | H | O(CH$_2$)$_3$CHO | Presence |
| I-72 | H | OiPr | H | H | 3,4-MD-Ph | H | OnHep | Presence |
| I-73 | H | H | H | nPr | 3,4-MD-Ph | H | OnBu | Presence |
| I-74 | H | OiPr | H | H | 3,4-MD-Ph | H | OPh-4-OMe | Presence |
| I-75 | H | OnBu | H | H | 3,4-MD-Ph | H | O(CH$_2$)$_2$Ph-4-OMe | Presence |
| I-76 | H | OiPr | H | H | 3,4-MD-Ph | H | nBu | Presence |
| I-77 | H | OiPr | H | H | 3,4-MD-Ph | H | nPent | Presence |
| I-78 | H | OiPr | H | H | 3,4-MD-Ph | H | iPr | Presence |
| I-79 | H | OiPr | H | H | 3,4-MD-Ph | H | cPent | Presence |
| I-80 | H | OiPr | H | H | 3,4-MD-Ph | H | 2,5-dimethylthiophene | Presence |

TABLE 4

| Compound No. | R¹ | R² | R³ | R⁴ | *¹R⁵ | R⁶ | *¹R⁷ | Presence or absence of a bond |
|---|---|---|---|---|---|---|---|---|
| I-81 | H | OiPr | H | H | 3,4-MD-Ph | H | 4-OMe—Bn | Presence |
| I-82 | H | OiPr | H | H | 3,4-MD-Ph | H | nHex | Presence |
| I-83 | H | OiPr | H | H | 3,4-MD-Ph | H | (CH$_2$)$_2$CHMe$_2$ | Presence |
| I-84 | H | OiPr | H | H | 3,4-MD-Ph | H | (CH$_2$)$_3$OCH$_3$ | Presence |
| I-85 | H | OiPr | H | H | 3,4-MD-Ph | H | CH$_2$-cHex | Presence |
| I-86 | H | OiPr | H | H | 3,4-MD-Ph | H | (CH$_2$)$_2$CH=CH$_2$ | Presence |
| I-87 | H | OiPr | H | H | 3,4-MD-Ph | H | (CH$_2$)$_4$OH | Presence |
| I-88 | H | OiPr | H | H | 3,4-MD-Ph | H | Cl | Presence |
| I-89 | H | OiPr | H | H | 3,4-MD-Ph | H | S-nBu | Presence |
| I-90 | H | OMe | H | H | 3,4-MD-Ph | H | 3,4-MD-Ph | Presence |
| I-91 | H | OnBu | H | H | 4-OMe—Bn | H | 4-OMe—Ph | Presence |
| I-92 | H | OnBu | H | H | nBu | H | OiPr | Presence |

TABLE 4-continued

| Compound No. | R¹ | R² | R³ | R⁴ | *¹R⁵ | R⁶ | *¹R⁷ | Presence or absence of a bond |
|---|---|---|---|---|---|---|---|---|
| I-93 | H | OnBu | H | H | 2-Me-thiophen-5-yl | H | OiPr | Presence |
| I-94 | H | OnBu | H | H | 2-Me-thiophen-5-yl | H | 4-OMe—Ph | Presence |
| I-95 | H | OiPr | H | H | $(CH_2)_2CH=CH_2$ | H | 4-OMe—Ph | Presence |
| I-96 | H | $OCH_2CH(OEt)_2$ | H | H | 3,4-MD-Ph | H | 3,4-MD-Ph | Presence |
| I-97 | H | $OCH_2CH(OH)_2$ | H | H | 3,4-MD-Ph | H | 3,4-MD-Ph | Presence |
| I-98 | H | $O(CH_2)_3CH(OMe)_2$ | H | H | 3,4-MD-Ph | H | 3,4-MD-Ph | Presence |
| I-99 | H | $O(CH_2)_3CHO$ | H | H | 3,4-MD-Ph | H | 3,4-MD-Ph | Presence |
| I-100 | H | 2-(3-methoxypropyl)-5,5-dimethyl-1,3-dioxan-2-yl | H | H | 3,4-MD-Ph | H | 4-OMe—Ph | Presence |
| I-101 | H | $O(CH_2)_3CHO$ | H | H | 3,4-MD-Ph | H | 4-OMe—Ph | Presence |
| I-102 | H | $O(CH_2)_2CHO$ | H | H | 3,4-MD-Ph | H | 4-OMe—Ph | Presence |
| I-103 | H | OEt | H | H | 3,4-MD-Ph | H | 3,4-MD-Ph | Presence |
| Ia-5 | H | OiPr | H | H | 3,4-MD-Ph | Et | OMe | Presence |
| Ia-7 | H | OiPr | H | H | 3,4-MD-Ph | iPr | OMe | Presence |
| Ia-9 | H | OiPr | H | H | 3,4-MD-Ph | Me | Cl | Presence |
| Ia-11 | H | OnBu | H | H | 3,4-MD-Ph | Me | OiPr | Presence |
| Ia-12 | H | OiPr | H | H | 3,4-MD-Ph | Me | N(Me)(nBu) | Presence |
| Ia-13 | H | OiPr | H | H | 3,4-MD-Ph | Me | $O(CH_2)_3CH=CH_2$ | Presence |
| Ib-2 | H | OiPr | H | H | 3,4-MD-Ph | Me | 3,4-MD-Ph | Absence |
| I-104 | H | iPr | H | H | 3,4-MD-Ph | H | 3,4-MD-Ph | Presence |
| I-105 | H | iPr | H | H | 3,4-MD-Ph | H | 4-OMe—Ph | Presence |
| I-106 | H | OMe | OMe | H | 3,4-MD-Ph | H | 4-OMe—Ph | Presence |
| I-107 | H | OMe | OMe | H | 3,4-MD-Ph | H | 4-iPr—Ph | Presence |
| I-108 | H | H | H | OMe | 3,4-MD-Ph | H | 3,4-MD-Ph | Presence |
| I-109 | H | H | H | OMe | 3,4-MD-Ph | H | 4-OMe—Ph | Presence |
| I-110 | H | OMe | H | H | 3,4-MD-Ph | H | 4-OMe—Ph | Presence |
| I-111 | H | OiPr | H | H | $(CH_2)_3CHO$ | H | 4-OMe—Ph | Presence |
| I-112 | H | OiPr | H | H | 2-butyl-1,3-dioxolan-2-yl | H | 4-OMe-Ph | Presence |

TABLE 5

(I-S)

Compound structure with substituents R¹, R², R³, R⁴, R⁵, R⁶, R⁷ on a 2H-thiochromene-3-carboxylate scaffold.

| Compound No. | R¹ | R² | R³ | R⁴ | *¹R⁵ | R⁶ | *¹R⁷ |
|---|---|---|---|---|---|---|---|
| I-113 | H | OMe | H | H | 3,4-MD-Ph | H | 4-OMe—Ph |
| I-114 | OiPr | H | OnBu | H | 3,4-MD-Ph | H | H |
| I-115 | OMe | OH | H | OBn | 3,4-MD-Ph | H | H |
| I-116 | OEt | H | OPr | H | 3,4-MD-Ph | H | H |

TABLE 5-continued

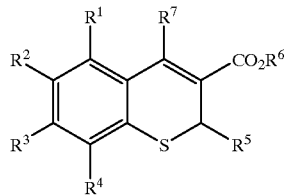

(I-S)

| Compound No. | $R^1$ | $R^2$ | $R^3$ | $R^4$ | *1$R^5$ | $R^6$ | *1$R^7$ |
|---|---|---|---|---|---|---|---|
| I-117 | H | OnPr | H | H | 3,4-MD-Ph | H | H |
| I-118 | OnPr | H | OMe | H | 3,4-MD-Ph | Me | H |
| I-119 | Me | OEt | H | H | 3,4-MD-Ph | Et | H |
| I-120 | Et | H | H | OnBu | 3,4-MD-Ph | nPr | H |
| I-121 | nPr | OH | OEt | H | 3,4-MD-Ph | iPr | H |
| I-122 | nBu | OMe | H | H | 3,4-MD-Ph | nBu | H |
| I-123 | H | OMe | H | OBn | 3,4-MD-Ph | H | 3,4-MD-Ph |
| I-124 | OiPr | H | OnBu | H | 3,4-MD-Ph | H | 3,4-MD-Ph |
| I-125 | OMe | OH | H | H | 3,4-MD-Ph | H | 3,4-MD-Ph |
| I-126 | OEt | H | OPr | H | 3,4-MD-Ph | H | 3,4-MD-Ph |
| I-127 | H | OnPr | H | H | 3,4-MD-Ph | H | 3,4-MD-Ph |
| I-128 | OnPr | H | OMe | H | 3,4-MD-Ph | Me | 3,4-MD-Ph |
| I-129 | Me | OEt | H | H | 3,4-MD-Ph | Et | 3,4-MD-Ph |
| I-130 | Et | H | H | OnBu | 3,4-MD-Ph | nPr | 3,4-MD-Ph |
| I-131 | nPr | OH | OEt | H | 3,4-MD-Ph | iPr | 3,4-MD-Ph |
| I-132 | nBu | OMe | H | H | 3,4-MD-Ph | nBu | 3,4-MD-Ph |
| I-133 | H | OMe | H | OBn | 3,4-MD-Ph | H | 2-OMe—Ph |
| I-134 | OiPr | H | OnBu | H | 3,4-MD-Ph | H | 2-OMe—Ph |
| I-135 | OMe | OH | H | H | 3,4-MD-Ph | H | 2-OMe—Ph |
| I-136 | OEt | H | OPr | H | 3,4-MD-Ph | H | 2-OMe—Ph |
| I-137 | H | OnPr | H | H | 3,4-MD-Ph | H | 2-OMe—Ph |
| I-138 | OnPr | H | OMe | H | 3,4-MD-Ph | Me | 2-OMe—Ph |
| I-139 | Me | OEt | H | H | 3,4-MD-Ph | Et | 2-OMe—Ph |

TABLE 6

| Compound No. | $R^1$ | $R^2$ | $R^3$ | $R^4$ | *1$R^5$ | $R^6$ | *1$R^7$ |
|---|---|---|---|---|---|---|---|
| I-140 | Et | H | H | OnBu | 3,4-MD-Ph | nPr | 2-OMe-Ph |
| I-141 | nPr | OH | OEt | H | 3,4-MD-Ph | iPr | 2-OMe-Ph |
| I-142 | nBu | OMe | H | H | 3,4-MD-Ph | nBu | 2-OMe-Ph |
| I-143 | H | OMe | H | OBn | 5-Me-2-Th | H | H |
| I-144 | OiPr | H | OnBu | H | 5-Me-2-Th | H | H |
| I-145 | OMe | OH | H | H | 5-Me-2-Th | H | H |
| I-146 | OEt | H | OPr | H | 5-Me-2-Th | H | H |
| I-147 | H | OnPr | H | H | 5-Me-2-Th | H | H |
| I-148 | OnPr | H | OMe | H | 5-Me-2-Th | Me | H |
| I-149 | Me | OEt | H | H | 5-Me-2-Th | Et | H |
| I-150 | Et | H | H | OnBu | 5-Me-2-Th | nPr | H |
| I-151 | nPr | OH | OEt | H | 5-Me-2-Th | iPr | H |
| I-152 | nBu | OMe | H | H | 5-Me-2-Th | nBu | H |
| I-153 | H | OMe | H | OBn | 5-Me-2-Th | H | 3,4-MD-Ph |
| I-154 | OiPr | H | OnBu | H | 5-Me-2-Th | H | 3,4-MD-Ph |
| I-155 | OMe | OH | H | H | 5-Me-2-Th | H | 3,4-MD-Ph |
| I-156 | OEt | H | OPr | H | 5-Me-2-Th | H | 3,4-MD-Ph |
| I-157 | H | OnPr | H | H | 5-Me-2-Th | H | 3,4-MD-Ph |
| I-158 | OnPr | H | OMe | H | 5-Me-2-Th | Me | 3,4-MD-Ph |
| I-159 | Me | OEt | H | H | 5-Me-2-Th | Et | 3,4-MD-Ph |
| I-160 | Et | H | H | OnBu | 5-Me-2-Th | nPr | 3,4-MD-Ph |
| I-161 | nPr | OH | OEt | H | 5-Me-2-Th | iPr | 3,4-MD-Ph |
| I-162 | nBu | OMe | H | H | 5-Me-2-Th | nBu | 3,4-MD-Ph |
| I-163 | H | OMe | H | OBn | 5-Me-2-Th | H | 2-MeO-Ph |
| I-164 | OiPr | H | OnBu | H | 5-Me-2-Th | H | 2-OMe-Ph |
| I-165 | OMe | OH | H | H | 5-Me-2-Th | H | 2-OMe-Ph |
| I-166 | OEt | H | OPr | H | 5-Me-2-Th | H | 2-OMe-Ph |
| I-167 | H | OnPr | H | H | 5-Me-2-Th | H | 2-OMe-Ph |
| I-168 | OnPr | H | OMe | H | 5-Me-2-Th | Me | 2-OMe-Ph |
| I-169 | Me | OEt | H | H | 5-Me-2-Th | Et | 2-OMe-Ph |

TABLE 6-continued

| Compound No. | R¹ | R² | R³ | R⁴ | *¹R⁵ | R⁶ | *¹R⁷ |
|---|---|---|---|---|---|---|---|
| I-170 | Et | H | H | OnBu | 5-Me-2-Th | nPr | 2-OMe-Ph |
| I-171 | nPr | OH | OEt | H | 5-Me-2-Th | iPr | 2-OMe-Ph |
| I-172 | nBu | OMe | H | H | 5-Me-2-Th | nBu | 2-OMe-Ph |

*¹The preceding numbers of the abbreviations represent positions of the substituents.

TABLE 7

| Compound | mp (° C.) | molecular formula | analytical value (Calculated) | analytical value (Found) | NMR *1) |
|---|---|---|---|---|---|
| I-1 | 174–176 (dec) | C27H22O8 | C, 68.35; H, 4.67 | C, 68.22; H, 4.80 | 1.19(m, 6H), 4.23(m, 1H),5.92(s, 2H), 6.02(s, 2H), 6.15(s, 2H), 6.30(s, 1H),6.69–6.74(m, 5H), 6.85–6.93(m, 3H) |
| (+)-I-1 | 131.5–134.5 | C27H22O8 | C, 68.35; H, 4.67 | C, 68.33; H, 4.77 | 1.19(m, 6H), 4.22(m, 1H), 5.91(s, 2H), 6.04(s, 2H), 6.15(s, 1H),6.30(m, 1H), 6.70–6.74 (m, 5H), 6.84–6.93(m, 3H) |
| (−)-I-1 | 131–133 | C27H22O8 | C, 68.35; H, 4.67 | C, 68.11; H, 4.81 | 1.19(m, 6H), 4.22(m, 1H), 5.91(s, 2H), 6.04(s, 2H), 6.15(s, 1H), 6.30(m, 1H), 6.70–6.74(m, 5H), 6.85–6.93 (m, 3H) |
| I-2 | 259.5–261 dec) | C24H20O6 0.1 MeOH | C, 70.74; H, 5.04 | C, 70.82; H, 4.94 | *2) 3.12(dd, 1H, J=10.0 and 11.0), 3.80(s, 3H), 4.53(d, 1H, J=11.0), 5.20(d, 1H, J=10.0), 5.96(s, 2H), 6.74–7.01(m, 8H), 7.10–7.19(m, 3H) |
| I-3 | 204–206 (dec) | C24H16O7 0.2 H2O | C, 68.64; H, 3.94 | C, 68.50; H, 3.90 | 5.92(s, 2H), 6.02(s, 2H), 6.71–6.98(m, 9H), 7.13–7.22(m, 1H) |
| I-4 | 192.5–194.5 | C24H18O6 | C, 71.63; H, 4.51 | C, 71.51; 4.58 | 3.87(s, 3H), 5.91(s, 2H), 6.22(s, 1H), 6.69–6.99(m, 8H), 7.15–7.23(m, 3H) |
| I-5 | 222–224 (dec) | C24H18O6 | C, 71.63; H, 4.51 | C, 71.56; H, 4.62 | 3.83(s, 3H), 5.89–5.91(m, 2H), 6.23(s, 1H), 6.62–6.84(m, 4H), 6.92–7.05(m, 3H), 7.12–7.26(m, 3H), 7.36–7.43(m, 1H) |
| I-6 | 188–190 (dec) | C24H18O6 | C, 71.63; H, 4.51 | C, 71.60; H, 4.61 | 3.82(s, 3H), 5.91(s, 2H), 6.23(s, 2H), 6.70–6.98(m, 9H), 7.14–7.39(m, 2H) |
| I-7 | 190–191 | C26H22O8 | C, 67.52; H, 4.80 | C, 67.45; H, 4.94 | 3.83(brs,6H), 3.92(s, 3H), 5.92(s, 2H), 6.25(s, 1H), 6.48(br, 1H), 6.71–6.86(m, 5H), 6.91–6.95(m, 2H), 7.16–7.25(m, 1H) |
| I-8 | 215–217 (dec) | C23H15ClO5 | C, 67.91; H, 3.72; Cl, 8.72 | C, 67.92; H, 3.87; Cl, 8.52 | 5.92(s, 2H), 6.23(s, 1H), 6.62–6.94(m, 6H), 7.13–7.25(m, 3H), 7.41(d, 2H, J=8.8) |
| I-9 | 217–219 (dec) | C24H18O5 | C, 74.60; H, 4.70 | C, 74.51; H, 4.58 | *2) 2.42(s, 3H),5.91(s,2H),626(s,1H),6.71–6.84(m,4H), 6.98–7.01(m, 2H),7.13–7.26(m, 5H) |
| I-10 | 178–180 | C26H22O5 | C, 75.35; H, 5.35 | C, 75.48; H, 5.47 | 0.98(t, 3H, J=7.4), 1.70(m, 2H), 2.66(t, 2H, J=7.0), 5.91(s, 2H), 6.22(s, 1H),6.69–6.84(m, 4H), 6.92–6.95(m, 2H), 7.13–7.21(m, 5H) |
| I-11 | 168–171 | C23H16O5 | C, 74.19; H, 4.33 | C, 74.04; H, 4.38 | 5.92(s, 2H), 6.23(s, 1H), 6.63–6.96(m, 6H), 7.14–7.22(m, 3H), 7.41–7.43(m, 3H) |
| I-12 | 190–192 | C26H22O5 | C, 75.35; H, 5.35 | C, 75.24; H, 5.45 | 1.29(s, 3H), 1.33(s, 3H), 2.97(m, 1H), 5.91(s, 2H), 6.23(s, 1H), 6.69–6.85(m, 5H), 6.92–6.96(m, 2H), 7.13–7.30(m, 4H) |

TABLE 8

| | | | | | |
|---|---|---|---|---|---|
| I-13 | 198–199 (dec) | C25H21NO5 0.2 H2O | C, 71.71; H, 5.15; N, 3.34 | C, 71.71; H, 5.24; N, 3.36 | *2) 3.01(s, 6H), 5.91(s, 2H), 6.24(s, 1H), 6.70–6.88(m, 6H), 6.97–7.01(m, 2H), 7.12–7.20(m, 3H) |
| I-14 | foam | C24H20O6 | C, 71.28; H, 4.98 | C, 71.20; H, 5.00 | *2) 3.14(dd, 1H, J=10.4 and 11.4), 3.82(s, 3H), 4.52(d, 1H, J=11.4), 5.11(d, 1H, J=10.4), 5.93(s, 2H), 6.65–6.94(m, 8H), 7.10–7.15(m, 2H), 7.42(d, 2H, J=8.6) |
| I-15 | 190–191 (dec) | C27H22O8 | C, 68.35; H, 4.67 | C, 68.20; H, 4.82 | 0.69(t, 3H, J=7.5), 1.14(m, 2H), 3.48(m, 2H), 5.91(s, 2H), 5.98(s, 2H), 6.13(s, 1H), 6.34(d, 1H, J=7.8), 6.54(d, 1H, J=8.2), 6.69–6.79(m, 4H), 6.93–6.96(m, 2H), 7.08–7.16(m, 1H) |
| I-16 | 189–191 (dec) | C27H22O8 | C, 68.35; H, 4.67 | C, 68.17; H, 4.80 | *2) 0.95(t, 3H, J=7.5), 1.68(m, 2H), 3.70(t-d, 2H, J=6.4 and 1.2), 5.92(s, 2H), 6.03(s, 2H), 6.18(s, 1H), 6.33–6.35(m, 1H), 6.71–6.97(m, 8H) |
| I-17 | 194–198 (dec) | C28H22O8 | C, 69.13; H, 4.56 | C, 68.98; H, 4.73 | 0.24(m, 2H), 0.57(m, 2H), 1.13(m, 1H), 3.57(d, 2H, J=4.4), 5.91(s, 2H), 6.04(s, 2H), 6.15(s, 1H), 6.34(m, 1H), 6.69–6.74(m, 5H), 6.85–6.93(m,3H) |
| I-18 | 180–182 (dec) | C31H22O8 0.2 H2O | C, 70.77; H, 4.22 | C, 79.75; H, 4.39 | 4.83(s, 2H), 5.92(s, 2H), 6.04(s, 2H), 6.15(s, 1H), 6.36(d, 1H, J=2.8), 6.69–6.92(m, 8H), 7.30–7.32(m, 5H) |
| I-19 | 175–176 (dec) | C27H22O8 | C, 68.35; H, 4.67 | C, 68.20; H, 4.87 | 0.98(t, 3H, J=7.2), 1.75(m, 2H), 3.84(t, 2H, J=6.4), 5.91(s, 2H), 6.03(s, 2H), 6.20(s, 2H), 6.29–6.37(m, 2H), 6.64–6.73(m, 3H), 6.84–6.94(m, 4H) |
| I-20 | 187–188 (dec) | C27H24O7 0.2 H2O | C, 69.88; H, 5.25 | C, 69.90; H, 5.31 | *2) 0.65(t, 3H, J=7.4), 1.05(m, 2H), 3.52(m, 2H), 3.85(s, 3H), 5.93(s, 2H), 6.15(s, 1H), 6.32(d, 1H, J=8.2), 6.63(d, 1H, J=8.2), 6.73(d, 1H, J=7.4), 6.86(d, 2H, J=7.4), 7.00–7.17(m, 5H) |
| I-21 | 198(dec) | C27H24O7 | C, 70.42; H, 5.25 | C, 70.42; H, 5.32 | *2) 0.93(t, 3H, J=7.2), 1.66(m, 2H), 3.67(t, 2H, J=6.4), 3.87(s, 3H), 5.92(s, 2H), 6.19(s, 1H), 6.28–6.29(m, 1H), 6.74–6.75(m, 3H), 7.20–7.23(m,2H) |

TABLE 8-continued

| | | | | | |
|---|---|---|---|---|---|
| I-22 | 190–191 (dec) | C26H22O7 | C, 69.94; H, 4.97 | C, 69.79; H, 5.10 | 1.26(t, 3H, J=7.0), 3.76(q, 2H, J=7.0), 5.91(s, 2H), 6.16(s, 1H), 6.26(s, 1H), 6.68–6.75(m, 3H), 6.86–7.14(m, 4H), 7.14–7.21(m, 2H) |
| I-23 | 198–199 (dec) | C28H26O7 | C, 70.87; H, 5.52 | C, 70.77; H, 5.52 | *2) 0.90(t, 3H, J=7.2), 1.28–1.47(m, 2H), 1.55–1.69(m, 2H), 3.71(t-d, 2H, J=6.1, 1.2), 5.92(s, 2H),6.19(s, 1H), 6.28–6.30(m, 1H), 6.70–6.74(m, 3H), 6.94–6.99(m, 4H),7.19–7.23(br, 2H) |
| I-24 | 206(dec) | C24H18O7 | C, 68.90; H, 4.34 | C, 68.89; H, 4.40 | 3.87(s, 3H), 5.91(s, 2H), 6.17–6.20(m, 2H), 6.64–6.75(m, 3H), 6.89–6.98 (m, 4H), 7.14–7.19(br, 2H) |

TABLE 9

| | | | | | |
|---|---|---|---|---|---|
| I-25 | 171–172.5 (dec) | C27H24O7 | C, 70.42; H, 5.25 | C, 70.31; H, 5.37 | 0.98(t, 3H, J=7.4), 1.75(m, 2H), 3.84(t, 2H, J=6.4), 3.87(s, 3H), 5.91(s, 2H), 6.21(s, 1H), 6.28–6.37(m, 2H), 6.59–6.74(m, 2H), 6.93–6.96(m, 4H), 7.17(br, 2H) |
| I-26 | 190–192 (dec) | C27H24O6 | C, 72.96; H, 5.44 | C, 72.71; H, 5.49 | 0.86(t, 3H, J=7.4), 1.47(m, 2H), 2.52(m, 2H), 3.87(s, 3H), 5.90(s, 2H), 6.24(s, 1H), 6.54–6.72(m, 3H), 6.91–7.05(m, 6H), 7.15–7.22(br, 2H) |
| I-27 | waxy oil | C26H20O9 | C, 65.55; H, 4.23 | *5) | *2) 3.84(s, 3H), 4.66(s, 2H), 5.88(d, 1H, J=1.0), 5.90(d, 1H, J=1.0), 6.27(s, 2H), 6.51–6.80(m, 6H), 6.94–6.96(m, 1H), 7.10–7.17(m, 3H) |
| I-28 | 191–193 (dec) | C27H24O7 | C, 70.42; H, 5.25 | C, 70.14; H, 5.43 | 0.69(t, 3H, J=7.5), 1.12(m, 2H), 3.39–3.56(m, 2H), 3.75(s, 3H), 5.96–5.98 (m, 2H), 6.18(s, 1H), 6.28(d, 1H, J=8.4), 6.52(d,1H, J=8.1), 6.76–6.83(m, 5H), 7.07–7.10(m, 1H), 7.39(d, 1H, J=8.7) |
| I-29 | 177–179 (dec) | C27H24O7 | C, 70.42; H, 5.25 | C, 70.20; H, 5.31 | 0.94(t, 3H, J=7.4), 1.67(m, 2H), 3.68(t, 2H, J=7.0), 3.75(s, 3H), 6.04(s, 2H), 6.19(s, 1H), 6.30(s, 1H), 6.73–6.89(m, 7H), 7.36(d, 2H, J=8.8), |
| I-30 | foam | C27H24O7 | C,70.43; H, 5.25 | C, 70.37; H, 5.33 | 0.97(t, 3H, J=7.4), 1.74(m, 2H), 3.83(t, 2H, J=6.6), 3.75(s, 3H), 6.03(s, 2H), 6.24–6.35(m, 2H), 6.66(d, 2H, J=8.4), 6.79–6.89(m, 3H), 7.37(d, 2H, J=8.6) |
| I-31 | 189.5(dec) | C27H26O7 | C, 70.12; H, 5.67 | C, 69.80; H, 5.77 | 1.00(t, 3H, J=7.4), 1.77(m, 2H), 3.07(m, 1H), 3.81(s, 3H), 3.85(t, 2H, J=6.7), 4.40(d, 1H, J=11.4), 5.05(d, 1H, J=10.2), 5.93(s, 2H), 6.60–6.90(m, 8H), 7.35(d, 2H, J=8.6) |
| I-32 | 190.5–192 (dec) | C27H24O6 | C, 72.96; H, 5.44 | C, 72.76; H, 5.72 | 0.83(t, 3H, J=7.4), 1.43(m, 2H), 2.50(t, 2H, J=6.8), 3.75(s, 3H), 6.03(s, 2H), 6.28(s, 1H), 6.60–6.89(m, 7H), 7.02(dd, 1H, J=2.0 and 7.2), 7.36 (d, 2H, J=8.8) |
| I-33 | 170–171 | C29H30O5 | C, 75.96; H, 6.59 | C, 75.83; H, 6.66 | 0.97(t, 3H, J=7.4), 1.30(d, 6H, J=7.0), 1.74(m, 2H), 2.96(m, 1H), 3.76 (s, 3H), 3.82(t, 2H, J=6.7), 6.26–6.35(m, 3H), 6.57(d, 1H, J=8.6), 6.79–7.41(m, 8H) |
| I-34 | 184.5–186.5 (dec) | C21H14O5S | C, 66.66; H, 3.73; S, 8.47 | C, 66.48; H, 3.97; S, 8.57 | *2) 5.92(s, 2H), 6.24(s, 1H), 6.71–7.22(m, 9H), 7.46(d, 1H, J=5.0) |
| I-35 | 191–192 (dec) | C24H18O6 | C, 71.63; H, 4.51 | C, 71.34; H, 4.60 | 3.75(s, 3H), 6.04(s, 2H), 6.25(s, 1H), 6.76–6.89(m, 8H), 7.13–7.21(m, 1H), 7.37(d, 2H, J=8.4) |
| I-36 | 179–181 | C27H24O7 | C, 70.43; H, 5.25 | C, 70.28; H, 5.30 | 1.15(d, 3H, J=6.0), 1.18(d, 3H, J=6.0), 3.87(s, 3H), 4.19(m, 1H), 5.91 (s, 2H), 6.15(s, 1H), 6.25(m, 1H), 6.69–6.74(m, 3H), 6.87–6.97(m, 4H), 7.15–7.19(br, 2H) |

TABLE 10

| | | | | | |
|---|---|---|---|---|---|
| (+)-I-36 | 158–159, 170–171 [α]D + 178.8 (c1.00, MeOH) | C27H24O7 | C, 70.43; H, 5.25 | C,70.20; H, 5.23 | 1.15(d, 3H, J=5.8), 1.18(d, 3H, J=5.8), 3.88(s, 3H), 4.19(m, 1H), 5.91 (s, 2H), 6.16(s, 1H), 6.25(m, 1H), 6.69–6.74(m, 3H), 6.90–6.97(m, 4H), 7.16–7.19(m, 2H) |
| (−)-I-36 | 158–159, 170–171 [α]D − 177.3 (c1.00, MeOH | C27H24O7 | C, 70.43; H, 5.25 | C, 70.32; H, 5.25 | 1.15(d, 3H, J=5.8), 1.18(d, 3H, J=5.8), 3.88(s, 3H), 4.19(m, 1H), 5.91 (s, 2H), 6.16(s, 1H), 6.25(m, 1H), 6.69–6.74(m, 3H), 6.90–6.97(m, 4H), 7.16–7.19(m, 2H) |
| Ia-1 | oil | C32H24O8 | C, 71.64; H, 4.51 | C, 71.60; H, 5.55 | 3.51(3H, s), 4.83(2H, s), 5.93(2H, s), 6.04(2H, s), 6.18(1H, s), 6.41(1H, d, J=3.2), 6.71–6.96(8H, m), 7.28–7.31(5H, m) |
| Ia-2 | oil | C25H18O8 | C, 67.26; H, 4.06 | | 3.51(s, 3H), 4.40(br, 1H), 5.92(s, 2H), 6.03(s, 2H), 6.17(s, 1H), 6.28(d, 1H, J=2.6), 6.67–6.74(m, 5H), 6.87–6.94(m, 3H) |
| Ia-3 | oil | C28H24O8 | C, 68.85; H, 4.95 | | 1.19(d, 3H, J=7.2), 1.22(d, 3H, J=7.2), 3.51(s, 3H), 4.25(m, 1H), 5.93 (s, 2H), 6.04(s, 2H), 6.16(s, 1H), 6.34(m, 1H), 6.71–6.74(m, 5H), 6.87–6.95(m, 3H) |
| Ia-4 | oil | C25H20O6 | C, 72.11; H, 4.84 | | 3.49(s, 3H), 3.87(s, 3H), 5.92(s, 2H), 6.24(s, 1H), 6.71–6.85(m, 4H), 6.95–7.00(m, 4H), 7.13–7.21(m, 3H) |
| Ia-6 | oil | C29H28O7 | C, 71.30; H, 5.78 | | 0.90(3H, t, J=7.1), 1.17(3H, d, J=5.9,); 1.19(3H, d, J=5.9), 3.87(3H, s), 3.92(2H, q, J=7.1), 4.21(1H, m), 5.92(2H, s), 6.18(1H, s), 6.31(1H, m), 6.68–7.23(10H, m) |

TABLE 10-continued

| | | | | | |
|---|---|---|---|---|---|
| Ia-8 | oil | C30H30O7 | C, 71.70; H, 6.02 | | 1.20(3H, d, J=6.2), 1.28(3H, d, J=6.2), 1.30(d, 6H, J=6.0), 3.94(3H, s), 4.41(1H, m), 5.09(1H, m), 5.96(2H, s), 6.15(1H, s), 6.66–6.89(5H, m), 7.02(1H, d, J=2.4), ca.7.1–7.24(1H, m) |
| Ia-10 | oil | C28H26O7 | C, 70.87; H, 5.52 | | 1.18(3H, t, J=6.0Hz), 1.19(3H, d, J=6.0), 3.48(3H, s), 3.87(3H, s), 4.21 (1H, m), 5.92(2H, s), 6.18(1H, s), 6.30(1H, m), 6.71–7.21(9H, m) |
| Ib-1 | 164–166 | C25H22O6 | C, 71.76; H, 5.30 | C, 71.60; H, 5.25 | 3.22(s, 3H), 3.29(dd, 1H, J=6.6, 2.6), 3.80(s, 3H), 4.67(d, 1H, J=6.6), 5.32(d, 1H, J=2.6), 5.96(s, 2H), 6.78–7.03(m, 8H), 7.11–7.24(m, 3H) |
| I-37 | 244–246 (dec) | C27H24O8, 0.6 H2O | C, 66.55; H, 5.21 | C,66.86; H, 5.64 | 1.20(d, 3H, J=6.1), 1.24(d, 3H, J=6.1), 3.09(t, 1H, J=10.5), 4.29(q, 1H, J=6.1), 4.46(d, 1H, J=10.5), 5.00(d, 1H, J=10.5), 5.94(s, 2H), 5.97(s, 2H), 6.33(d, 1H, J=2.1), 6.62(d, 1H, J=1.5), 6.65–6.91(m, 6H), 6.97(d, 1H, J=1.8) |

TABLE 11

| | | | | | |
|---|---|---|---|---|---|
| I-38 | 155–157 | C29H28O6 | C, 73.71; H, 5.97 | C, 73.65; H, 6.07 | 1.14(d, 3H, J=6.2), 1.18(d, 3H, J=6.2), 1.30(d, 6H, J=7.2), 2.97(m, 1H), 4.17(m, 1H), 5.91(s, 2H), 6.17(1H, s), 6.21(1H, s), 6.66–7.28(m, 9H) |
| I-39 | 185–186.5 | C27H26O6 | C, 72.63; H, 5.87 | C, 72.50; H, 6.02 | 1.15(d, 3H, J=5.8), 1.18(d, 3H, J=5.8), 3.75(s, 3H), 3.87(s, 3H), 4.18 (m, 1H), 6.20(s, 1H), 6.25(m, 1H), 6.72–7.38(m, 11H),7.19(brs,1H) |
| I-40 | 106–109, 155–156.5 *4) | C27H24O7 0.5 EtOH 0.7 H2O | C, 67.79; H, 5.77 | C, 67.87; H, 5.69 | *3)1.17(d, 3H, J=6.1), 1.20(d, 3H, J=6.1), 3.75(s, 3H), 4.22(m, 1H), 6.03 (s, 2H), 6.19(s, 1H), 6.30(m, 1H), 6.71–6.87(m, 7H), 7.35(d, 2H, J=5.6) |
| I-41 | 176–178 | C29H30O5 | C, 75.96; H, 6.59 | C, 75.68; H, 6.51 | 1.15(d, 3H, J=6.0), 1.17(d, 3H, J=6.0), 1.20(d, 6H, J=6.9), 2.85(m, 1H), 3.87(s, 3H), 4.18(m, 1H), 6.23(s, 1H), 6.24(m, 1H), 6.74–6.96(m, 4H), 7.15 (brs, 1H), 7.13(d, 2H, J=8.1), 7.35(d, 2H, J=8.1) |
| I-42 | 104–106 *4) | C29H28O6 EtOH | C, 71.85; H, 6.58 | C, 71.80; H, 6.61 | *3) 1.17(d, 3H, J=6.0), 1.20(d, 3H, J=6.0), 1.21(d, 6H, J=6.6), 2.85 (m, 1H), 4.22(m, 1H), 6.03(s, 2H), 6.22(s, 1H), 6.29(m, 1H), 6.70–6.77 (m, 4H), 6.85(d, 1H, J=5.0), 7.13(d, 2H, J=8.0), 7.34(d, 2H, J=8.0) |
| I-43 | 189–191 (dec) | C28H24O8 | C, 68.84; H, 4.95 | C, 68.73; H, 5.02 | 0.92(d, 6H, J=7.0), 1.93(m, 1H), 3.48(dd, 2H, J=6.4, 1.4), 5.91(s, 2H), 6.05 (s, 2H), 6.14(s, 1H), 6.30(m, 1H), 6.69–6.75(m, 5H), 6.86–6.92(m, 3H) |
| I-44 | 176–177.5 | C29H26O8 | C, 69.31; H, 5.22 | C, 69.08; H, 5.33 | 0.88(d, 6H, J=6.6), 1.53(m, 2H), 1.70(m, 1H), 3.75(t, 2H, J=6.6), 5.91 (s, 2H), 6.04(s, 2H), 6.15(s, 1H), 6.30(m, 1H), 6.69–6.75(m, 3H), 6.85–6.92(m, 5H) |
| I-45 | 190–192 (dec) | C30H28O8 | C, 69.76; H, 5.46 | C, 69.58; H, 5.70 | 0.87(d, 6H, J=6.4), 1.20–1.28(m, 2H), 1.46–1.72(m, 3H), 3.70(t, 2H, J=6.8), 5.91(s, 2H), 6.05(s, 2H), 6.15(s, 1H), 6.30(m, 1H), 6.69–6.75(m, 5H), 6.85–6.93(m, 3H) |
| I-46 | 184–185 | C29H24O8 | C, 69.59; H, 4.83 | C, 69.27; H, 4.99 | 0.03(m, 2H), 0.42(m, 2H), 0.74(m, 1H), 1.56(dt, 2H, J=7.0, 6.6), 3.80 (t, 2H, J=6.6), 5.91(s, 2H), 6.04(s, 2H), 6.15(s, 1H), 6.31(m, 1H), 6.69–6.76(m, 5H), 6.86–6.93(m, 3H) |
| I-47 | 195–197 (dec) | C30H28O8 | C, 69.75; H, 5.46 | C, 69.77; H, 5.54 | 0.90(s, 9H), 1.57(t, 2H, J=7.4), 3.80(t, 3H, J=7.4), 5.91(s, 2H), 6.03(s, 2H), 6.16(s, 1H), 6.29–6.31(m, 1H), 6.69–6.75(m, 5H), 6.85–6.96(m, 3H) |
| I-48 | 194–196 (dec) | C30H28O8 | C, 69.75; H, 5.46 | C, 69.76; H, 5.60 | 0.84(t, 6H, J=7,2), 1.29–1.58(m, 4H), 3.61(dd, 2H, J=1.4, 5.6), 5.91(s, 2H), 6.05(s, 2H), 6.15(s, 1H), 6.30(m, 1H), 6.69–6.75(m, 5H), 6.86–6.93(m, 3H) |

TABLE 12

| | | | | | |
|---|---|---|---|---|---|
| I-49 | 174–175.5 | C29H26O8 0.2 H2O | C, 68.82; H, 5.29 | C, 68.80; H, 5.29 | 0.83(m, 6H), 1.51(m, 4H), 3.75(m, 1H), 5.92(s, 2H), 6.04(s, 2H), 6.16 (s, 1H), 6.28(s, 1H), 6.70–6.74(m, 5H), 6.85–6.94(m, 3H) |
| I-50 | 174–176 | C31H30O8 | C, 70.17; H, 5.70 | C, 70.01; H, 5.90 | 0.83(s, 6H), 1.20–1.55(m, 8H), 3.85(m, 1H), 5.92(s, 2H), 6.03(s 2H), 6.16(s, 1H), 6.26(m, 1H), 6.70–6.75(m, 5H), 6.85–6.94(m, 3H) |
| I-51 | 183.5–185 (dec) | C29H24O8, 0.2 H2O | C, 69.10; H, 4.88 | C, 69.09; H, 5.11 | 1.53–1.74(m, 8H), 5.92(s, 2H), 6.04(s, 2H), 6.15(s, 1H), 6.27(m, 1H), 6.69–6.75(m, 5H), 6.86–6.93(m, 3H) |
| I-52 | 136–140 | C28H25NO8 1.0 H2O | C, 64.47; H, 5.22; N, 2.69 | C, 64.47; H, 5.13; N, 2.71 | *2) 2.41(s, 6H), 2.84(t, 2H, J=5.4), 3.86(t, 2H, J=5.4), 5.86(s, 2H), 5.87 (s, 2H), 6.14(s, 1H), 6.33(m, 1H), 6.62–6.78(m, 5H), 6.95–7.00(m, 3H) |
| I-53 | 159–161 | C20H18O6 | C, 67.79; H, 5.12 | C, 67.65; H, 5.27 | 1.30(6H, d, J=6.3), 4.40(1H, m), 5.90(2H, s), 6.10(1H, s), 6.68–6.85(6H, m), 7.71(1H, s) |
| I-54 | 131 | C2H12O7 | C, 65.62; H, 5.24 | C, 65.64; H, 5.28 | 1.30(3H, d, J=6.0), 1.31(3H, d, J=6.0), 4.01(3H, s), 4.43(1H, m), 5.89 (2H, s), 6.25(1H, s), 6.65–6.92(6H, m) |
| I-55 | 116–117 | C22H22O7 | C, 66.32; H, 5.57 | C, 65.98; H, 5.58 | 1.30(3H, d, J=6.0), 1.31(3H, d, J=6.0), 1.51(3H, t, J=7.0), 4.04–4.20 (1H, m), 4.33–4.48(2H, m), 5.89(2H, s), 6.28(1H, s), 6.66(1H, d, J=8.2), 6.78–6.86(5H, m) |

TABLE 12-continued

| I-56 | 129–130 | C23H24O7 | C, 66.98; H, 5.86 | C, 66.99; H, 5.87 | 1.10(3H, t, J=7.8), 1.30(3H, d, J=5.7), 1.31(3H, d, J=5.7), 1.93(2H, m), 3.93–4.01(1H, m), 4.23–4.31(1H, m), 4.41(1H, m), 5.89(2H, s), 6.27 (1H, s), 6.66(1H, d, J=8.1), 6.77–6.87(5H, m) |
|---|---|---|---|---|---|
| I-57 | 124–125 | C24H26O7 | C, 67.59; H, 6.14 | C, 67.65; H, 6.25 | 1.01(3H, t, J=7.4), 1.30(3H, d, J=6.0), 1.32(6H, d, J=6.0), 1.52(2H, m), 1.88(2H, m), 3.94–4.06(1H, m), 4.26–4.47(2H, m), 5.89(2H, s), 6.27 (1H, s), 6.67(1H, d, J=3.8), 6.78–6.86(5H, m) |
| I-58 | 110.5–112 | C25H28O7 | C, 68.17; H, 6.41 | C, 68.27; H, 6.41 | 0.95(3H, t, J=7.0), 1.32(6H, dd, J=2.2, 6.0), 1.42(4H, m), 1.82–1.97 (2H, m), 3.94–4.05(1H, m), 4.25–4.47(2H, m), 5.89(2H, s), 6.27(1H, s), 6.66(1H, d, J=7.4), 6.76–6.86(5H, m) |
| I-59 | 118–119.5 | C23H24O7 | C, 66.98; H, 5.87 | C, 66.94; H, 5.90 | 1.30–1.33(9H, m), 1.61(3H, d, J=6.3), 4.41(1H, m), 4.70(1H, m), 5.89 (2H, s), 6.30(1H, s), 6.65(1H, d, J=8.4), 6.76–6.82(5H, m) |
| I-60 | 129–131 | C24H24O7 | C, 67.91; H, 5.70 | C, 68.00; H, 5.81 | 0.36(2H, m), 0.72–0.76(2H, m), 1.03(3H, d, J=5.7), 1.30(3H, d, J=5.8), 1.32(3H, d, J=5.8), 3.82(1H, dd, J=7.8, 10.8), 4.27(1H, dd, J=7.8, 10.8), 4.41(1H, m), 5.89(2H, s), 6.28(1H, s), 6.66(1H, d, J=8.1), 6.77–6.86(5H, m) |

TABLE 13

| I-61 | 126–127 | C24H26O7 | C, 67.59, H, 6.15 | C, 67.40; H, 6.17 | 0.97(3H, t, J=7.2), 1.32(3H, d, J=6.2), 1.48(2H, m), 1.61(3H, d, J=6.2), 1.75(2H, m), 3.89(2H, dt, J=6.3, 1.8), 4.71(1H, m), 5.88(2H, s), 6.30 (1H, s), 6.63–6.83(6H, m), 10.7(1H, brs) |
|---|---|---|---|---|---|
| I-62 | 88–90 | C24H26O7 | C, 67.59; H, 6.14 | C, 67.64; H, 6.13 | 1.00(3H, t, J=7.4), 1.01(3H, t, J=7.4), 1.41–1.60(2H, m), 1.70–1.91 (4H, m), 3.88(2H, t, J=6.8), 3.93–4.04(1H, m), 4.24–4.36(1H, m), 5.89 (2H, s), 6.31(1H, s), 6.40(1H, d, J=2.4), 6.52(1H, dd, J=8.6, 2.4), 6.67 (1H, d, J=8.6), 6.79–6.84(2H, m), 7.25(1H, d, J=8.6) |
| I-63 | oil | C24H26O7 | C, 67.59, H, 6.14 | | 0.95(3H, t, J=7.4), 1.06(3H, t, J=7.4), 1.35–1.47(2H, m), 1.75–1.91 (4H, m), 3.80(1H, dt, J=7.1, 2.1), 3.88–4.03(2H, m), 4.30(1H, dt, J=7.1, 2.1), 5.87(2H, s), 6.33(1H, s), 6.47(1H, d, J=8.4), 6.54(1H, d, J=8.1), 6.64(1H, d, J=8.1), 6.78–6.82(2H, m), 7.15–7.21(1H, m) |
| I-64 | oil | C30H38O7 | C, 70.57, H, 7.50 | | 0.89(3H, brm), 1.26–1.33(18H, m), 1.48(2H, brm), 3.99(1H, dt, J=9.9, 6.6), 4.30(1H, dt, J=9.9, 6.6), 4.37–4.45(1H, m), 5.89(2H, s), 6.27 (1H, s), 6.66(1H, d, J=8.1), 6.77–6.85(5H, m) |
| I-65 | 119–120.5 | C25H26O7 | C, 68.48, H, 5.98 | C, 68.43; H, 5.97 | 1.31(3H, d, J=5.9), 1.32(3H, d, J=5.9), 2.00(2H, m), 2.27(2H, m), 4.01 (1H, m), 4.31(1H, m), 4.41(1H, m), 5.03–5.14(2H, m), 5.82(1H, m) 5.89(2H, s), 6.27(1H, s), 6.66(1H, d, J=8.1), 6.76–6.87(5H, m) |
| I-66 | 114–116 | C29H34O9 | C, 66.15, H, 6.51 | C, 66.08; H, 6.52 | 0.75(3H, s), 1.20(3H, s), 1.33(3H, d, J=6.0), 1.34(3H, d, J=6.0), 1.75–2.17(4H, m), 3.45(2H, d, J=10.4), 3.65(2H, d, J=11.0), 4.00–4.46 (2H, m), 4.44(1H, m), 4.55(1H, t, J=2.6), 5.91(2H, s), 6.30(1H, s), 6.68 (1H, d, J=7.6), 6.73–6.92(5H, m) |
| I-67 | 94–96 | C26H30O7 | C, 68.71; H, 6.65 | C, 68.65; H, 6.59 | 0.89–0.94(3H, brm), 1.31(3H, d, J=5.3), 1.33(3H, d, J=6.3), 1.35(4H, m), 1.43–1.51(2H, m), 1.84–1.94(2H, m), 3.99(1H, dt, J=9.9, 6.9), 4.31(1H, dt, J=9.9, 6.9), 4.37–4.45(1H, m), 5.89(2H, s), 6.27(1H, s), 6.66(1H, d, J=8.1), 6.77–6.86(5H, m) |
| I-68 | 110–111 | C25H28O8 | C, 65.78; H, 6.18 | C, 65.60; H, 6.20 | 1.31(3H, d, J=5.7), 1.32(3H, d, J=5.7), 1.64(4H, m), 1.92(2H, m), 3.70 (2H, m), 4.02(1H, m), 4.30(1H, m), 4.41(1H, m), 5.89(2H, s), 6.26 (1H, s), 6.66(1H, d, J=8.1), 6.76–6.89(5H, m) |
| I-69 | 116–120 | C24H23NO7 0.2 H2O | C, 65.36; H, 5.35 N, 3.18 | C, 65.42; H, 5.44 N, 3.22 | 1.31(6H, d, J=6.0), 2.21(2H, m), 2.70(2H, t, =7.0), 4.04–4.35(2H, m), 4.44(1H, m), 5.90(2H, s), 6.20(1H, s), 6.68(1H, d, J=8.2), 6.72–6.88 (4H, m), 6.91(1H, d, J=2.8) |

TABLE 14

| I-70 | 60–62 | C26H30O9 | C, 64.19; H, 6.22 | | 1.31(3H, d, J=6.0), 1.32(3H, d, J=6.0), 1.72–2.07(4H, m), 3.35(3H, s), 3.36(3H, s), 3.96–4.48(4H, m), 5.89(2H, s), 6.26(1H, s), 6.66(1H, d, J=8.2), 6.72–6.90(5H, m) |
|---|---|---|---|---|---|
| I-71 | oil | C24H24O8 | C, 65.45; H, 5.49 | | 1.32(3H, d, J=6.0), 1.33(3H, d, J=6.0), 2.12–2.31(2H, m), 2.65–2.80(2H, m), 3.96–4.36(2H, m), 4.44(1H, m), 5.91(2H, s), 6.25(1H, s), 6.63–6.92 (6H, m) |
| I-72 | 98–102 | C27H32O7 | C, 69.21; H, 6.88 | C, 69.22; H, 6.86 | 0.90(3H, t, J=6.8), 1.31(3H, d, J=6.0), 1.32(3H, d, J=6.0), 1.26–1.40 (6H, m), 1.48(2H, m), 1.84–1.94(2H, m), 3.99(1H, dt, J=9.6, 6.6), 4.31 (1H, dt, J=9.6, 6.6), 4.37–4.45(1H, m), 5.89(2H, s), 6.27(1H, s), 6.66 (1H, d, J=8.1), 6.77–6.86(5H, m) |
| I-73 | 113–115 | C24H26O6 | C, 70.23; H, 6.39 | C, 70.21; H, 6.40 | *2)0.84(3H, t, J=7.2), 1.00(3H, t, J=7.2), 1.36–1.61(4H, m), 1.81–1.95 (2H, m), 2.46–2.53(2H, m), 3.93–4.04(1H, m), 4.26–4.38(1H, m), 5.88(2H, s), 6.34(1H, s), 6.65(1H, d, J=8.6), 6.79–6.94(3H, m), 7.11–7.23(2H, m) |
| I-74 | 188–190 | C27H24O8 | C, 68.06; H, 5.09 | C, 67.80; H, 5.12 | *2) 1.06(3H, d, J=6.0), 1.19(3H, d, J=6.0), 3.75(3H, s), 4.11–4.29(1H, m), 5.92(2H, s), 6.30(1H, s), 6.69–6.97(10H, m) |

TABLE 14-continued

| | | | | | |
|---|---|---|---|---|---|
| I-75 | 129–130 | C30H30O8 0.9 H2O | C, 69.46; H, 6.18 | C, 69.30; H, 5.86 | 0.97(3H, t, J=7.3), 1.46(2H, m), 1.69(2H, m), 3.12(2H, m), 3.80(3H, s), 3.73(2H, m), 4.16(1H, m), 4.44(1H, m), 5.88(2H, s), 6.25(1H, s), 6.63–7.23(10H, m) |
| I-76 | 140–141 | C24H26O6 | C, 70.23; H, 6.38 | C, 70.21; H, 6.51 | 0.98(3H, t, J=6.8), 1.30(3H, d, J=6.0), 1.31(3H, d, J=6.0), 1.38–1.74 (4H, m), 3.08(2H, m), 4.40(1H, m), 5.89(2H, s), 6.13(1H, s), 6.66(1H, d, J=7.8), 6.73–6.85(3H, m), 6.74(1H, d, J=7.8), 6.96(1H, d, J=2.2) |
| I-77 | 146–147 | C25H28O6 | C, 70.74; H, 6.65 | C, 70.73; H, 6.68 | 0.93(3H, t, J=6.6), 1.30(3H, d, J=6.0), 1.31(3H, d, J=6.0), 1.34–1.55 (4H, m), 1.66(2H, m), 3.07(2H, m), 4.40(1H, m), 5.89(2H, s), 6.13(1H, s), 6.66(1H, d, J=8.0), 6.73–6.90(3H, m), 6.75(1H, d, J=8.0), 6.96 (1H, d, J=2.2) |
| I-78 | 165–166 | C23H24O6 | C, 69.68; H, 6.10 | C, 69.69; H, 6.22 | 1.30(3H, d, J=6.0), 1.31(3H, d, J=6.0), 1.32(3H, d, J=72), 1.58(3H, d, J=7.2), 4.06(1H, m), 4.38(1H, m), 5.89(2H, s), 6.09(1H, s), 6.60(1H, d, J=8.0), 6.72(2H, d, J=1.4), 6.74–6.84(2H, m), 7.15(1H, t, J=1.6) |
| I-79 | 162–165 | C25H26O6 | C, 71.07; H, 6.20 | C, 70.96; H, 6.14 | 1.29(3H, d, J=6.0), 1.30(3H, d, J=6.0), 1.66–2.40(8H, m), 4.21(1H, m), 4.32(1H, m), 5.89(2H, s), 6.11(1H, s), 6.65(1H, d, J=7.8), 6.72(2H, d, J=1.4), 6.68–6.84(2H, m), 6.97(1H, m) |

TABLE 15

| | | | | | |
|---|---|---|---|---|---|
| I-80 | 137–141 158–162 *4) | C25H22O6S | C, 66.65; H, 4.92; S, 7.12 | C, 66.39; H, 5.04; S, 7.07 | 1.20(3H, d, J=6.0), 1.21(3H, d, J=6.0), 2.54(3H, s), 4.26(1H, m), 5.91 2H, s), 6.14(1H, s), 6.55(1H, m), 6.66–6.80(4H, m),6.82–6.96(3H, m) |
| I-81 | 157–159 | C28H26O7 0.3 H2O | C, 70.08; H, 5.59 | C, 70.04; H, 5.45 | 1.18(6H, d, J=6.0), 3.76(3H, s), 423(1H, m), 4.45(2H, s), 5.90(2H, s), 6.21(1H, s), 6.64–6.73(3H, m), 6.77–6.92(3H, m), 6.81(2H, d, J=8.8), 7.18(2H, d, J=8.8) |
| 1-82 | 158–160 | C26H30O6 | C, 71.21; H, 6.90 | C, 71.08; H, 6.96 | 0.90(3H, t, J=7.0), 1.30(3H, d, J=6.0), 1.31(3H, d, J=6.0), 1.23–1.74 (8H, m), 3.07(2H, m), 4.40(1H, m), 5.89(2H, s), 6.13(1H, s), 6.66(1H, d, J=7.6), 6.70–6.86(4H, m), 6.96(1H, d, J=2.4) |
| I-83 | 176–178 | C25H28O6 | C, 70.74; H, 6.65 | C, 70.30; H, 6.69 | 1.00(6H, d, J=6.2), 1.30(3H, d, J=6.2), 1.31(3H, d, J=6.2), 1.45–1.65 (2H, m), 1.76(1H, m), 3.07(2H, m), 4.39(1H, m), 5.89(2H, s), 6.13(1H, s), 6.66(1H, d, J=7.4), 6.70–6.85(4H, m), 6.96(1H, d, J=2.4) |
| I-84 | 126–129 | C24H26O7 | C, 67.59; H, 6.15 | C, 67.52; H, 6.18 | 1.30(6H, d, J=6.2), 1.94(2H, m), 3.15(2H, m), 3.36(3H, s), 3.49(2H, m), 4.42(1H, m), 5.89(2H, s), 6.12(1H, s), 6.66(1H, d, J=7.8), 6.74(1H, d, J=7.8), 6.75(1H, d, J=2.6), 6.76–6.86(2H, m), 7.05(1H, d, J=2.2) |
| I-85 | 206–210 | C27H30O6 0.2 H2O | C, 71.41; H, 6.75 | C, 71.52; H, 6.65 | 0.95–1.85(11H, m), 1.30(3H, d, J=6.0), 1.31(3H, d, J=6.0), 2.86(1H, m), 3.39(1H, m), 4.39(1H, m), 5.88(2H, s), 6.15(1H, s), 6.65(1H, d, J=7.8), 6.70–6.86(4H, m), 6.94(1H, d, J=2.0) |
| I-86 | 147–149 | C24H24O6 | C, 70.57; H, 5.92 | C, 70.57; H, 6.03 | 1.31(3H, d, J=6.0), 1.32(3H, d, J=6.0), 2.30–2.53(2H, m), 3.05–3.34 (2H, m), 4.41(1H, m), 4.97–5.19(2H, m), 5.90(2H, s), 5.95(1H, m), 6.15(1H, m), 6.68(1H, d, J=7.8), 6.71–6.90(4H, m), 6.97(1H, d, J=2.2) |
| I-87 | 144–146 | C24H26O7 | C, 67.59; H, 6.15 | C, 67.64; H, 6.35 | 1.30(3H, d, J=6.0), 1.31(3H, d, J=6.0), 1.50–1.93(5H, m), 2.85–3.23 (2H, m), 3.70–3.92(2H, m), 4.41(1H, m), 5.89(2H, s), 6.14(1H, s), 6.66 (1H, d, J=7.8), 6.70–6.87(4H, m), 6.97(1H, d, J=1.8) |
| I-88 | 177 | C20H17ClO6 | C, 61.78; H, 4.41; Cl, 9.12 | C, 61.70; H, 4.45; Cl, 9.00 | 1.31(6H, d, J=6.0), 4.45(1H, m), 5.90(2H, s), 6.24(1H, s), 6.66–6.85 (5H, m), 7.23–7.26(1H, m) |
| I-89 | 138–142 | C24H26O6S | C, 65.14; H, 5.92; S, 7.25 | C, 64.96; H, 5.85; S, 6.98 | 0.88(3H, t, J=7.2), 1.17–1.69(4H, m), 1.31(6H, d, J=6.0), 1.32(3H, d, J=6.0), 2.83(2H, t, J=7.4), 4.44(1H, m), 5.89(2H, s), 6.37(1H, s), 6.64 (1H, m), 6.72(1H, dd, J=1.6, 0.6), 6.73–6.87(3H, m), 7.27(1H, m) |
| I-90 | 207–210 (dec) | C25H18O8 | C, 67.26; H, 4.06 | C, 67.16; H, 4.29 | 3.62(3H, s), 5.92(2H, s), 6.02(2H, s), 6.19(1H, s), 6.34(1H, m), 6.71–6.76(5H, m), 6.86–6.97(3H, m) |

TABLE 16

| | | | | | |
|---|---|---|---|---|---|
| (+)-I-54 | 127–128.5 [α]D + 51.0 (c 1.00, MeOH) | C21H20O7 | C, 65.62, H, 5.24 | C, 65.60; H, 5.25 | 1.30(3H, d, J=6.0), 1.33(3H, d, J=6.0), 4.01(3H, s), 4.43 (1H, m), 5.89(2H, s), 6.25(1H, s), 6.65–6.92(6H, m) |
| (+)-I-76 | 148–149 [α]D + 61.3 (c 1.00, MeOH) | C24H26O6 | C, 70.23, H, 6.38 | C, 70.01; H, 6.43 | 0.98(3H, t, J=7.20), 1.30(3H, d, J=6.0), 1.31(3H, d, J=6.0), 1.38–1.73(4H, m), 2.92–3.22(2H, m), 4.40(1H, m), 5.89 (2H, s), 6.13(s, 1H), 6.66(1H, d, J=7.8), 6.70–6.86(4H, m), 6.96(1H, d, J=2.2) |
| I-91 | 169–171 | C28H28O6 | C, 73.03; H, 6.13 | C, 72.85; H, 6.18 | 1.21(3H, d, J=6.0), 1.22(3H, d, J=6.0), 2.84–3.17(2H, m), 3.79(3H, s), 3.88(3H, s), 4.24(1H, m), 5.33(1H, dd, J=9.4, 3.4), 6.26(1H, d, J=1.8), 6.78–6.90(4H, m), 6.96(2H, d, J=8.6), 7.13(4H, d, J=8.6) |
| I-92 | oil | C21H30O5 | C, 69.59; H, 8.34 | C, 69.75; H, 8.49 | 0.84(3H, t, J=7.3), 0.99(3H, t, J=7.3), 1.27(3H, d, J=6.0), 1.57(3H, d, J=6.3), 1.20–1.80(10H, m), 3.93(2H, dt, J=6.3, 2.1), 4.63(1H, m), 5.28 (1H, m), 6.79(1H, m), 6.89(2H, m) |

TABLE 16-continued

| | | | | | |
|---|---|---|---|---|---|
| I-93 | 104–105 | C22H26O5S | C, 65.65; H, 6.51 S, 7.97 | C, 65.53; H, 6.48 S, 7.91 | 0.98(3H, t, J=7.2), 1.31(3H, d, J=6.2), 1.48(2H, m), 1.60(3H, d, J=6.2), 1.76(2H, m), 2.34(3H, s), 3.91(2H, dt, J=1.0, 6.2), 4.70(1H, m), 6.47–6.49(2H, m), 6.73(1H, d, J=3.6), 6.84–6.87(3H, m) |
| I-94 | 178–181 (dec) | C26H26O5S | C, 69.31; H, 5.82 S, 7.12 | C, 69.32; H, 5.90 S, 6.97 | 0.89(3H, t, J=7.2), 1.37(2H, m), 1.62(2H, m), 2.37(3H, s), 3.70(2H, dt, J=1.2, 6.6), 3.88(3H, s), 6.26(1H, m), 6.38(1H, m), 6.54(1H, m), 6.77–6.97(5H, m), 7.15(1H, br) |
| I-95 | 161–163 | C24H26O5 | C, 73.08, H, 6.64 | C, 72.89; H, 6.68 | 1.19(3H, d, J=6.0), 1.21(3H, d, J=6.0), 1.60–2.34(4H, m), 3.87(3H, s), 4.23(1H, m), 4.90–5.22(3H, m), 5.82(2H, s), 6.25(1H, d, J=1.8)), 6.76–7.16(6H, m) |
| I-96 | oil | C30H28O10 | C, 65.69, H, 5.14 | | 1.18(6H, t, J=7.2), 3.49–3.60(2H, m), 3.63–3.73(2H, m), 3.77(2H, d, J=5.0), 4.69(1H, t, J=5.0), 5.91(2H, s), 6.04(2H, s), 6.14(1H, s), 6.34(1H, m), 6.69–6.92(8H, m) |
| I-97 | oil | C29H26O10 | C, 65.16, H, 4.90 | | *2) 3.76–3.79(2H, m), 4.74(1H, t, J=4.0), 5.91(2H, s), 6.02(2H, s), 6.18(1H, s), 6.39(1H, s), 6.70–6.76(5H, m), 6.85–6.95(3H, m) |
| I-98 | oil | C30H28O10 | C, 65.69, H, 5.14 | | 1.68–1.69(4H, m), 3.29(6H, s), 3.72–3.75(2H, m), 4.34–4.37(1H, m), 5.90(2H, s), 6.04(2H, s), 6.14(1H, s), 6.69–6.74(5H, m), 6.85–6.92(3H, m) |

TABLE 17

| | | | | | |
|---|---|---|---|---|---|
| I-99 | oil | C28H22O9 | C, 66.93; H, 4.41 | | 1.99(2H, m), 2.57(2H, t, J=7.0), 3.76(2H, t, J=6.0), 5.91(2H, s), 6.04(2H, s),6.14(1H, s), 6.28(1H, m), 6.68–6.74(5H, m), 6.85–6.93(3H, m) |
| I-100 | 123–125 | C33H34O9 | C, 68.97; H, 5.96 | C, 68.84; H, 6.00 | 0.70(3H, s), 1.15(3H, s), 1.68–1.79(4H, m), 3.37(2H, d, J=11.1), 3.56(2H, d, J=11.1), 3.69–3.73(2H, m), 4.41(1H, t, J=4.7), 5.96(2H, s), 6.15(1H, s), 6.25 (1H, s), 6.69–6.74(3H, m), 6.90–6.97(4H, m), 7.12(2H, br), 9.76(1H, s) |
| I-101 | 202–204 (dec) | C28H24O8 | C, 68.85; H, 4.95 | C, 68.53; H, 5.15 | 1.92–2.01(2H, m), 2.56(2H, dt, J=1.5, 7.2), 3.69–3.76(2H, m), 3.89(3H, s), 5.91(2H, s), 6.16(1H, s), 6.22(1H, d, J=2.4), 6.69–6.77(3H, m), 6.90–6.97(4H, m), 7.17(2H, br), 9.76(1H,s) |
| I-102 | oil | C27H22O8 | c, 68.35; H, 4.67 | | 2.75(2H, t, J=4.0), 3.81(2H, m), 4.05(2H, t, J=4.0), 5.88(2H, s), 6.09 (1H, s), 6.22(1H, s), 6.67–6.76(3H, m), 6.88–6.92(4H, m), 7.12(br, 2H), 9.77(1H, s) |
| I-103 | 212–212.5 (dec) | C26H20O8 | C, 67.82; H, 4.38 | C, 67.74; H, 4.67 | 1.28(3H, t, J=7.2), 3.79(2H, q, J=7.2), 5.91(2H, s), 6.04(2H, s), 6.15(1H, s), 6.31(1H, m), 6.69–6.75(5H, m), 6.85–6.92(3H, m) |
| I-104 | 126(dec) | C27H22O7 EtOH | C, 69.04; H, 5.59 | C, 68.90; H, 5.55 | *3) 1.06, 1.07(6H, d, J=6.8), 2.67(1H, m), 5.91(2H, s), 6.05(2H, s), 6.18(1H, s), 6.94–7.08(9H, m) |
| I-105 | 206(dec) | C27H24O6 0.6 H2O | C, 71.23; H, 5.58 | C, 71.10; H, 5.66 | *2) 1.06(6H, d, J=6.9), 1.07 (6H, d, J=6.9), 2.67(1H, m), 3.88(3H, s), 5.92(2H, s), 6.22(1H, s), 6.59(1H, d, J=2.4), 6.72–6.78(2H, m), 6.96–7.07 (6H, m), 7.2(br, 1H) |
| I-106 | 226–228 (dec) | C26H22O8 | C, 67.53; H, 4.79 | C, 67.36; H, 4.53 | *2) 2.01(3H, s), 2.15(3H, s), 3.88(3H, s), 5.91(2H, s), 6.21(1H, s), 6.47 (1H, s), 6.64(1H, s), 6.73(1H, dd, J=7.2, 0.9), 6.96–7.00(4H, m), 7.2(br, 2H) |
| I-107 | 217(dec) | C28H26O7 | C, 70.87; H, 5.52 | C, 70.89; H, 5.96 | *2) 1.31(6H, d, J=6.9), 2.01(3H, s), 2.15(3H, s), 2.98(1H, s), 5.91(2H, s), 6.21(1H, s), 6.46(1H, s), 6.64(1H, s), 6.73(1H, dd, J=7.5, 0.9), 6.97–7.01(2H, m), 7.20(2H, br), 7.28(2H, d, J=8.7) |
| I-108 | 196–198 (dec) | C25H18O8 EtOH | C, 65.85; H, 4.91 | C, 65.60; H, 5.01 | *2, *3) 3.84(3H, s), 5.91(2H, s), 6.01(2H, s), 6.32(1H, s), 6.42(1H, dd, J=7.7, 1.2), 6.70–7.03(8H, m) |
| I-109 | 199–201 (dec) | C25H20O7 0.7 EtOH | C, 68.24; H, 5.25 | C, 68.29; H, 5.22 | *2, *3) 3.84(3H, s), 3.86(3H, s), 5.91(2H, s), 6.34(1H, s), 6.37(1H, dd, J=7.6, 1.5), 6.68–7.05(8H, m), 7.17–7.22(2H, br) |
| I-110 | 207–210 (dec) | C25H18O8 | C, 67.26; H, 4.06 | C, 67.16; H, 4.29 | *2) 3.62(3H, s), 5.92(2H, s), 6.02(2H, s), 6.19(1H, s), 6.34(1H, m), 6.71–6.76(5H, m), 6.86–6.97(3H, m) |

TABLE 18

| | | | | | |
|---|---|---|---|---|---|
| I-111 | 132–134 | C24H26O6 | C, 70.23; H, 6.38 | C, 69.95; H, 6.45 | 1.18(3H, d, J=6.0), 1.21(3H, d, J=6.0), 1.50–2.08(4H, m), 2.38–2.54(2H, m), 3.87(3H, s), 4.23(1H, m), 5.15(1H, dd, J=9.6, 2.6), 6.25(1H, d, J=2.0), 6.76–6.98(4H, m), 7.08(2H, d, J=8.0), 9.75(1H, t, J=1.5) |
| I-112 | 138–140 | C26H30O7 | C, 68.71; H, 6.65 | C, 68.48; H, 6.74 | 1.18(3H, d, J=6.0), 1.21(3H, d, J=6.0), 1.50–2.10(6H, m), 3.75–4.02(4H, m), 3.86(3H, s), 4.22(1H, m), 4.85(1H, t, J=3.6), 5.16(1H, dd, J=10.0, 1.4), 6.25(1H, d, J=1.8), 6.75–7.12(6H, m) |
| I-113 | 205 (dec) | C25H20O6S | C, 66.95; H, 4.49 S, 7.15 | C, 66.91; H, 4.55 S, 7.05 | *2) 3.62(3H, s), 3.86(3H, s), 4.99(1H, s), 5.88(2H, s), 6.45(1H, d, J=2.8), 6.62–6.96(7H, m), 7.18(2H, d, J=8.4) |
| Ia-5 | 49 | C23H24O7 | C, 66.98; H, 5.87 | C, 66.96; H, 5.95 | 1.30(6H,d,J=6.0), 1.27(3H, t, J=7.1), 3.95(3H, s), 4.22(2H, q, J=7.1), 4.43(1H, m), 5.89(2H, s), 6.16(1H, s), 6.65–7.03(6H, m) |

TABLE 18-continued

| | | | | |
|---|---|---|---|---|
| Ia-7 | oil | C24H26O6 | C, 70.23; H, 6.38 | 1.20(3H, d, J=6.2), 1.28(3H, d, J=6.2), 1.30(6H, d, J=6.0), ,3.94(3H, s), 4.41(1H, m), 5.09(1H, m), 5.89(2H, s), 6.15(1H, s), 6.65–6.89(5H, m), 7.02(1H, d, J=2.4), ca7.1–7.24(1H, m) |
| Ia-9 | oil | C21H19O6Cl | C, 62.61; H, 475 | 1.31(6H, d, J=6.0), 3.78(3H, s), 4.52(1H, m), 5.91(2H, s), 6.23(1H, s), 6.67–6.84(5H, m), 7.22(1H, d, J=2.7) |
| Ia-11 | oil | C25H28O7 | c, 68.17; H, 641 | 0.96(3H, t, J=7.5), 1.32(3H, d, J=6.0), 1.42(3H, d, J=6.0), 1.47(2H, m), 1.74(2H, m), 3.76(3H, s), 3.89(2H, t, J=6.5), 4.51(1H, m), 5.88(2H, s), 6.21(1H, s), 6.34–6.87(5H, m), 6.99(1H, d, J=3.0) |
| Ia-12 | oil | C26H31NO6 | C, 68.86; H, 6.89 | 0.89(3H, t, J=7.3), 1.25(3H, d, J=6.0), 1.29(3H, d, J=6.0), 1.22–1.43 (2H, m), 1.64(2H, m), 2.95(3H, s), 3.23(2H, t, J=6.8), 3.73(3H, s), 4.37 (1H, m), 5.87(2H, s), 6.03(1H, s), 6.63(1H, d, J=6.6), 6.76–6.85(4H, m), 6.91(1H, d, J=2.4) |
| Ia-13 | oil | C26H28O7 | C, 69.01; H, 6.24 | 1.30(6H, d, J=6.3), 1.95(2H, m), 2.29(2H, m), 3.75(3H, s), 3.97–4.18 (2H, m), 4.40(1H, m), 4.98–5.12(2H, m), ca. 5.84(2H, m), 5.89(2H, s), 6.17(1H, m), 6.66–6.88(5H, m), 7.02(1H, d, J=2.7) |
| Ib-2 | 220–221 (dec) | C28H26O8 | C, 68.56; H, 5.34   C, 68.40; H, 5.32 | *7) 1.14(3H, d, J=6.0), 1.18(3H, d, J=6.0), 3.11(3H, s), 4.31(1H, m), 4.75(1H, d, J=6.9), 5.35(1H, d, J=2.6), 6.00(2H, d, J=3.3), 6.02(2H, s), 6.30(1H, d, J=2.4), 6.60–6.78(3H, m), 6.83–6.95(5H, m) |

*1: Unless otherwise stated, $^1$H-NMR spectra were recorded at 200 or 300 MHz in CDCl$_3$ solution with tetramethylsilane as an internal standard. Chemical shifts and coupling constants are reported by δ (ppm) and Hz, respectively, and the following abbreviations are used.
s, singlet; d, doublet; t, triplet; q, quartet; m, multiplet; br, broad signal
*2: measured in CDCl$_3$ + CD$_3$OD
*3: Residual ethanol signals were observed at 1.23 (t, J=7.4) and 3.70 (q, J=7.2) since ethanol was contained as a solvent for crystallization.
*4: Double melting points including the case either of them is ambiguous.
*5: contaminated by a starting material.
*6: the compound was not recrystallized for purification.
*7: measured in DMSO-d6.

Experiment 1 Measurement of affinity for endothelin A (ETA) receptor

Affinities for the ETA receptor were measured from the potency for inhibition of binding of $^{125}$I-labeled endotheline-1 to smooth muscle A7r5 cells derived from rat aorta. In brief, the cells cultured in 48-well plates were washed with buffer, and incubated in 0.3 ml of Hepes buffered Hanks' solution containing labeled endothelin-1 (8.3 pM) and various kinds of protease inhibitors in the presence or absence of the compound of the present invention at 37° C. for 1 h. The incubation was terminated by rapid removal of the incubation medium and the cells were washed with a HEPES buffered Hanks' solution. The radioactivity of $^{125}$I-labeled endothelin-1 bound to the cells was determined with a gamma-counter. The specific binding was calculated by subtracting the non-specific binding which was determined in the presence of $10^{-7}$ M non radioactive endothelin-1 from the total binding. The IC$_{50}$ value was represented by the concentration of the compound of the present invention which inhibits specific $^{125}$I-labeled endothelin-1 binding by 50%.

Experiment 2 Measurement of affinity for endothelin B (ETB) receptor

Affinities for the ETB receptor were measured from the potency for inhibiting $^{125}$I-labeled endothelin-3 binding to COS-7 cells expressing the pig endothelin ETB receptor. In brief, a plasmid vector to which the pig endothelin ETB receptor gene was inserted was transfected to COS-7 cells by the lipofectin method. After the cells were washed with buffer, $10^3$–$10^4$ cells were dispersed in HEPES buffered Hanks' solution (0.1 ml) containing 25 pM of 125I labeled endothelin-3 and various kinds of protease inhibitors and incubated in the presence or absence of the compound of the present invention at 37° C. for 1 h. After completion of the reaction, the radioactivity bound was trapped by a glass fiber filter and measured with a gamma counter. Specific binding was calculated by subtracting the non-specific binding measured in the presence of $10^{-7}$ M non-radioactive endothelin-3 from the total binding. The IC$_{50}$ value was represented by the concentration of the compound of the present invention which inhibits the specific binding of $^{125}$I-labeled endothelin-3 by 50%.

The results in experiments 1 and 2 are shown in table 19.

TABLE 19

| Compound No. | ETA IC$_{50}$(nM) | ETB IC$_{50}$(nM) |
|---|---|---|
| I-36 | 0.89 | 180 |
| I-56 | 1.5 | 1300 |
| I-57 | 0.41 | 780 |
| I-58 | 0.48 | 150 |
| I-59 | 0.81 | 730 |
| I-65 | 0.38 | 130 |
| I-67 | 0.67 | 78 |
| I-68 | 0.95 | 880 |
| I-70 | 1.2 | 270 |
| I-74 | 0.21 | 58 |
| I-76 | 0.73 | 610 |
| I-77 | 0.32 | 150 |
| I-78 | 0.63 | 2500 |
| I-79 | 0.53 | 350 |
| I-80 | 1.0 | 1800 |
| I-81 | 0.50 | 85 |
| I-82 | 0.62 | 69 |
| I-83 | 1.9 | 480 |
| I-84 | 1.8 | 710 |
| I-85 | 0.58 | 46 |
| I-86 | 2.7 | 950 |
| I-87 | 2.3 | 1800 |
| I-89 | 0.27 | 100 |

Experiment 3 Inhibition of macrophage foam cell formation

Male golden Syrian hamster of 12 weeks old, were used for the experiment. Hamsters were classified into a group wherein hamsters were fed with usual powder diet (OD group), a group wherein hamsters were fed with diet containing high cholesterol (2%) (HCD group) and a group wherein hamsters were fed with diet containing high cholesterol (2%) and the compound I-36 of the present invention (HCD +I-36 group) and animals in each group were fed for 6 weeks. The added amount of the compound 1-36 of the present invention was 0.01, 0.03 and 0.1% and they were equivalent to 6, 19, 66 mg/kg, respectively, calculated from food intake. Each group contains 8 hamsters.

After feeding for 6 weeks, hamsters were anesthetized with pentobarbital and subjected to thoracotomy to expose a heart. Arch of the aorta was removed after reperfusion with phosphate-buffered 10% formalin solution from the ventricle. The arch of the aorta was opened longitudinally and the number of foam cells in a microphotograph after staining with oil red O was counted with a colony counter to calculate the number per aortic arch area. The significant difference between the groups was examined by Dunnett's multiple comparison test.

The results were shown in table 20. In the HCD group, the number of foam cells was about 10 times as many as that in the OD group. The foam cell formation was significantly suppressed in the groups wherein the compound of the present invention was administered.

TABLE 20

| | Aortic foam cell numbers / mm² (Mean ± SE) |
|---|---|
| OD | 2.5 ± 1.2** |
| HCD | 25.7 ± 2.7 |
| HCD + 0.01% I-36 | 10.1 ± 1.7** |
| HCD + 0.03% I-36 | 9.1 ± 0.8** |
| HCD + 0.1% I-36 | 8.8 ± 1.1** |

**: $p < 0.01$ vs HCD group

Experiment 4 Effect on peripheral circulatory insufficiency

Using Wistar rats, the peripheral circulatory insufficiency model was produced by immersing the rat tail tip (2–3 cm) in 1° C. water for 9 h, and experiments were performed at 3 weeks after above treatment. Tail blood flows in peripheral circulatory insufficiency rats were measured with laser-Doppler flowmetry with a tablet probe during immersing the whole tail in 3° C. water (30 min) The probe was held directly adjacent to the ventral surface of the tail, approximately 14 cm from the tip. To evaluate the effects of the compound of the present invention, peripheral circulatory insufficiency rats administered by the compound of the present invention (I-36, 30 mg/kg, po) at 2 h before 3° C. immersion.

In the normal Wistar rats, tail blood flow was transiently declined after 3° C. immersion, and gradually recovered up to about 70 % of basal level at 25 to 30 min after the immertion (normal rat). On the other hand, in the peripheral circulatory insufficiency rats, the tail blood flow measured immediately before administration of the compound of the present invention recovered to no more than 40% of basal level (peripheral circulatory insufficiency rat). In peripheral circulatory insufficiency rats treated with the compound of the present invention (insufficiency rat +I-36), however, the recovery of the tail blood flow was remarkable and significant (Table 21). Three days after administration of the compound of the present invention, when the circulatory effects of the compound was supposed to fully disappear, tail blood flows during 3° C. immersion were measured again. The recovery of the blood flow was same as that before administration of the compound of the present invention (wash out). These results suggest the therapeutic usefulness of the compound of the present invention for the treatment of peripheral circulatory insufficiency. For statistic analysis, Dunnett's test was used.

TABLE 21

Average of the blood flow from 20–25 min after cold exposure (n = 4)

| | skin blood flow (%) |
|---|---|
| normal rat | 70.49 ± 3.08 |
| insufficiency rat | 37.20 ± 3.29 |
| insufficiency rat + I-36 | 62.02 ± 1.23** |
| wash out | 44.19 ± 5.83 |

**:$p < 0.01$ vs insufficiency rat control

Formulation Example 1 Tablet

All of the following ingredients other than calcium stearate were homogeneously mixed, then the mixture was granulated. Calcium stearate was added to the granules to form 130 mg of tablet for oral administration.

| | |
|---|---|
| The compound (I-1) | 50 mg |
| Lactose | 46 mg |
| Corn starch | 20 mg |
| Low-substituted hydroxypropylcellulose | 8 mg |
| Hydroxypropylcellulose | 5 mg |
| Calcium stearate | 1 mg |
| total | 130 mg |

Industrial Applicability

As are demonstrated above, the compound group (I) has endothelin receptor antagonistic activities. The compound group (I) can be a very useful medicament for various diseases caused by endothelin. Endothelin antagonists are also useful as a macrophage forming inhibitor.

What is claimed is:

1. A pharmaceutical composition for use as an endothelin receptor antagonist comprising a compound of the formula (Iα):

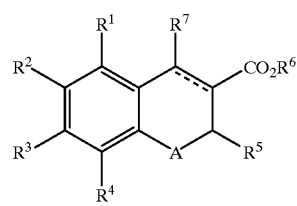

wherein $R^1$, $R^3$ and $R^4$ are each independently hydrogen, optionally substituted alkyl, optionally substituted alkenyl, optionally substituted alkynyl, optionally substituted cycloalkyl, hydroxy, halogen, optionally substituted alkoxy, optionally substituted alkenyloxy, optionally substituted alkynyloxy, optionally substituted cycloalkoxy, optionally substituted acyloxy or optionally substituted amino, $R^2$ is an optionally substituted alkoxy, $R^5$ is optionally substituted alkyl, optionally substituted alkenyl, optionally substituted alkynyl, optionally substituted aryl, optionally substituted heterocyclic or optionally substituted cycloalky, R⁶ is hydrogen, optionally substituted alkyl or optionally substituted aryl, R⁷ is hydrogen, optionally substituted alkyl, optionally substituted alkenyl, optionally substituted alkynyl, optionally substituted cycloalkyl, halogen, optionally substituted alkoxy, optionally substituted alkenyloxy, optionally substituted alkynyloxy, optionally substituted aryl, optionally substituted aryloxy, optionally substituted heterocyclic, optionally substituted heterocyclooxy, optionally substituted acyloxy, optionally substituted alkylthio, optionally substituted alkenylthio, optionally substituted alkynylthio, or optionally substituted amino, A is —S or O and a broken line represents presence or absence of a bond, or pharmaceutically acceptable salt or hydrate thereof as an active ingredient.

2. A compound of the formula (I):

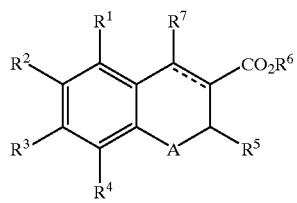

wherein R¹–R⁶, A and a broken line are the same as defined in claim 1, R⁷ is optionally substituted alkyl, optionally substituted alkenyl, optionally substituted alkynyl, optionally substituted cycloalkyl, optionally substituted alkenyloxy, optionally substituted alkynyloxy, optionally substituted aryl, optionally substituted aryloxy, optionally substituted heterocyclic, optionally substituted heterocyclooxy, optionally substituted acyloxy, optionally substituted alkylthio, optionally substituted alkenylthio, optionally substituted alkynylthio or optionally substituted amino, or pharmaceutically acceptable salt or hydrate thereof.

3. The compound claimed in claim 2 wherein R⁷ is optionally substituted alkyl, optionally substituted alkenyl, optionally substituted alkynyl, optionally substituted cycloalkyl, optionally substituted alkenyloxy, optionally substituted alkynyloxy, optionally substituted aryl, optionally substituted aryloxy, optionally substituted heteroaryl, optionally substituted heterocyclooxy, optionally substituted acyloxy, optionally substituted alkenylthio or optionally substituted alkynylthio, or pharmaceutically acceptable salt or hydrate thereof.

4. The compound claimed in claim 2 wherein R⁷ is optionally substituted alkyl, alkenyl, alkynyl, cycloalkyl, alkenyloxy, optionally substituted aryl, optionally substituted aryloxy or optionally substituted thienyl, or pharmaceutically acceptable salt or hydrate thereof.

5. The compound of claim 2 wherein R¹, R³, and R⁴ are each independently hydrogen, optionally substituted alkyl, hydroxy or optionally substituted alkoxy, R² is optionally substituted alkoxy, or pharmaceutically acceptable salt or hydrate thereof.

6. The compound claimed in claim 2 wherein R⁵ is optionally substituted alkyl, optionally substituted alkenyl, optionally substituted aryl or optionally substituted heterocyclic, or pharmaceutically acceptable salt or hydrate thereof.

7. The compound of claim 2 wherein R¹ and R³ are each independently hydrogen or optionally substituted alkoxy, R² is an optionally substituted alkoxy, R⁴ is independently hydrogen, alkyl or optionally substituted alkoxy, R⁵ is optionally substituted aryl or optionally substituted heterocyclic, R6 is hydrogen or alkyl, R⁷ is optionally substituted alkyl, optionally substituted aryl or optionally substituted aryloxy and A is O, or pharmaceutically acceptable salt or hydrate thereof.

8. The compound claimed in claim 2 wherein R¹ is hydrogen, R² is optionally substituted alkoxy, both of R³ and R⁴ are hydrogen, R⁵ is benzodioxol-5-yl, R⁶ is hydrogen, R⁷ is hydrogen, halogen, optionally substituted alkoxy, thienyl, optionally substituted amino or optionally substituted alkylthio, A is O and a broken line represents presence of a bond, or pharmaceutically acceptable salt or hydrate thereof.

9. A pharmaceutical composition comprising the compound or pharmaceutically acceptable salt or hydrate thereof claimed in any one of claims 2–8.

10. A method for treating or preventing a disease associated with endothelin in a patient, which comprises administering an effective amount of the compound or pharmaceutically acceptable salt or hydrate thereof claimed in any one of claims 2–8 to a patient in need thereof.

11. A method for inhibiting macrophage foam cell formation comprising administering to a patient in need thereof an endothelin receptor antagonist comprising the compound of claim 1.

* * * * *